United States Patent
Haefner et al.

(10) Patent No.: US 9,127,260 B2
(45) Date of Patent: Sep. 8, 2015

(54) SYNTHETIC PHYTASE VARIANTS

(75) Inventors: Stefan Haefner, Speyer (DE); Annegret Welzel, Ludwigshafen (DE); Robert Thummer, Mannheim (DE)

(73) Assignee: BASF SE, Ludwigshafen (DE)

( * ) Notice: Subject to any disclaimer, the term of this patent is extended or adjusted under 35 U.S.C. 154(b) by 24 days.

(21) Appl. No.: 14/113,100

(22) PCT Filed: Apr. 18, 2012

(86) PCT No.: PCT/IB2012/051930
§ 371 (c)(1),
(2), (4) Date: Oct. 21, 2013

(87) PCT Pub. No.: WO2012/143861
PCT Pub. Date: Oct. 26, 2012

(65) Prior Publication Data
US 2014/0044835 A1    Feb. 13, 2014

Related U.S. Application Data

(60) Provisional application No. 61/477,645, filed on Apr. 21, 2011.

(30) Foreign Application Priority Data

Apr. 21, 2011  (EP) ..................................... 11163453

(51) Int. Cl.
*C12N 9/16* (2006.01)
*A23K 1/165* (2006.01)

(52) U.S. Cl.
CPC ................ *C12N 9/16* (2013.01); *A23K 1/1653* (2013.01); *C07K 2319/21* (2013.01)

(58) Field of Classification Search
None
See application file for complete search history.

(56) References Cited

U.S. PATENT DOCUMENTS 8,557,555 B2 * 10/2013 Haefner et al. ............... 435/196
2008/0263688 A1 10/2008 Lassen et al.

OTHER PUBLICATIONS

International Search Report for PCT/IB2012/051930 mailed Aug. 10, 2012.

* cited by examiner

*Primary Examiner* — Christian Fronda
(74) *Attorney, Agent, or Firm* — Marshall, Gerstein & Borun LLP

(57) ABSTRACT

The invention relates to a synthetic phytase with elevated thermostability, elevated stability to acids at p H 2, elevated stability to pepsin and with a broadened active p H range, and to an isolated nucleic acid sequence coding for a synthetic phytase and to the use of the phytase in an animal feed for reducing the phosphate content in the slurry and to animal feed additives and animal feeds comprising the synthetic phytase.

18 Claims, 6 Drawing Sheets

SYNTHETIC PHYTASE VARIANTS

RELATED APPLICATIONS

This application is a national stage application (under 35 U.S.C. §371) of PCT/IB2012/051930, filed Apr. 18, 2012, which claims benefit of U.S. Provisional Application No. 61/477,645, filed Apr. 21, 2011, and European Application No. 11163453.1, filed Apr. 21, 2011.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_12810_01571. The size of the text file is 70 KB and the text file was created on Oct. 16, 2013.

The present invention relates to phytases, to amino acid sequences coding for phytase enzymes and to nucleotide sequences which code for phytases, and to processes for the preparation and the use of phytases and to animal feeds comprising these phytases.

Phosphorus is an essential element for the growth of living organisms. In animal production, feed, as a rule, has to be supplemented with inorganic phosphorus in order to achieve good growth rates. In cereals and pulses, phosphorus is stored mainly in the form of phytate. However, monogastric animals such as pigs, poultry and fish are not capable of directly absorbing phytate or phytic acid, which results in the excretion of phytate, which means phosphorus overloads in regions with intensive livestock production. Furthermore, phytic acid, which binds metals such as calcium, copper or zinc, acts as a substance with a negative effect on the metabolism of monogastric animals. In order to compensate for the phosphate deficit of these animals and to ensure sufficient growth and sufficient health, inorganic phosphate is added to the animal feed. This addition of inorganic phosphate is costly and leads to a further adverse effect on the environment. By using a phytase in animal feeds, the phytate is hydrolyzed and results in a lower content of inositol phosphate and inorganic phosphates in the slurry. The addition of phytases to animal feeds improves the availability of organic phosphorus and reduces the adverse effect on the environment by excreted, phytate-bound phosphates. The literature describes a variety of natural phytases, both of fungal and of bacterial origin.

Phytases, also referred to as myo-inositol hexakisphosphate phosphohydrolase, are a class of phosphatases which are capable of cleaving at least one phosphate residue from phytate.

EP 420 358 generally describes the cloning and expression of microbial phytases, WO 2006/38062 describes microbial phytases derived from *Citrobacter freundii* as additive to animal feeds, and WO 2007/112739 describes phytases based on a natural phytase from *Citrobacter braakii* and processes for its preparation and the use in animal feeds.

Haefner et al. (Haefner S., Knietsch A., Scholten E., Braun J., Lohscheidt M. and Zelder O. (2005) Biotechnological production and application of phytases. Appl Microbiol Biotechnol 68:588-597) describe a multiplicity of known uses of phytases in the field of human or animal nutrition. Further uses of phytases such as, for example, the use for hydrolyzing biomass or starch in the production of bioethanol are described in WO 2008/097620.

WO 2008/116878 and WO 2010/034835 describe a phytase from *Hafnia alvei*, its protein sequence and variants thereof. Zinin et al. (FEMS Microbiology Letters (2004) 236: 283-290) disclose a phytase from *Obesumbacterium proteus*, whose sequence is deposited at the UNIPROT database with the accession number Q6U677. The patent applications WO 2006/043178, WO 2008/097619 and WO 2008/092901 describe phytases from various *Buttiauxella* sp. The natural phytases with the currently highest specific activities include the natural phytases from *Yersinia intermedia* (WO 2007/128160) and *Yersinia pestis* (WO 02/048332).

However, all of these currently available phytases do not show those properties which are required for the preparation of animal feed additives. The currently available phytases are not sufficiently thermally stable for being employed in the preparation of animal feed pellets without a considerable loss of their activity. In the preparation of animal feed pellets, phytase together with further customary animal feed components is compressed under high temperatures and humidity in order to be fed to the livestock as one entity. An effective destruction of *salmonella* sp. and the gelatinization of the starch is only achieved above a temperature of 80° C. during the preparation (Amerah et al. Worlds Poulty Science Journal (2011) 67:29-45). This compressing under hot and humid conditions results in considerable phytase activity losses. One possibility of preventing this loss of activity is the laborious coating of the phytase particles, so that they are protected against the effect of heat. This coating of the phytase additions causes considerable additional costs as the result of the fats or polymers employed for the coating. The doses of commercial phytases are usually determined on the basis of the activity determination at pH 5.5 (DIN ISO 30024:2009) and is not adapted to match the pH in the respective digestive tract. This results in considerable misdosages by variation of the activity at pH values other than 5.5.

It was therefore an object of the present invention to provide a phytase which has a sufficient thermal stability, so that it can be employed in the preparation of *salmonella*-free feed pellets without additional protective measures such as coating and with activity losses which are as low as possible. It was a further object of the invention to provide a phytase which can be employed over a wide pH range accompanied by as little reduction of the enzymatic activity as possible, so that it can be employed in the various pH ranges of the digestive tracts of different animal species and so that a sufficient enzymatic activity in the digestive tract is ensured even when the pH range fluctuates as the result of varying feed components.

This object is achieved by a synthetic phytase which has an amino acid sequence with at least 90% identity to the amino acid sequence of SEQ ID 24.

The synthetic phytase according to the invention preferably has an amino acid sequence with at least 94%, especially preferably 95% and by preference 96, 97, 98 or 99% identity with the amino acid sequence of SEQ ID 24.

The phytases according to the invention have a thermostability of at least 80° C. and are therefore suitable for being employed in the preparation of feed pellets without suffering a considerable activity loss as the result of the hot and moist conditions during pelleting.

They furthermore have a broad pH range of over 3 pH units, within which they retain at least 50% of the activity determined at pH 5.5, so that, when the dosage is determined on the basis of the activity at 5.5, they can be employed in a multiplicity of animals with different digestive pH and together with different feed components, without an unduly low dosage resulting in activity losses and therefore to an increased excretion of the phosphate by the animals.

Furthermore, the phytase according to the invention surprisingly have an elevated proteolytic stability, and therefore they can pass through the stomach without substantial activity losses and the activity at the actual site of action, in the gut, is retained. Furthermore, the phytases according to the invention have a stability at pH 2 of at least 85% and thus ensure the activity being retained in the highly acidic range.

The identity between two protein sequences or nucleic acid sequences is defined as the identity calculated by the program needle in the version available in April 2011. Needle is part of the freely available program package EMBOSS, which can be downloaded from the website http://emboss.sourceforge.net/. The standard parameters are used: gapopen 10.0 ("gap open penalty"), gapextend 0.5 ("gap extension penalty"), datafile EBLOSUM62 (matrix) in the case of protein and datafile EDNAFULL (matrix) in the case of DNA.

In a particular embodiment, the phytases with the following amino acid sequences are excepted from the invention: SEQ ID 18 and its mutants A-4; A-10; A-66; A-73; C-7; C-40; X-1; X-2; A-164; B-16; B-378; C-79; A-11; X-6; B-320; A-508; A-8; A-20; A-507; A-8; A-20; A-507; X-3; A-505; A-501; A-407; A-502; X-4; A-408; A-415; A-501; A-409; A-503; A-406; A-510; A-515; D-5; D-34; F-161; A-504; D-192; A-511; A-514; A-516; F-41; D-207; D-268; F-150; I-117; A-509; H-107; H-159; H-456; A-512; H-464; A-513; A-518; A-521; A-534 and A-519 (definition as in table 6).

In a particular embodiment, the invention comprises the described phytases according to the invention, with phytases with the amino acid sequences of the group consisting of SEQ ID 18 and the mutants as described in table 6 being excepted.

TABLE 6

Mutants of the amino acid sequence SEQ ID 18 Mutant number Mutation(s) starting from sequence SEQ ID 18

| Mutant | Mutation(s) |
|---|---|
| A-4 | Q349R |
| A-10 | A84V/A304V |
| A-66 | H228Y |
| A-73 | N202S |
| C-7 | T320L/H413L |
| C-40 | K234N |
| X-1 | Q256Y |
| X-2 | K207E/A209S/N270K |
| A-164 | A6V |
| B-16 | K207E |
| B-378 | H143Y |
| C-79 | Q109K/D247K |
| A-11 | Q256H/K402N |
| X-6 | K207E/A209S |
| B-320 | M137L/K207T |
| A-508 | Q349R/H228Y/A304V |
| A-8 | K234I/K251N/H413Q |
| A-20 | D92E |
| A-507 | N202S/H228Y |
| X-3 | D92P |
| A-505 | D92E/N202S |
| A-501 | D92E/K234I/K251N/H413Q |
| A-407 | A89T/D92A/N270K |
| A-502 | D92E/Q256H |
| X-4 | A89T/D92A |
| A-408 | A89T/D92A/K207E/A209S |
| A-415 | A89T/D92A/S261E |
| A-501 | D92E/K234I/K251N/H413Q |
| A-409 | A89T/D92A/S248L/Q256Y |
| A-503 | D92E/K234I/K251N/Q256H/H413Q |
| A-406 | A89T/D92A/Q256Y |
| A-510 | D92E/N202S/K234I/K251N/Q256Y/H413Q/K207E/A209S |
| A-515 | D92E/N202S/A209S/K234I/Q256Y/H413Q |
| D-5 | D92E/A142T/K234I/K251N/Q256H/H413Q |
| D-34 | S1N/S17N/D92E/K234I/K251N/Q256H/H413Q |
| F-161 | K12N/D92E/K234I/K251N/Q256H/H413Q |
| A-504 | D92E/N202S/K234I/K251N/Q256H/H413Q |
| D-192 | D92E/S140P/K207I/K234I/K251N/Q256H/H413Q |
| A-511 | D92E/M137L/N202S/K234I/K251N/Q256H/H413Q |
| A-514 | D92E/N202S/K234I/K251N/Q256H/K402N H413Q |
| A-516 | D92E/N202S/K234I/E243K/K251N/Q256H/H413Q |

TABLE 6-continued

Mutants of the amino acid sequence SEQ ID 18 Mutant number Mutation(s) starting from sequence SEQ ID 18

| Mutant | Mutation(s) |
|---|---|
| F-41 | D92E/D138N/K234I/K251N/Q256H/H413Q |
| D-207 | D92E/Q149H/K234I/K251N/Q256H/H413Q |
| D-268 | D92E/T156R/K234I/K251/Q256H/H413Q |
| F-150 | D92E/K234I/K251N/A255V/Q256H/H413Q |
| I-117 | D92E/N202T/K234I/K251N/Q256H/S373I/E382G/T399I/H413Q |
| A-509 | A89T/D92A/N202S/K234I/K251N/Q256H/H413Q |
| H-107 | D92E/N202S/K234I/K251N/Q256H/H413Q |
| H-159 | A89T/D92A/N202S/K207E/K234I/K251N/Q256H |
| H-456 | A89T/D92A/K207E/K234I/K251N/Q256H/H413Q |
| A-512 | D92E/H143Y/K234I/K251N/Q256H/H413Q |
| H-464 | A89T/D92A/G205R/K207E/V208M/K251N/Q256H |
| A-513 | D92E/H/228Y/K234I/K251N/Q256H/H413Q |
| A-518 | A89T/D92A/H143Y/N202S/K207E/A209S/H228Y/K234I/K251N/Q256H/H413Q |
| A-521 | A89T/D92N/A142T/H143Y/N202S/K207E/A209S/H228Y/K234I/D247K/K251N/Q256H/F356L/H413Q |
| A-534 | A89T/D92A/H143Y/T156R/N202S/K207E/A209S/H228Y/K234I/K251N/Q256H/S314G/H413Q |
| A-519 | A89T/D92A/A142T/H143Y/N202S/K207E/A209S/H228Y/K234I/D247K/K251N/Q256H/H413Q |

In a particular embodiment, the invention comprises a phytase which has an amino acid sequence with at least 90%, preferably 91, 92, 93, 94, 95, 96, 97, 98 or 99%, identity with the amino acid sequence of SEQ ID 24, with phytases with the amino acid sequences of the group consisting of SEQ ID 18 and the mutants as described in table 6 being excepted.

In accordance with a particular embodiment, the synthetic phytase has an amino acid modification at at least one of the positions selected from the group consisting of position 1, 2, 3, 4, 5, 6, 7, 8, 9, 12, 16, 33, 37, 67, 71, 75, 76, 77, 78, 92, 109, 118, 119, 120, 121, 123, 136, 141, 144, 152, 155, 156, 159, 164, 166, 193, 200, 217, 258, 260, 261, 268, 270, 276, 300, 322, 345, 346, 371, 374, 398 and 406, based on the position according to SEQ ID 24. For the purposes of the present invention, modification is understood as meaning a substitution of the original amino acid as mentioned in SEQ ID 24 of the sequence listing by another amino acid. Here, the amino acids are referred to by the usual one-letter code. By modifying one or more amino acids, it is possible further to enhance the thermostability of the synthetic phytase and/or to enhance the stability to pepsin or to widen the optimum pH range.

Advantageously, the synthetic phytase has at least 5 modifications in the amino acid sequence based on the SEQ ID 24, in particular it has at least 6, 7, 8, 9 or 10 and very specially preferably at least 15 modifications.

In a preferred embodiment, the synthetic phytase has at least one of the following modifications in comparison with the amino acid sequence of SEQ ID 24:
S1-; D2-,E; T3Q, A4G,E; PSA; A6S,D; G7K; F8Y,M; Q9K; K12R; L16V; N33D,M; H37Y; R67L; Q71E; P75N; K76N,I; D77T; N78T; D92A,E,N,T,V; Q109N,E; Q118S; N119A,T; I120L; Q121T; A123V; S136K; Q141K; A144E; T152G,A; E155N; T156G; Q159N; S164E; A166E,H; Q193L; A200N; S217G; D258N; M260I; S261H; K268N; N270Q; Q276N; I300L; T322Q; D345G; N346G; L371A; H374N; D398E; Q406K.

In this context, the amino acid of SEQ ID 24 which is mentioned before the respective position number (position according to SEQ ID 24) is replaced by one of the amino acids mentioned after the position number. A "-" represents a deletion of the amino acid in question. In this context, any possible amino acid substitution mentioned in combination with any of the remaining changes is possible.

Advantageously, the synthetic phytase of the present invention comprises at least 5 of the abovementioned modifications, in particular at least 6, 7, 8, 9 or 10 and particularly preferably at least 15 of these modifications.

Very especially preferred embodiments of the synthetic phytase have one of the following cumulative sums of modifications relative to SEQ ID 24, with "PhV-[number]" not representing any mutation, but the number of the mutant for identifying the same.

| | |
|---|---|
| PhV-001 | D2E A4E A6S F8Y N33M K76N N78T D92N Q121T A123V T152G S164E A200N D258N S261H N270Q H374N D398E |
| PhV-002 | D2E A4E A6S F8Y N33M K76N N78T D92A Q121T A123V T152G S164E A200N D258N S261H N270Q H374N D398E |
| PhV-003 | D2E A4E A6S F8Y N33M R67L K76N N78T D92A Q121T A123V T152G S164E A200N D258N M260I S261H N270Q H374N D398E |
| PhV-004 | D2E A4E A6S F8Y N33M R67L K76N N78T D92N Q109N Q121T A123V A144E T152G Q159N S164E A200N S217G D258N M260I S261H N270Q H374N D398E |
| PhV-020 | S1-D2-T3Q A4G P5A A6D G7K F8M Q9K K12R N33M K76N N78T D92N Q121T T152G S164E A200N D258N S261H N270Q H374N |
| PhV-031 | D2E A4E A6S F8Y N33M K76N N78T D92N Q121T S164E A200N D258N S261H N270Q H374N |
| PhV-048 | S1- D2- T3Q A4G P5A A6D G7K F8M Q9K K12R N33M K76I N78T D92N Q121T T152G S164E A200N D258N S261H N270Q H374N |
| PhV-053 | S1- D2- T3Q A4G P5A A6D G7K F8M Q9K K12R N33M K76N N78T D92N Q121T A123 VT152G S164E A200N D258N S261H N270Q I300L H374N |
| PhV-055 | D2E A4E A6S F8Y N33M K76N N78T D92N Q121T T152G S164E A200N D258N S261H N270Q Q276N H374N |
| PhV-058 | D2E A4E A6S F8Y N33M K76N N78T D92N Q121T T152G S164E A200N D258N S261H N270Q H374N |
| PhV-059 | D2E A4E A6S F8Y N33M K76N N78T D92N Q121T T152G S164E A200N D258N S261H N270Q H374N D398E |
| PhV-060 | S1- D2- T3Q A4G P5A A6D G7K F8M Q9K K12R N33M K76N N78T D92N Q109N Q121T T152G S164E A200N D258N S261H N270Q I300L N346G H374N |
| PhV-064 | S1- D2- T3Q A4G P5A A6D G7K F8M Q9K K12R K76N N78T D92A Q121T S164E A200N D258N S261H N270Q H374N |
| PhV-065 | S1- D2- T3Q A4G PSA A6D G7K F8M Q9K K12R K76N N78T D92T Q121T S164E A200N D258N S261H N270Q H374N |
| PhV-066 | S1- D2- T3Q A4G P5A A6D G7K F8M Q9K K12R K76N N78T D92V Q121T S164E A200N D258N S261H N270Q H374N |
| PhV-067 | S1- D2- T3Q A4G P5A A6D G7K F8M Q9K K12R K76N N78T D92A Q121T A123V S164E A200N D258N S261H N270Q H374N |
| PhV-068 | S1- D2- T3Q A4G P5A A6D G7K F8M Q9K K12R K76N N78T D92E Q121T A123V S164E A200N D258N S261H N270Q H374N |
| PhV-069 | S1- D2- T3Q A4G P5A A6D G7K F8M Q9K K12R K76N N78T D92T Q121T A123V S164E A200N D258N S261H N270Q H374N |
| PhV-070 | S1- D2- T3Q A4G P5A A6D G7K F8M Q9K K12R K76N N78T D92V Q121T A123V S164E A200N D258N S261H N270Q H374N |
| PhV-071 | ASRNADKMK9 K12R K76N N78T D92N Q121T S164E A200N D258N S261H N270Q H374N |
| PhV-072 | S1- D2- T3Q A4G P5A A6D G7K F8M Q9K K12R K76N N78T D92E Q121T S164E A200N D258N S261H N270Q H374N |
| PhV-073 | S1- D2- T3Q A4G P5A A6D G7K F8M Q9K K12R K76I N78T D92N Q109N Q121T S164E A200N D258N S261H N270Q I300L H374N |
| PhV-074 | S1- D2- T3Q A4G P5A A6D G7K F8M Q9K K12R K76I N78T D92N Q109N Q121T S164E A200N D258N S261H N270Q I300L H374N D398E |
| PhV-075 | S1- D2- T3Q A4G P5A A6D G7K F8M Q9K K12R K76N N78T D92N Q109N Q121T A144E S164E A200N S217G D258N S261H N270Q I300L H374N |
| PhV-076 | S1- D2- T3Q A4G P5A A6D G7K F8M Q9K K12R K76N N78T D92A Q121T A123V S164E A200N D258N S261H N270Q I300L H374N |
| PhV-077 | S1- D2- T3Q A4G P5A A6D G7K F8M Q9K K12R K76N N78T D92E Q121T A123V S164E A200N D258N S261H N270Q I300L H374N |
| PhV-078 | S1- D2- T3Q A4G P5A A6D G7K F8M Q9K K12R K76N N78T D92T Q121T A123V S164E A200N D258N S261H N270Q I300L H374N |
| PhV-079 | S1- D2- T3Q A4G P5A A6D G7K F8M Q9K K12R K76N N78T D92V Q121T A123V S164E A200N D258N S261H N270Q I300L H374N |
| PhV-081 | D2E A4E A6S F8Y N33M K76N N78T D92N Q121T A123V T152G S164E A200N D258N S261H N270Q H374N D398E |
| PhV-083 | D2E A4E A6S F8Y N33M K76N N78T D92N Q121T T152G S164E A200N D258N S261H N270Q Q276N I300L H374N D398E |
| PhV-084 | S1- D2- T3Q A4G P5A A6D G7K F8M Q9K K12R K76N N78T D92A Q121T S136K S164E A200N D258N S261H N270Q H374N |
| PhV-085 | S1- D2- T3Q A4G P5A A6D G7K F8M Q9K K12R K76I N78T D92A Q109N Q121T S164E A200N D258N S261H N270Q I300L H374N |
| PhV-088 | D2E A4E A6S F8Y N33M K76N N78T D92N Q121T T152G T156G S164E A200N D258N S261H N270Q H374N D398E |
| PhV-089 | D2E A4E A6S F8Y N33M K76N N78T D92N Q121T T152G S164E A200N D258N S261H N270Q I300L H374N D398E |
| PhV-094 | S1- D2- T3Q A4G P5A A6D G7K F8M Q9K K12R N33M K76N N78T D92N Q109N Q121T A123V T152G T156G S164E A200N D258N S261H N270Q Q276N I300L N346G H374N |
| PhV-095 | S1- D2- T3Q A4G P5A A6D G7K F8M Q9K K12R N33M K76I N78T D92N Q121T A144E T152G S164E A200N S217G D258N S261H N270Q H374N D398E |

-continued

| | |
|---|---|
| PhV-096 | S1- D2- T3Q A4G P5A A6D G7K F8M Q9K K12R K76I N78T D92A Q121T A123V S164E A200N D258N S261H N270Q H374N |
| PhV-097 | S1- D2- T3Q A4G P5A A6D G7K F8M Q9K K12R K76N N78T D92A Q109N Q121T A123V Q159N S164E A200N D258N S261H N270Q H374N |
| PhV-098 | S1- D2- T3Q A4G P5A A6D G7K F8M Q9K K12R K76N N78T D92A Q121T S136K S164E A200N D258N S261H N270Q H374N |
| PhV-099 | D2E A4E A6S F8Y N33D K76N N78T D92N Q121T T152G S164E A200N D258N S261H N270Q H374N |
| PhV-101 | N33D K76N N78T D92N Q121T T152G S164E A200N H374N |
| PhV-103 | N33D D92N Q121T T152G S164E A200N D258N S261H N270Q H374N |
| PhV-104 | N33M K76N N78T D92N Q121T T152G S164E A200N D258N S261H N270Q H374N |
| PhV-105 | N33D D92N S164E A200N D258N S261H N270Q H374N |
| PhV-106 | N33D K76N N78T D92N Q121T T152G S164E A200N D258N S261H H374N |
| PhV-107 | N33D K76N N78T D92N Q121T S164E A200N D258N S261H N270Q H374N |
| PhV-108 | N33D D92N Q121T A123V A144E T152G S164E A200N S217G D258N S261H N270Q H374N |
| PhV-109 | N33D D92N Q121T A123V A144E T152G Q159N S164E A200N D258N S261H N270Q H374N |
| PhV-110 | N33D D92N Q121T T152G Q159N S164E A200N S217G D258N M260I S261H N270Q H374N |
| PhV-111 | N33D D92A Q121T T152G Q159N S164E A200N S217G D258N M260I S261H N270Q H374N |
| PhV-112 | S1- D2- T3Q A4G P5A N33D D92N Q121T T152G S164E A200N D258N S261H N270Q H374N |
| PhV-113 | S1- D2- T3Q A4G P5A N33D D92N Q121T T152G S164E A200N D258N S261H N270Q H374N |
| PhV-114 | A6D G7K F8M Q9K N33D D92N Q121T T152G S164E A200N D258N S261H N270Q H374N |
| PhV-115 | N33D D92A Q121T A123V A144E T152G Q159N S164E A200N S217G D258N M260I S261H N270Q H374N |
| PhV-116 | N33D D92N Q121T A123V A144E T152G Q159N S164E A200N S217G D258N M260I S261H N270Q H374N |
| PhV-117 | S1A D2S T3R A4N N33D D92N Q121T T152G S164E A200N D258N S261H N270Q H374N |
| PhV-118 | N33D D92N Q121T A123V A144E T152G S164E A200N S217G D258N M260I S261H N270Q H374N |
| PhV-119 | N33D D92N Q121T T152G S164E A200N D258N S261H N270Q H374N |
| PhV-120 | D2E A4E A6S F8Y N33M K76N N78T D92N Q121T T152G S164E A200N D258N S261H N270Q H374N |
| PhV-121 | S1- D2- T3Q A4G P5A A6D G7K F8M Q9K K12R N33M K76N N78T D92N Q121T T152G S164E A200N D258N S261H N270Q H374N |
| PhV-122 | N33M K76N N78T D92N Q121T T152G S164E A200N D258N S261H N270Q H374N |
| PhV-123 | D2E A4E A6S F8Y N33D D92N S164E A200N H374N |
| PhV-124 | D2E A4E A6S F8Y N33D K76N N78T D92N Q121T T152G S164E A200N D258N S261H H374N |
| PhV-125 | N33D D92A Q121T A123V T152G S164E A200N D258N S261H N270Q H374N |
| PhV-126 | N33D D92A Q121T A123V T152G S164E A200N D258N M260I S261H N270Q H374N |
| PhV-127 | N33D D92N Q121T A144E T152G Q159N S164E A200N S217G D258N M260I S261H N270Q H374N |
| PhV-128 | A4E A6S N33D D92N Q121T T152G S164E A200N D258N S261H N270Q H374N |
| PhV-129 | N33D R67L D92N Q121T A144E T152G Q159N S164E A200N S217G D258N M260I S261H N270Q H374N |
| PhV-130 | L16V N33D D92N Q121T A144E T152G Q159N S164E A200N S217G D258N M260I S261H N270Q H374N |
| PhV-131 | K12R N33D D92N Q121T A144E T152G Q159N S164E A200N S217G D258N M260I S261H N270Q H374N |
| PhV-132 | K12R L16V N33D D92N Q121T A144E T152G Q159N S164E A200N S217G D258N M260I S261H N270Q H374N |
| PhV-133 | N33D R67L D92N Q121T A123V T152G Q159N S164E A200N S217G D258N M260I S261H N270Q H374N |
| PhV-134 | N33D D92N Q121T A144E T152G Q159N S164E A166E A200N S217G D258N M260I S261H N270Q H374N |
| PhV-135 | N33D R67L D92N Q121T A123V A144E T152G Q159N S164E A166E A200N S217G D258N M260I S261H N270Q H374N |
| PhV-136 | N33D D92A Q121T A123V A144E T152G Q159N S164E A166E A200N S217G D258N M260I S261H N270Q H374N |
| PhV-137 | N33D D92A Q121T T152G Q159N S164E A166E A200N S217G D258N M260I S261H N270Q H374N D398E |
| PhV-138 | N33D D92N Q121T A123V A144E T152G Q159N S164E A166E A200N S217G D258N M260I S261H N270Q H374N D398E |
| PhV-139 | N33D D92N Q121T A144E T152G Q159N S164E A200N S217G D258N S261H N270Q H374N |
| PhV-140 | K12R N33D R67L D92N Q121T A123V A144E T152G S164E A200N S217G D258N S261H N270Q H374N |
| PhV-141 | L16V N33D R67L D92N Q121T A123V A144E T152G S164E A200N S217G D258N S261H N270Q H374N |

-continued

| | |
|---|---|
| PhV-142 | N33D R67L D92N Q121T A123V A144E T152G S164E A166E A200N S217G D258N S261H N270Q H374N |
| PhV-143 | N33D D92N Q121T A123V A144E T152G S164E A166E A200N S217G D258N S261H N270Q I300L H374N |
| PhV-144 | N33D D92N I120L Q121T A123V A144E T152G S164E A200N S217G D258N S261H N270Q I300L H374N |
| PhV-145 | N33D D92N I120L Q121T A123V A144E T152G S164E A200N S217G D258N S261H N270Q L371A H374N |
| PhV-146 | N33D R67L D92N I120L Q121T A123V A144E T152G S164E A166E A200N S217G D258N S261H N270Q L371A H374N or |
| PhV-147 | N33D D92N I120L Q121T A123V A144E T152G S164E A200N S217G D258N S261H N270Q I300L L371AH374N. |

These especially preferred cumulative mutations of the synthetic phytases give in each case an increase in the thermostability to at least 83° C. Thus, these especially preferred embodiments result in thermostabilities of at least 18° C. above the 65° C. of the wild-type phytase from *Hafnia* sp LU11047. The pH profile of the thermostabilty of some phytases according to the invention is shown in each case in FIGS. 1 and 2A, B.

In one embodiment, the synthetic phytase has at least one conservative amino acid exchange at the positions mentioned compared with one of the above-described phytases, it being possible for the synthetic phytase to have at least one of the abovementioned individual modifications or one of the abovementioned groups of modifications. For the purposes of the present invention, conservative means an exchange of the amino acid G to A; A to G, S; V to I,L,A,T,S; I to V,L,M; L to I,M,V; M to L,I,V; P to A,S,N; F to Y,W,H; Y to F,W,H; W to Y,F,H; R to K,E,D; K to R,E,D; H to Q,N,S; D to N,E,K,R,Q; E to Q,D,K,R,N; S to T,A; T to S,V,A; C to S,T,A; N to D,Q,H,S; Q to E,N,H,K,R. Here, it is possible to combine any conservative exchange of an amino acid with any conservative exchange of another amino acid.

Advantageously, the synthetic phytase is an isolated phytase. It is also feasible that the synthetic phytase is present not as a purified isolated phytase, but as a fermentation liquor, with the biomass being separated off fully, partially or not at all. Here, the liquor can be concentrated or dried fully by removing liquid. It is possible to employ these unpurified or partially purified phytase solutions or phytase solids as additive in different products.

The synthetic phytase according to the invention advantageously has an elevated thermostability, an elevated stability to pepsin and/or an elevated specific activity compared with the two wild-type phytases from the organisms *Yersinia mollaretii* and *Hafnia* sp., which were the basis of the construction according to the synthetic phytase construct according to SEQ ID 24.

In a particular embodiment, the phytase according to the invention is unmodified at positions R18, H19, G20, R22, P24 and H306, D307 over SEQ ID 24 in respect of the type of amino acid and the position of this amino acid.

The invention also comprises an isolated nucleic acid sequence coding for a phytase with an amino acid sequence with at least 90%, preferably 95% and in particular 96, 97, 98 or 99%, identity to the amino acid sequence of SEQ ID 24.

In a particular embodiment, the invention comprises the above-described isolated nucleotide sequences according to the invention, with nucleotide sequences coding for phytases with the amino acid sequences from the group consisting of SEQ ID 18 and the mutants as described in Table 6 being excepted.

In a particular embodiment, the invention comprises an isolated nucleic acid sequence coding for a phytase, wherein it codes for one of the phytases according to the invention with the exception of phytases with the amino acid sequence SEQ ID 18 and its mutants as described in table 6.

The invention furthermore comprises a recombinant expression vector comprising one of the nucleic acid sequences according to the invention.

The invention likewise comprises a recombinant host cell comprising one of the nucleic acids according to the invention or comprising the recombinant expression vector according to the invention.

The object is furthermore achieved by a recombinant production organism, which is a nonhuman production organism which comprises one of the nucleic acid sequences according to the invention or which comprises the recombinant expression vector according to the invention. The recombinant production organism is especially preferably one from the genus *Aspergillus, Pichia, Trichoderma, Hansenula, Saccharomyces, Bacillus, Escherischia, Kluyveromyces, Schizosaccharomyces*.

The object is furthermore achieved by an animal feed additive which comprises at least one of the phytases according to the invention and further customary feed additives, for example for cattle, poultry or pigs, such as, for example, vitamins, minerals or other additives.

The object is furthermore achieved by an animal feed which comprises at least one of the described synthetic phytases according to the invention, together with customary feed components. Feasible feed components in this context are all those which are conventionally employed in feed pellets for beef, dairy cow, poultry or pig fattening.

The object is furthermore achieved by the use of one of the described synthetic phytases according to the invention or of the animal feed additive according to the invention comprising at least one of the synthetic phytases according to the invention in an animal feed. In this context, the use may take place in the form of the addition of the phytase according to the invention or of the animal feed additive according to the invention before the pelleting of the remaining feed components. It is also feasible to apply the phytase to these pellets after the preparation of feed pellets, in particular in liquid form.

The invention is furthermore achieved by the use of one of the above-described synthetic phytases according to the invention, of the animal feed additive according to the invention, which comprises at least one of the synthetic phytases according to the invention or of the animal feed which comprises at least one of the described synthetic phytases, for reducing the phosphate content in the slurry of livestock.

The invention is furthermore solved by the use of one of the above-described synthetic phytases according to the invention, of the animal feed additive according to the invention which comprises at least one of the synthetic phytases according to the invention, or the animal feed which comprises at least one of the synthetic phytases described, for reducing the phosphate content in the slurry of livestock.

The disclaimer (page 3, lines 28-30) relating to phytases with the amino acid sequences of the group consisting of SEQ ID 18 and the mutants as described in table 6 is herewith by reference made subject matter of all special embodiments of the invention.

The embodiments described are intended to illustrate and to give a better understanding of the invention and are in no way to be construed as limiting. Further features of the invention result from the description hereinbelow of preferred embodiments in conjunction with the dependent claims. In this context, the individual features of the invention may, in one embodiment, be realized in each case individually or together and are no limitation whatsoever of the invention to the described embodiment. The wording of the patent claims is hereby expressly made subject matter of the description.

EXAMPLES

Figure 1:
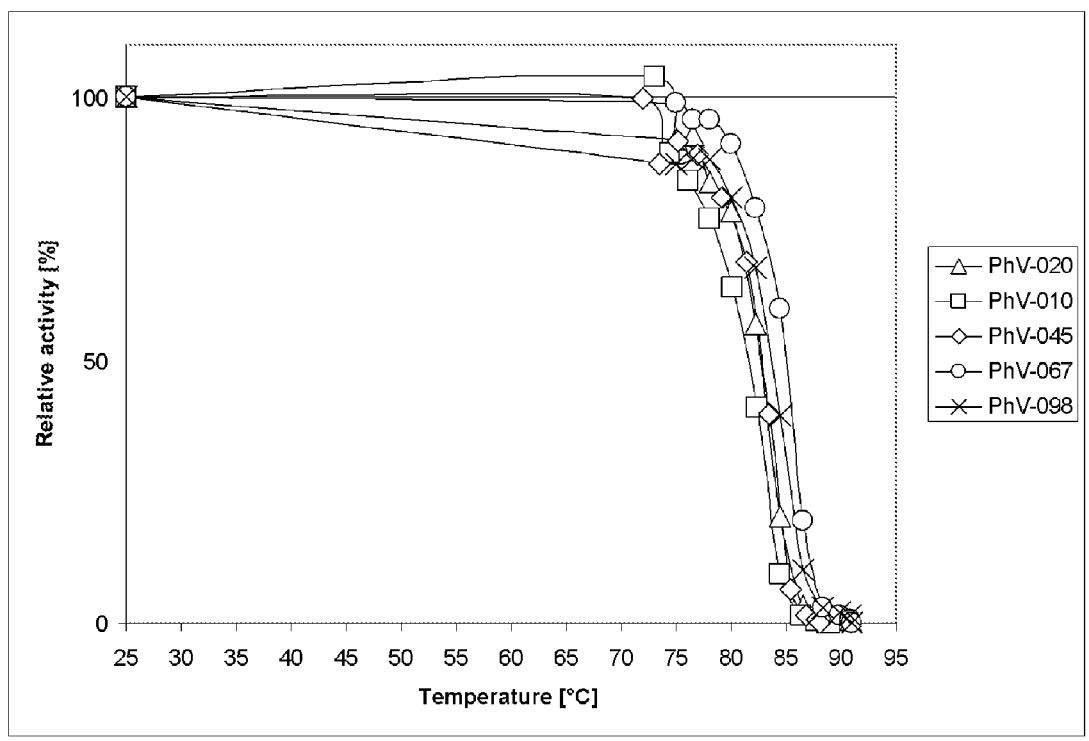
FIG. 1 shows the thermostability of the phytases PhV-020, PhV-010, PhV-045, PhV-067, PhV-098 according to the invention. The phytases are heated for 20 min at pH 5.5 at the temperature stated. After cooling, the residual activity at pH 5.5 and 37° C. is determined. To determine the relative residual activity, the activity of a reference sample incubated for 20 min at room temperature is set at 100%.

Cloning the Phytase from *Hafnia* sp. LU11047

Phytases are searched for in a series of *enterobacteria* analogously to the publications Huang et al. (2006) A novel phytase with preferable characteristics from *Yersinia intermedia*. Biochem Biophys Res Commun 350: 884-889, Shi et al. (2008) A novel phytase gene appA from *Buttiauxella* sp. GC21 isolated from grass carp intestine. Aquaculture 275:70-75 and WO2008116878 (Example 1) with the aid of the degenerate oligos Haf1090 5'-GAYCCNYTNTTYCAYCC-3' (SEQ ID 1) and Haf1092 5'-GGNGTRTTRTCNGGYTG-3' (SEQ ID 2) at annealing temperatures of between 40° C. and 50° C., using PCR. The PCR products formed are employed as template for a semi-nested PCR using the oligos Haf1090 5'-GAYCCNYTNTTYCAYCC-3' (SEQ ID 1) and Haf1091 5'-GCDATRTTNGTRTCRTG-3' (SEQ ID 3) under identical annealing conditions. A fragment can be isolated from a bacterial strain of the genus *Hafnia* (*Hafnia* sp. LU11047). The isolated fragment is subcloned with the aid of the "TOPO TA Cloning® Kit" (Invitrogen) following the manufacturer's instructions and subsequently sequenced. Starting from this part-sequence, the full-length sequence of the phytase is amplified via the so-called TAIL-PCR method (Yao-Guang Liu and Robert F. Whittier (1995) Thermal asymmetric interlaced PCR: automatable amplification and sequencing of insert end fragments from P1 and YAC clones for chromosome walking. Genomics 25, 674-681). The following oligonucleotides are used for this purpose:

| Amplification of the 3' end: |
| --- |
| 1. Haf1165 (5'-WCAGNTGWTNGTNCTG-3', SEQ ID 4) and Haf1167 (5'-CTTCGAGAGCCACTTTATTACCGTCG-3', SEQ ID 5) |
| 2. Haf1165 (5'-WCAGNTGWTNGTNCTG-3', SEQ ID 4) and Haf1168 (5'-CCAATGTTGTGCTGCTGACAATAGG-3', SEQ ID 6) |
| 3. Haf1165 (5'-WCAGNTGWTNGTNCTG-3', SEQ ID 4) and Haf1169 (5'-CCGAACTCATCAGCGCTAAAGATGC-3', SEQ ID 7) |
| Amplification of the 5' end: |
| 1. Haf1077 (5'-CAWCGWCNGASASGAA-3', SEQ ID 8) and Haf1170 (5'-CGCAGTTTGACTTGATGTCGCGCACG-3', SEQ ID 9) |
| 2. Haf1077 (5'-CAWCGWCNGASASGAA-3', SEQ ID 8) and Haf1171 (5'-GTCGCGCACGCCCTATATCGCCAAGC-3', SEQ ID 10) |
| 3. Haf1077 (5'-CAWCGWCNGASASGAA-3', SEQ ID 8) and Haf1172 (5'- CTGCAAACCATCGCACACGCACTGG-3', SEQ ID 11) |

The DNA fragments obtained are cloned with the aid of the "TOPO TA Cloning® Kit" (Invitrogen) and sequenced. The nucleotide sequences give the gene SEQ ID 12, which codes for the *Hafnia* sp. LU11047 phytase. The amino acid sequence SEQ ID 13, which is derived therefrom, has 98% identity with the phytase sequence of a *Hafnia alvei* phytase from WO200811678. Using the software Signal 2.0, the amino acids 1-33 are predicted to be a signal peptide. The mature enzyme, accordingly, starts with the serine in position 34.

1. Synthetic Phytase Fus5#2

Cloning the Phytase Fus5#2

Starting from the chromosomal DNA from *Hafnia* sp. LU11047, a fragment of base 1-1074 of the phytase (SEQ ID 14) is amplified by means of PCR. Oligonucleotides are derived from the DNA sequence of a putative phytase (or acidic phosphatase) from *Yersinia mollaretii* ATCC43969, NCBI Sequenz ID ZP_00824387 for amplifying the nucleotides 1057-1323. This is used to amplify a second phytase fragment from the chromosomal DNA from *Yersinia mollaretii* ATCC 43969 (SEQ ID 15). Upon amplification of the two phytase fragments, an overlap of 20 bp to the respective other phytase fragment is generated, with the aid of the oligos used, both at the 3' end of the *Hafnia* fragment and at the 5' end of the *Yersinia* fragment. In this manner, the two fragments can be combined via PCR fusion to give the phytase sequence SEQ ID 16, which codes for the synthetic phytase Fus5#2. For the amino acid sequence SEQ ID 17 derived therefrom, the amino acids 1-33 are predicted by the software SignalP 2.0 to be a signal peptide. The mature phytase Fus5#2 (SEQ ID 18) is encoded by the nucleotide sequence SEQ ID 19.

To clone an expression plasmid for *E. coli*, an NdeI restriction cleavage site is generated at the 5' end of the phytase DNA fragment SEQ ID 16 and a HindIII restriction cleavage site and a stop codon are generated at the 3' end. The sequences additionally required for this are introduced by means of a PCR reaction via the primers used, with the aid of the phytase SEQ ID 16 as the template. Using these cleavage sites, the phytase-encoding gene is cloned into the E. coli expression vector pET22b (Novagen). By using the NdeI restriction cleavage site and by introducing the stop codon, the pelB signal sequence is removed from the vector and read-through into the 6× His tag, which is present on the plasmid, is prevented. The plasmid pFus5#2 (SEQ ID 20) thus generated is transformed into the E. coli strain BL21 (DE3) (Invitrogen). For the improved purification of the phytase protein, a phytase variant with an N-terminal 6× His tag is cloned. Using the sense oligo primerH6: 5'-ctatggatc-cgcatcatcatcatcatcacagtgataccgcccctgc-3' (SEQ ID 21), which introduces not only the 6× His tag, but also a BamHI cleavage site, and which acts as a template for the sequence SEQ ID 19, which codes for the mature phytase protein, a PCR product is amplified. At the 3' end of the PCR product, a stop codon and an NdeI restriction cleavage site are, again, introduced using the same antisense oligo. The fragment thus generated is cloned into the vector pET22b via BamHI/NdeI, giving rise to the plasmid pH6-Fus5#2 (SEQ ID 22), which is likewise transformed into E. coli BL21(DE3). In the case of this construct, the pelB signal sequence, which is comprised in pET22b, is used for the transport into the periplasma.

Phytase Assay

The phytase activity is determined in microtiter plates. The enzyme sample is diluted in reaction buffer (250 mM Na acetate, 1 mM $CaCl_2$, 0.01% Tween 20, pH 5.5). 10 µl of the enzyme solution are incubated with 140 µl substrate solution (6 mM Na phytate (Sigma P3168) in reaction buffer) for 1 h at 37° C. The reaction is quenched by adding 150 µl of trichloroacetic acid solution (15% w/w). To detect the liberated phosphate, 20 µl of the quenched reaction solution are treated with 280 µl of freshly made-up color reagent (60 mM L-ascorbic acid (Sigma A7506), 2.2 mM ammonium molybdate tetrahydrate, 325 mM $H_2SO_4$), and incubated for 25 min at 50° C., and the absorption at 820 nm was subsequently determined. For the blank value, the substrate buffer on its own is incubated at 37° C. and the 10 µl of enzyme sample are only added after quenching with trichloroacetic acid. The color reaction is performed analogously to the remaining measurements. The amount of liberated phosphate is determined via a calibration curve of the color reaction with a phosphate solution of known concentration.

Expression in *Escherichia coli*

The E. coli BL21(DE3) strains, which harbor a plasmid with a phytase expression cassette, are grown at 37° C. in LB medium supplemented with ampicillin (100 mg/l). The phytase expression is induced at an OD (600 nm) of 0.6 by adding 1 mM IPTG. After 4 h of induction, 10% (v/v) of a 10× BugBuster solution (Novogen) is added and the mixture is incubated for 15 min at room temperature. After the centrifugation, the supernatant is used for determining the phytase activity.

Purification via Ni Affinity Chromatography

To purify the 6× His-labeled phytase variants, an induced, phytase-expressing E. coli culture broth is treated with 300 mM NaCl, Complete™ Protease Inhibitor without EDTA (following the instructions of the manufacturer Roche Applied Science) and with 10% (v/v) of a 10× BugBuster solution (Novogen), and the mixture is incubated for 15 min at room temperature. After the centrifugation, the supernatant is bound to Ni-NTA columns/KIT (Qiagen) following the manufacturer's instructions. The elution after the wash steps is performed using cold elution buffer (50 mM Na acetate buffer, 300 mM NaCl, 500 mM imidazole, 1 mM $CaCl_2$).

Before determining the protein content, the sample is subjected to a buffer exchange for 2 mM sodium citrate pH 5.5 by dialysis.

Expression in *Aspergillus niger*

To express the phytase Fus5#2 in *Aspergillus niger*, an expression construct is first prepared which comprises the phytase gene under the control of the A. niger glucoamylase (glaA) promoter, flanked by the noncoding 3'-glaA region. In this manner, the construct is intended for integration into the 3'-glaA region in A. niger. The signal sequence used for the extracellular protein secretion is the signal sequence of the A. ficuum phytase. The base used for the expression construct is the Plasmid pGBGLA-53 (also referred to as pGBTOPFYT-1 in WO9846772), which is described in detail in EP0635574B1. With the aid of PCR-based cloning techniques known to a person skilled in the art, the gene segment of the A. ficuum phytase, which codes for the mature phytase protein starting with the amino acid sequence ASRNQSS, in pGBGLA-53 is replaced by the gene segment SEQ ID 19, which codes for the mature Fus5#2 phytase. This gives rise to the resulting plasmid pGLA53-Fus5#2 (SEQ ID 23). The cotransformation of the linear expression cassette, isolated from the resulting plasmid using HindIII, together with an amdS marker cassette, isolated from the plasmid pGBLA50 (EP0635574B1)/pGBAAS-1 (name of the same plasmid in WO9846772), into a glaA-deleted A. niger expression strain and the subsequent expression of the phytase in shake flasks is performed as described in the two cited patent specifications. The phytase activity in the culture supernatant is determined daily after the cells have been centrifuged off. The maximum activity is achieved between day 3 and day 6.

2. Phytase Variants of Phytase Fus5#2

Variants of the phytase are generated by mutating the gene sequence SEQ ID 19 by means of PCR. The "Quickchange Site-directed Mutagenesis Kit" (Stratagene) is used to carry out a directed mutagenesis. A random mutagenesis over the entire coding sequence, or else only part thereof, of SEQ ID 19 is performed with the aid of the "GeneMorph II Random Mutagenesis Kit" (Stratagene). The mutagenesis rate is set to the desired amount of 1-5 mutations via the amount of the template DNA used. Multiple mutations are generated by the targeted combination of individual mutations or by the sequential performance of several mutagenesis cycles.

The phytase variants generated are tested for phytase activity and temperature stability in an assay with high-throughput capability. To this end, the E. coli BL21(DE3) clones obtained after the transformation with the pET22b-based expression construct are incubated (30° C., 900 rpm, shaker excursion 2 mm) in 96-well microtiter plates in LB Medium (2% glucose, 100 mg/l ampicillin). Induction is carried out with 1 mM IPTG for 4 h at an OD (600 nm) of approximately 0.5. Thereafter, 10% (v/v) of a 10× BugBuster solution (Novogen) is then added and the mixture is incubated for 15 min at room temperature. The phytase activity and the residual activity after 20 minutes of temperature stress are determined.

The term SEQ ID 24 refers to the phytase variant which differs from SEQ ID 18 by the following mutations: A89T D138N A142T H143Y N202S K207E A209Q H228Y K234V T242N Q244S D247K K251N Q256H T277A A279S H280N G283N S284P I286A A287T S288E R289S P290K S314G T320N F356I H413Q. All further mutants (see table 1) are considered as being based on SEQ ID 24 and are characterized with reference to the modifications based on the amino acid sequence positions of SEQ ID 24. These phytase variants are cloned into the E. coli expression vector pET22b (Novagen) analogously to the procedures described in the previous section and subsequently expressed with the aid of the *E. coli* strain BL21(DE3). In addition, suitable expression constructs for *Aspergillus niger* are cloned so that the phytase can be expressed after transformation into *A. niger*.

Determination of the Thermostability (T50)

To record the thermal inactivation curve, the enzyme sample which is diluted in reaction buffer (250 mM Na acetate, 1 mM $CaCl_2$, 0.01% Tween 20, pH 5.5) is heated for 20 min at the respective temperatures and thereafter cooled to 4° C. A reference sample which has not undergone thermal treatment is left at room temperature for 20 min and is then likewise cooled to 4° C. After the thermal pretreatment, the enzyme activity of the samples is determined by means of the phytase assay. The activity of the reference sample is normalized to 100%. The thermostability of the various phytase variants is characterized by what is known as the T50 value. The T50 indicates the temperature at which 50% residual activity is still present after thermal inactivation, compared with a reference sample which has not undergone thermal treatment. Changes in the thermostability of two phytase variants, expressed in ° C., result from the difference of the respective $T_{50}$ values.

TABLE 1

Thermostability ($T_{50}$) of the phytase variants in ° C. (see also FIG. 1). Changes over SEQ ID 24 are specified at individual amino acid exchanges in the form [original amino acid][position][new amino acid]. The symbol "—" in this case indicates a deletion of the amino acid in question. The numbering of the amino acid position always refers to SEQ ID 24.

| Mutant | Mutation | $T_{50}$ [° C.] |
|---|---|---|
| PhV-001 | D2E A4E A6S F8Y N33M K76N N78T D92N Q121T A123V T152G S164E A200N D258N S261H N270Q H374N D398E | 84 |
| PhV-002 | D2E A4E A6S F8Y N33M K76N N78T D92A Q121T A123V T152G S164E A200N D258N S261H N270Q H374N D398E | 85 |
| PhV-003 | D2E A4E A6S F8Y N33M R67L K76N N78T D92A Q121T A123V T152G S164E A200N D258N M260I S261H N270Q H374N D398E | 85 |
| PhV-004 | D2E A4E A6S F8Y N33M R67L K76N N78T D92N Q109N Q121T A123V A144E T152G Q159N S164E A200N S217G D258N M260I S261H N270Q H374N D398E | 85 |
| PhV-005 | P75N D77T D92N Q121T S164E A200N D258N S261H N270Q H374N | 81 |
| PhV-006 | Q71E D92N S164E A200N D258N S261H N270Q H374N | 81 |
| PhV-007 | S1- D2- T3Q A4G P5A A6D G7K F8M Q9K K12R K76N N78T D92N Q121T S164E A200N D258N S261H N270Q H374N | 81 |
| PhV-008 | D92N S136K S164E A200N D258N S261H N270Q H374N Q406K | 81 |
| PhV-009 | S1- D2- T3Q A4G P5A A6D G7K F8M Q9K K12R N33M H37Y K76N N78T D92N Q121T S164E A200N D258N S261H N270Q H374N | 81 |
| PhV-010 | S1- D2- T3Q A4G P5A A6D G7K F8M Q9K K12R N33M K76N N78T D92N Q121T S164E A200N D258N S261H N270Q H374N | 82 |
| PhV-011 | S1- D2- T3Q A4G P5A A6D G7K F8M Q9K K12R N33M H37Y P75N D77T D92N Q121T S164E A200N D258N S261H N270Q H374N | 81 |
| PhV-012 | S1- D2- T3Q A4G P5A A6D G7K F8M Q9K K12R K76N N78T D92N Q121T S164E A200N D258N S261H N270Q H374N D398E | 82 |
| PhV-013 | S1- D2- T3Q A4G P5A A6D G7K F8M Q9K K12R K76N N78T D92N Q121T S164E A200N D258N S261H N270Q H374N D398K | 81 |
| PhV-014 | S1- D2- T3Q A4G P5A A6D G7K F8M Q9K K12R K76N N78T D92N Q121T S164E A200N D258N S261H N270Q H374N D398G | 81 |
| PhV-015 | S1- D2- T3Q A4G P5A A6D G7K F8M Q9K K12R K76N N78T D92N Q109E Q121T S164E A200N D258N S261H N270Q H374N | 81 |
| PhV-016 | S1- D2- T3Q A4G P5A A6D G7K F8M Q9K K12R K76N N78T D92N Q109N Q121T S164E A200N D258N S261H N270Q H374N | 81 |
| PhV-017 | S1- D2- T3Q A4G P5A A6D G7K F8M Q9K K12R K76N N78T D92N Q121T Q159N S164E A200N D258N S261H N270Q H374N | 82 |
| PhV-018 | S1- D2- T3Q A4G P5A A6D G7K F8M Q9K K12R K76N N78T D92N Q121T S164E A200N D258N S261H N270Q T322Q H374N | 81 |
| PhV-019 | S1- D2- T3Q A4G P5A A6D G7K F8M Q9K K12R N33M K76N N78T D92N Q121T T152A S164E A200N D258N S261H N270Q H374N | 82 |
| PhV-020 | S1- D2- T3Q A4G P5A A6D G7K F8M Q9K K12R N33M K76N N78T D92N Q121T T152G S164E A200N D258N S261H N270Q H374N | 83 |
| PhV-021 | S1- D2- T3Q A4G P5A A6D G7K F8M Q9K K12R N33M D92N Q121T S164E A200N D258N S261H N270Q H374N | 82 |
| PhV-022 | S1- D2- T3Q A4G P5A A6D G7K F8M Q9K K12R K76N N78T D92N Q121T T152G S164E A200N D258N S261H N270Q H374N | 82 |
| PhV-023 | S1- D2- T3Q A4G P5A A6D G7K F8M Q9K K12R K76N N78T D92N Q121T S164E A200N D258N S261H N270Q I300L H374N | 82 |
| PhV-024 | S1- D2- T3Q A4G P5A A6D G7K F8M Q9K K12R N33M K76N N78T D92N Q121T S136K Q141K S164E A200N D258N S261H N270Q H374N | 82 |
| PhV-025 | S1- D2- T3Q A4G P5A A6D G7K F8M Q9K K12R N33M K76N N78T D92N Q121T S136K S164E A200N D258N S261H N270Q H374N | 81 |
| PhV-026 | S1- D2- T3Q A4G P5A A6D G7K F8M Q9K K12R N33M K76N 77SQD79 D92N Q121T S164E A200N D258N S261H N270Q H374N | 82 |
| PhV-027 | S1- D2- T3Q A4G P5A A6D G7K F8M Q9K K12R N33M K76N 77SQG79 D92N Q121T S164E A200N D258N S261H N270Q H374N | 81 |
| PhV-028 | S1- D2- T3Q A4G P5A A6D G7K F8M Q9K K12R N33M K76N N78T D92N Q121T S136K S164E A166E A200N D258N S261H N270Q H374N | 81 |

TABLE 1-continued

Thermostability ($T_{50}$) of the phytase variants in °C. (see also FIG. 1). Changes over SEQ ID 24 are specified at individual amino acid exchanges in the form [original amino acid][position][new amino acid]. The symbol "—" in this case indicates a deletion of the amino acid in question. The numbering of the amino acid position always refers to SEQ ID 24.

| Mutant | Mutation | $T_{50}$ [°C.] |
|---|---|---|
| PhV-029 | S1- D2- T3Q A4G P5A A6D G7K F8M Q9K K12R N33M K76N N78T D92N Q121T S136K S164E A166H A200N D258N S261H N270Q H374N | 81 |
| PhV-030 | S1- D2- T3Q A4G P5A A6D G7K F8M Q9K K12R N33M K76N N78T D92N Q121T S136K S164E A200N S217G D258N S261H N270Q H374N | 82 |
| PhV-031 | D2E A4E A6S F8Y N33M K76N N78T D92N Q121T S164E A200N D258N S261H N270Q H374N | 83 |
| PhV-032 | S1- D2- T3Q A4G P5A A6D G7K F8M Q9K K12R N33M K76N N78T D92N Q121T N159K S164E A200N D258N S261H N270Q H374N | 81 |
| PhV-033 | S1- D2- T3Q A4G P5A A6D G7K F8M Q9K K12R N33M K76N N78T D92N Q121T S164E A200N D258N S261H N270Q H374N Q406K | 81 |
| PhV-034 | S1- D2- T3Q A4G P5A A6D G7K F8M Q9K K12R K76N N78T D92N Q121T A123V S164E A200N D258N S261H N270Q H374N | 81 |
| PhV-035 | S1- D2- T3Q A4G P5A A6D G7K F8M Q9K K12R K76N N78T D92N Q121T A123V S164E A200N D258N S261H N270Q I300L H374N | 81 |
| PhV-036 | S1- D2- T3Q A4G P5A A6D G7K F8M Q9K K12R N33M K76N N78T D92N Q121T A144E S164E A166E A200N D258N S261H N270Q H374N | 82 |
| PhV-037 | S1- D2- T3Q A4G P5A A6D G7K F8M Q9K K12R N33M K76N N78T D92N Q121T A144E S164E A166H A200N D258N S261H N270Q H374N | 82 |
| PhV-038 | S1- D2- T3Q A4G P5A A6D G7K F8M Q9K K12R N33M K76N N78T D92N Q121T A144E S164E A200N S217G D258N S261H N270Q H374N | 82 |
| PhV-039 | S1- D2- T3Q A4G P5A A6D G7K F8M Q9K K12R N33M K76N N78T D92N Q121T S164E A166H A200N D258N S261H N270Q H374N D398E | 82 |
| PhV-040 | S1- D2- T3Q A4G P5A A6D G7K F8M Q9K K12R N33M K76N N78T D92N Q121T S164E A200N S217G D258N S261H N270Q H374N D398E | 82 |
| PhV-041 | S1- D2- T3Q A4G P5A A6D G7K F8M Q9K K12R N33M K76N N78T D92N Q121T S136K S164E A200N D258N S261H N270Q H374N D398E | 82 |
| PhV-042 | S1- D2- T3Q A4G P5A A6D G7K F8M Q9K K12R N33M K76N N78T D92N Q121T S136K S164E Q193L A200N D258N S261H N270Q H374N | 82 |
| PhV-043 | S1- D2- T3Q A4G P5A A6D G7K F8M Q9K K12R N33M K76N N78T D92N N119A Q121T S164E A200N D258N S261H N270Q H374N | 81 |
| PhV-044 | S1- D2- T3Q A4G P5A A6D G7K F8M Q9K K12R N33M K76N N78T D92N N119T Q121T S164E A200N D258N S261H N270Q H374N | 81 |
| PhV-045 | S1- D2- T3Q A4G P5A A6D G7K F8M Q9K K12R N33M K76N N78T D92N Q109N Q121T T152G S164E A200N D258N S261H N270Q I300L H374N | 83 |
| PhV-046 | S1- D2- T3Q A4G P5A A6D G7K F8M Q9K K12R N33M K76N N78T D92N Q109N Q121T T152G S164E A200N D258N S261H K268N N270Q I300L H374N | 81 |
| PhV-047 | S1- D2- T3Q A4G P5A A6D G7K F8M Q9K K12R N33M K76N N78T D92N Q109N Q121T S164E A200N D258N S261H K268N N270Q I300L H374N | 81 |
| PhV-048 | S1- D2- T3Q A4G P5A A6D G7K F8M Q9K K12R N33M K76I N78T D92N Q121T T152G S164E A200N D258N S261H N270Q H374N | 83 |
| PhV-049 | S1- D2- T3Q A4G P5A A6D G7K F8M Q9K K12R N33M K76R N78T D92N Q121T T152G S164E A200N D258N S261H N270Q H374N | 82 |
| PhV-050 | S1- D2- T3Q A4G P5A A6D G7K F8M Q9K K12R N33M K76D N78T D92N Q121T T152G S164E A200N D258N S261H N270Q H374N | 82 |
| PhV-051 | S1- D2- T3Q A4G P5A A6D G7K F8M Q9K K12R N33M K76N N78T D92N Q118S Q121T S164E A200N D258N S261H N270Q H374N | 82 |
| PhV-052 | S1- D2- T3Q A4G P5A A6D G7K F8M Q9K K12R N33M K76N N78T D92N Q118S N119A Q121T S164E A200N D258N S261H N270Q H374N | 81 |
| PhV-053 | S1- D2- T3Q A4G P5A A6D G7K F8M Q9K K12R N33M K76N N78T D92N Q121T A123V T152G S164E A200N D258N S261H N270Q I300L H374N | 83 |
| PhV-054 | S1- D2- T3Q A4G P5A A6D G7K F8M Q9K K12R N33M K76N N78T D92N Q118S N119A Q121T T152G S164E A200N D258N S261H N270Q H374N | 82 |
| PhV-055 | D2E A4E A6S F8Y N33M K76N N78T D92N Q121T T152G S164E A200N D258N S261H N270Q Q276N H374N | 83 |
| PhV-056 | D2E A4E A6S F8Y N33M K76N N78T D92N Q121T S164E A200N D258N S261H N270Q Q276N N346G H374N | 82 |

TABLE 1-continued

Thermostability ($T_{50}$) of the phytase variants in °C. (see also FIG. 1). Changes over SEQ ID 24 are specified at individual amino acid exchanges in the form [original amino acid][position][new amino acid]. The symbol "—" in this case indicates a deletion of the amino acid in question. The numbering of the amino acid position always refers to SEQ ID 24.

| Mutant | Mutation | $T_{50}$ [°C.] |
|---|---|---|
| PhV-057 | S1- D2- T3Q A4G P5A A6D G7K F8M Q9K K12R N33M K76N N78T D92N Q109N Q121T T152G S164E A200N D258N S261H N270Q Q276N I300L N346G H374N | 82 |
| PhV-058 | D2E A4E A6S F8Y N33M K76N N78T D92N Q121T T152G S164E A200N D258N S261H N270Q H374N | 83 |
| PhV-059 | D2E A4E A6S F8Y N33M K76N N78T D92N Q121T T152G S164E A200N D258N S261H N270Q H374N D398E | 83 |
| PhV-060 | S1- D2- T3Q A4G P5A A6D G7K F8M Q9K K12R N33M K76N N78T D92N Q109N Q121T T152G S164E A200N D258N S261H N270Q I300L N346G H374N | 83 |
| PhV-061 | S1- D2- T3Q A4G P5A A6D G7K F8M Q9K K12R N33M K76N N78T D92N Q121T E155N S164E A200N D258N S261H N270Q D345G H374N | 81 |
| PhV-062 | S1- D2- T3Q A4G P5A A6D G7K F8M Q9K K12R N33M K76N N78T D92N Q121T A123V S136K T152G S164E A200N D258N S261H N270Q H374N | 82 |
| PhV-063 | S1- D2- T3Q A4G P5A A6D G7K F8M Q9K K12R K76N N78T D92N Q121T E155N S164E A200N D258N S261H N270Q Q276N H374N | 82 |
| PhV-064 | S1- D2- T3Q A4G P5A A6D G7K F8M Q9K K12R K76N N78T D92A Q121T S164E A200N D258N S261H N270Q H374N | 84 |
| PhV-065 | S1- D2- T3Q A4G P5A A6D G7K F8M Q9K K12R K76N N78T D92T Q121T S164E A200N D258N S261H N270Q H374N | 83 |
| PhV-066 | S1- D2- T3Q A4G P5A A6D G7K F8M Q9K K12R K76N N78T D92V Q121T S164E A200N D258N S261H N270Q H374N | 83 |
| PhV-067 | S1- D2- T3Q A4G P5A A6D G7K F8M Q9K K12R K76N N78T D92A Q121T A123V S164E A200N D258N S261H N270Q H374N | 85 |
| PhV-068 | S1- D2- T3Q A4G P5A A6D G7K F8M Q9K K12R K76N N78T D92E Q121T A123V S164E A200N D258N S261H N270Q H374N | 84 |
| PhV-069 | S1- D2- T3Q A4G P5A A6D G7K F8M Q9K K12R K76N N78T D92T Q121T A123V S164E A200N D258N S261H N270Q H374N | 84 |
| PhV-070 | S1- D2- T3Q A4G P5A A6D G7K F8M Q9K K12R K76N N78T D92V Q121T A123V S164E A200N D258N S261H N270Q H374N | 85 |
| PhV-071 | ASRNADKMK9 K12R K76N N78T D92N Q121T S164E A200N D258N S261H N270Q H374N | 83 |
| PhV-072 | S1- D2- T3Q A4G P5A A6D G7K F8M Q9K K12R K76N N78T D92E Q121T S164E A200N D258N S261H N270Q H374N | 84 |
| PhV-073 | S1- D2- T3Q A4G P5A A6D G7K F8M Q9K K12R K76I N78T D92N Q109N Q121T S164E A200N D258N S261H N270Q I300L H374N | 83 |
| PhV-074 | S1- D2- T3Q A4G P5A A6D G7K F8M Q9K K12R K76I N78T D92N Q109N Q121T S164E A200N D258N S261H N270Q I300L H374N D398E | 83 |
| PhV-075 | S1- D2- T3Q A4G P5A A6D G7K F8M Q9K K12R K76N N78T D92N Q109N Q121T A144E S164E A200N S217G D258N S261H N270Q I300L H374N | 83 |
| PhV-076 | S1- D2- T3Q A4G P5A A6D G7K F8M Q9K K12R K76N N78T D92A Q121T A123V S164E A200N D258N S261H N270Q I300L H374N | 84 |
| PhV-077 | S1- D2- T3Q A4G P5A A6D G7K F8M Q9K K12R K76N N78T D92E Q121T A123V S164E A200N D258N S261H N270Q I300L H374N | 83 |
| PhV-078 | S1- D2-T3Q A4G P5A A6D G7K F8M Q9K K12R K76N N78T D92T Q121T A123V S164E A200N D258N S261H N270Q I300L H374N | 84 |
| PhV-079 | S1- D2- T3Q A4G P5A A6D G7K F8M Q9K K12R K76N N78T D92V Q121T A123V S164E A200N D258N S261H N270Q I300L H374N | 83 |
| PhV-080 | S1- D2- T3Q A4G P5A A6D G7K F8M Q9K K12R K76N N78T D92N Q121T S136K Q141K S164E A200N D258N S261H N270Q I300L H374N | 81 |
| PhV-081 | D2E A4E A6S F8Y N33M K76N N78T D92N Q121T A123V T152G S164E A200N D258N S261H N270Q H374N D398E | 84 |
| PhV-082 | D2E A4E A6S F8Y N33M K76N N78T D92N Q121T T152G T156G S164E A200N D258N S261H N270Q Q276N H374N D398E | 82 |
| PhV-083 | D2E A4E A6S F8Y N33M K76N N78T D92N Q121T T152G S164E A200N D258N S261H N270Q Q276N I300L H374N D398E | 83 |
| PhV-084 | S1- D2- T3Q A4G P5A A6D G7K F8M Q9K K12R K76N N78T D92A Q121T S136K S164E A200N D258N S261H N270Q H374N | 83 |
| PhV-085 | S1- D2- T3Q A4G P5A A6D G7K F8M Q9K K12R K76I N78T D92A Q109N Q121T S164E A200N D258N S261H N270Q I300L H374N | 84 |
| PhV-086 | S1- D2- T3Q A4G P5A A6D G7K F8M Q9K K12R K76N N78T D92N Q109N Q121T A123V S164E A200N D258N S261H K268A N270Q Q276N I300L N346G H374N | 82 |
| PhV-087 | S1- D2- T3Q A4G P5A A6D G7K F8M Q9K K12R K76N N78T D92N Q121T E155N S164E A200N D258N S261H N270Q H374N | 82 |
| PhV-088 | D2E A4E A6S F8Y N33M K76N N78T D92N Q121T T152G T156G S164E A200N D258N S261H N270Q H374N D398E | 83 |

TABLE 1-continued

Thermostability ($T_{50}$) of the phytase variants in °C. (see also FIG. 1). Changes over SEQ ID 24 are specified at individual amino acid exchanges in the form [original amino acid][position][new amino acid]. The symbol "—" in this case indicates a deletion of the amino acid in question. The numbering of the amino acid position always refers to SEQ ID 24.

| Mutant | Mutation | $T_{50}$ [° C.] |
|---|---|---|
| PhV-089 | D2E A4E A6S F8Y N33M K76N N78T D92N Q121T T152G S164E A200N D258N S261H N270Q I300L H374N D398E | 83 |
| PhV-090 | S1- D2- T3Q A4G P5A A6D G7K F8M Q9K K12R K76N N78T D92N Q121T E155H S164E A200N D258N S261H N270Q H374N | 82 |
| PhV-091 | S1- D2- T3Q A4G P5A A6D G7K F8M Q9K K12R K76N N78T D92N Q121T E155G S164E A200N D258N S261H N270Q D345G H374N | 82 |
| PhV-092 | S1- D2- T3Q A4G P5A A6D G7K F8M Q9K K12R K76N N78T D92N Q121T E155N S164E A200N D258N S261H N270Q D345G H374N | 82 |
| PhV-093 | S1- D2- T3Q A4G P5A A6D G7K F8M Q9K K12R K76N N78T D92N Q121T E155H S164E A200N D258N S261H N270Q D345M H374N | 82 |
| PhV-094 | S1- D2- T3Q A4G P5A A6D G7K F8M Q9K K12R N33M K76N N78T D92N Q109N Q121T A123V T152G T156G S164E A200N D258N S261H N270Q Q276N I300L N346G H374N | 83 |
| PhV-095 | S1- D2- T3Q A4G P5A A6D G7K F8M Q9K K12R N33M K76I N78T D92N Q121T A144E T152G S164E A200N S217G D258N S261H N270Q H374N D398E | 83 |
| PhV-096 | S1- D2- T3Q A4G P5A A6D G7K F8M Q9K K12R K76I N78T D92A Q121T A123V S164E A200N D258N S261H N270Q H374N | 84 |
| PhV-097 | S1- D2- T3Q A4G P5A A6D G7K F8M Q9K K12R K76N N78T D92A Q109N Q121T A123V Q159N S164E A200N D258N S261H N270Q H374N | 85 |
| PhV-098 | S1- D2- T3Q A4G P5A A6D G7K F8M Q9K K12R K76N N78T D92A Q121T S136K S164E A200N D258N S261H N270Q H374N | 84 |
| PhV-099 | D2E A4E A6S F8Y N33D K76N N78T D92N Q121T T152G S164E A200N D258N S261H N270Q H374N | 84 |
| PhV-100 | N33D K76N N78T D92N Q121T S164E A200N H374N | 82 |
| PhV-101 | N33D K76N N78T D92N Q121T T152G S164E A200N H374N | 83 |
| PhV-102 | N33M K76N N78T D92N Q121T S164E A200N H374N | 82 |
| PhV-103 | N33D D92N Q121T T152G S164E A200N D258N S261H N270Q H374N | 84 |
| PhV-104 | N33M K76N N78T D92N Q121T T152G S164E A200N D258N S261H N270Q H374N | 84 |
| PhV-105 | N33D D92N S164E A200N D258N S261H N270Q H374N | 83 |
| PhV-106 | N33D K76N N78T D92N Q121T T152G S164E A200N D258N S261H H374N | 83 |
| PhV-107 | N33D K76N N78T D92N Q121T S164E A200N D258N S261H N270Q H374N | 83 |
| PhV-108 | N33D D92N Q121T A123V A144E T152G S164E A200N S217G D258N S261H N270Q H374N | 84 |
| PhV-109 | N33D D92N Q121T A123V A144E T152G Q159N S164E A200N D258N S261H N270Q H374N | 83 |
| PhV-110 | N33D D92N Q121T T152G Q159N S164E A200N S217G D258N M260I S261H N270Q H374N | 84 |
| PhV-111 | N33D D92A Q121T T152G Q159N S164E A200N S217G D258N M260I S261H N270Q H374N | 85 |
| PhV-112 | S1- D2- T3Q A4G P5A N33D D92N Q121T T152G S164E A200N D258N S261H N270Q H374N | 84 |
| PhV-113 | S1- D2- T3Q A4G P5A N33D D92N Q121T T152G S164E A200N D258N S261H N270Q H374N | 84 |
| PhV-114 | A6D G7K F8M Q9K N33D D92N Q121T T152G S164E A200N D258N S261H N270Q H374N | 84 |
| PhV-115 | N33D D92A Q121T A123V A144E T152G Q159N S164E A200N S217G D258N M260I S261H N270Q H374N | 85 |
| PhV-116 | N33D D92N Q121T A123V A144E T152G Q159N S164E A200N S217G D258N M260I S261H N270Q H374N | 84 |
| PhV-117 | S1A D2S T3R A4N N33D D92N Q121T T152G S164E A200N D258N S261H N270Q H374N | 84 |
| PhV-118 | N33D D92N Q121T A123V A144E T152G S164E A200N S217G D258N M260I S261H N270Q H374N | 84 |
| PhV-119 | N33D D92N Q121T T152G S164E A200N D258N S261H N270Q H374N | 84 |
| PhV-120 | D2E A4E A6S F8Y N33M K76N N78T D92N Q121T T152G S164E A200N D258N S261H N270Q H374N | 84 |
| PhV-121 | S1- D2- T3Q A4G P5A A6D G7K F8M Q9K K12R N33M K76N N78T D92N Q121T T152G S164E A200N D258N S261H N270Q H374N | 84 |
| PhV-122 | N33M K76N N78T D92N Q121T T152G S164E A200N D258N S261H N270Q H374N | 84 |
| PhV-123 | D2E A4E A6S F8Y N33D D92N S164E A200N H374N | 82 |
| PhV-124 | D2E A4E A6S F8Y N33D K76N N78T D92N Q121T T152G S164E A200N D258N S261H H374N | 85 |
| PhV-125 | N33D D92A Q121T A123V T152G S164E A200N D258N S261H N270Q H374N | 84 |

TABLE 1-continued

Thermostability ($T_{50}$) of the phytase variants in °C. (see also FIG. 1). Changes over SEQ ID 24 are specified at individual amino acid exchanges in the form [original amino acid][position][new amino acid]. The symbol "—" in this case indicates a deletion of the amino acid in question. The numbering of the amino acid position always refers to SEQ ID 24.

| Mutant | Mutation | $T_{50}$ [°C] |
|---|---|---|
| PhV-126 | N33D D92A Q121T A123V T152G S164E A200N D258N M260I S261H N270Q H374N | 84 |
| PhV-127 | N33D D92N Q121T A144E T152G Q159N S164E A200N S217G D258N M260I S261H N270Q H374N | 84 |
| PhV-128 | A4E A6S N33D D92N Q121T T152G S164E A200N D258N S261H N270Q H374N | 84 |
| PhV-129 | N33D R67L D92N Q121T A144E T152G Q159N S164E A200N S217G D258N M260I S261H N270Q H374N | 84 |
| PhV-130 | L16V N33D D92N Q121T A144E T152G Q159N S164E A200N S217G D258N M260I S261H N270Q H374N | 83 |
| PhV-131 | K12R N33D D92N Q121T A144E T152G Q159N S164E A200N S217G D258N M260I S261H N270Q H374N | 84 |
| PhV-132 | K12R L16V N33D D92N Q121T T152G Q159N S164E A200N S217G D258N M260I S261H N270Q H374N | 83 |
| PhV-133 | N33D R67L D92N Q121T A123V T152G Q159N S164E A200N S217G D258N M260I S261H N270Q H374N | 85 |
| PhV-134 | N33D D92N Q121T A144E T152G Q159N S164E A166E A200N S217G D258N M260I S261H N270Q H374N | 85 |
| PhV-135 | N33D R67L D92N Q121T A123V A144E T152G Q159N S164E A166E A200N S217G D258N M260I S261H N270Q H374N | 84 |
| PhV-136 | N33D D92A Q121T A123V A144E T152G Q159N S164E A166E A200N S217G D258N M260I S261H N270Q H374N | 84 |
| PhV-137 | N33D D92A Q121T T152G Q159N S164E A166E A200N S217G D258N M260I S261H N270Q H374N D398E | 83 |
| PhV-138 | N33D D92N Q121T A123V A144E T152G Q159N S164E A166E A200N S217G D258N M260I S261H N270Q H374N D398E | 84 |
| PhV-139 | N33D D92N Q121T A144E T152G Q159N S164E A200N S217G D258N S261H N270Q H374N | 84 |
| PhV-140 | K12R N33D R67L D92N Q121T A123V A144E T152G S164E A200N S217G D258N S261H N270Q H374N | 84 |
| PhV-141 | L16V N33D R67L D92N Q121T A123V A144E T152G S164E A200N S217G D258N S261H N270Q H374N | 84 |
| PhV-142 | N33D R67L D92N Q121T A123V A144E T152G S164E A166E A200N S217G D258N S261H N270Q H374N | 84 |
| PhV-143 | N33D D92N Q121T A123V A144E T152G S164E A166E A200N S217G D258N S261H N270Q I300L H374N | 84 |
| PhV-144 | N33D D92N I120L Q121T A123V A144E T152G S164E A200N S217G D258N S261H N270Q I300L H374N | 84 |
| PhV-145 | N33D D92N I120L Q121T A123V A144E T152G S164E A200N S217G D258N S261H N270Q L371A H374N | 84 |
| PhV-146 | N33D R67L D92N I120L Q121T A123V A144E T152G S164E A166E A200N S217G D258N S261H N270Q L371A H374N | 84 |
| PhV-147 | N33D D92N I120L Q121T A123V A144E T152G S164E A200N S217G D258N S261H N270Q I300L L371A H374N | 84 |

Determination of the pH Profile

To determine the pH profile, a modified reaction buffer (100 mM Na acetate, 100 mM glycine, 100 mM imidazole, 1 mM $CaCl_2$, 0.01% Tween 20), which is brought to pH values in the range of from pH 1.5-7 using dilute hydrochloric acid, is used for the phytase assay. To determine the relative activity, the activity measured at pH 5.5 is set at 100%. The results are shown in Tables 2 and 3.

Figure 2:
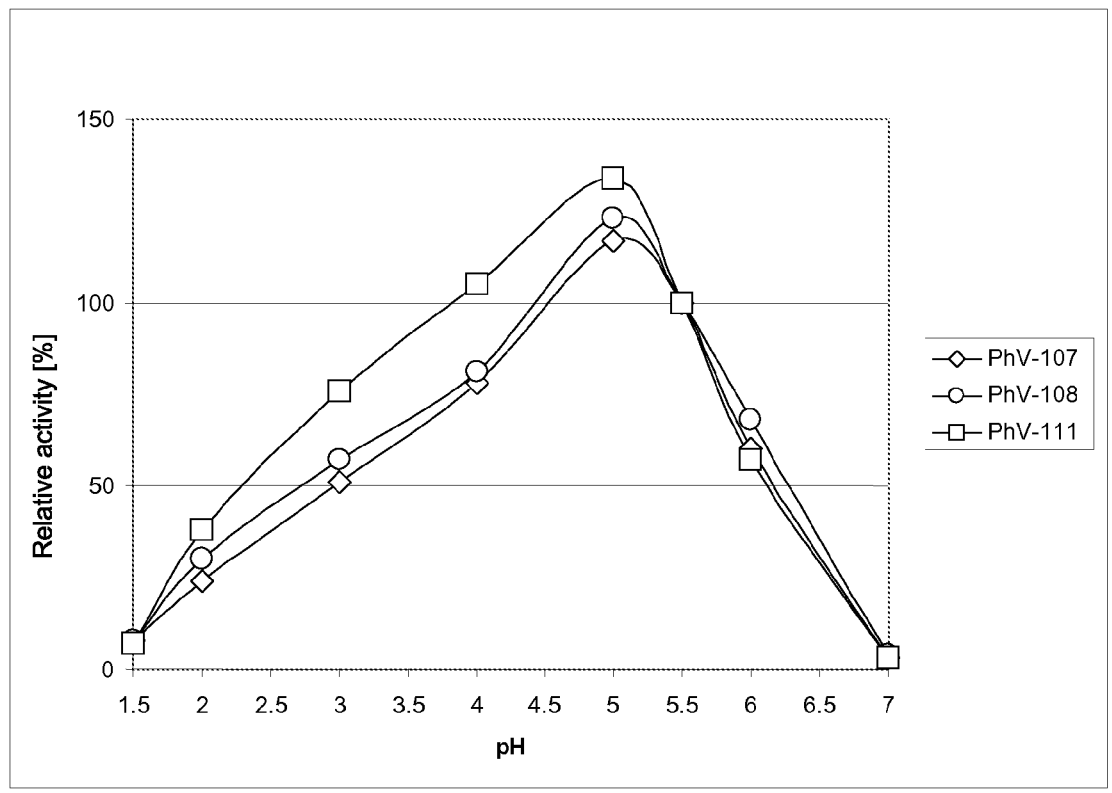
FIGS. 2A and B show the pH profiles of the phytases PhV-107, PhV-108, PhV-111 and PhV-007, PhV-058, PhV-081 according to the invention. The phytase activity is determined at the respective pH specified. To determine the relative activity data, the activity measured at pH 5.5 is set at 100%. A) The phytases are expressed in *A. niger* and measured from the culture supernatant. B) The phytases are expressed in *E. coli*, concentrated using an Ni-NtA column and then measured.
Figure 2:
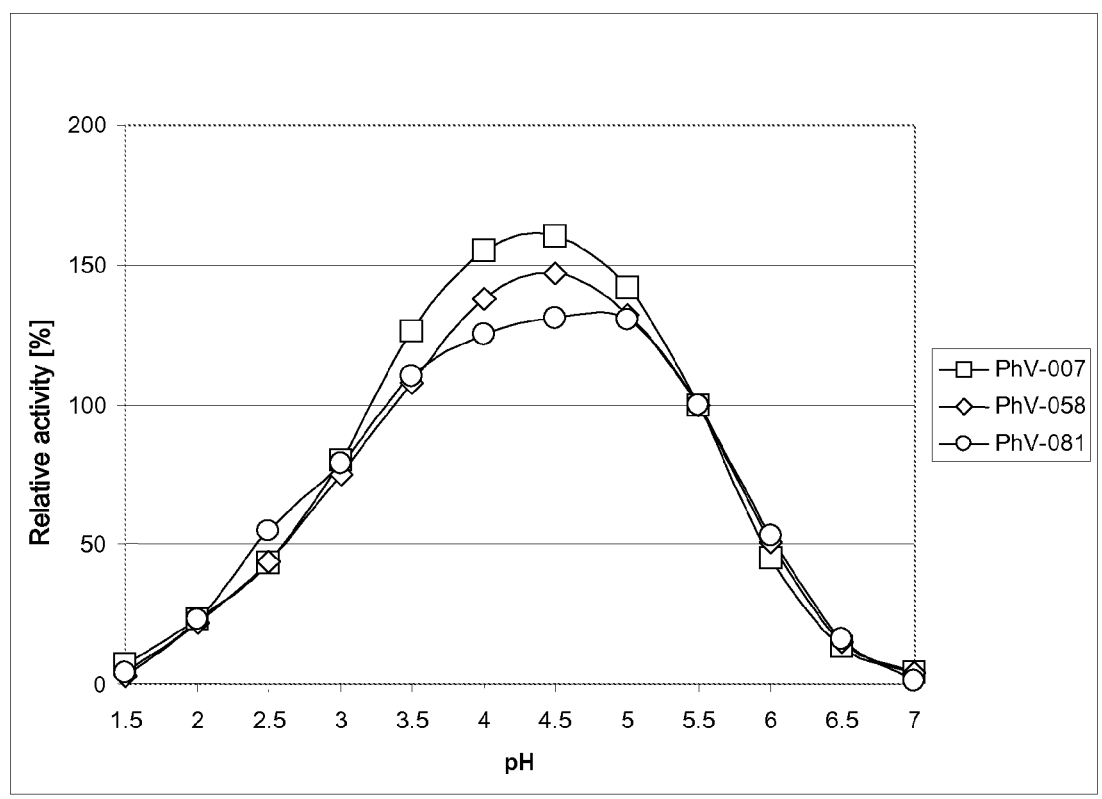
Figure 3:
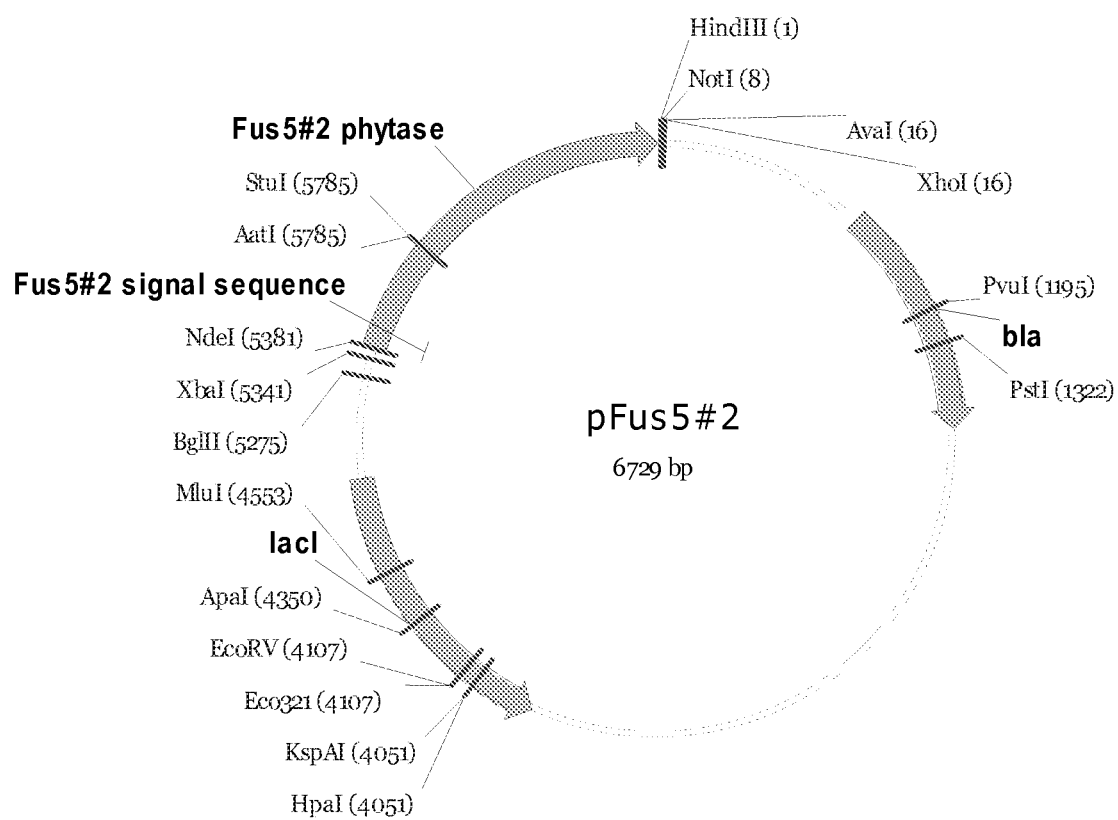
FIG. 3 shows the plasmid map of the expression plasmid pFus5#2.
Figure 4:
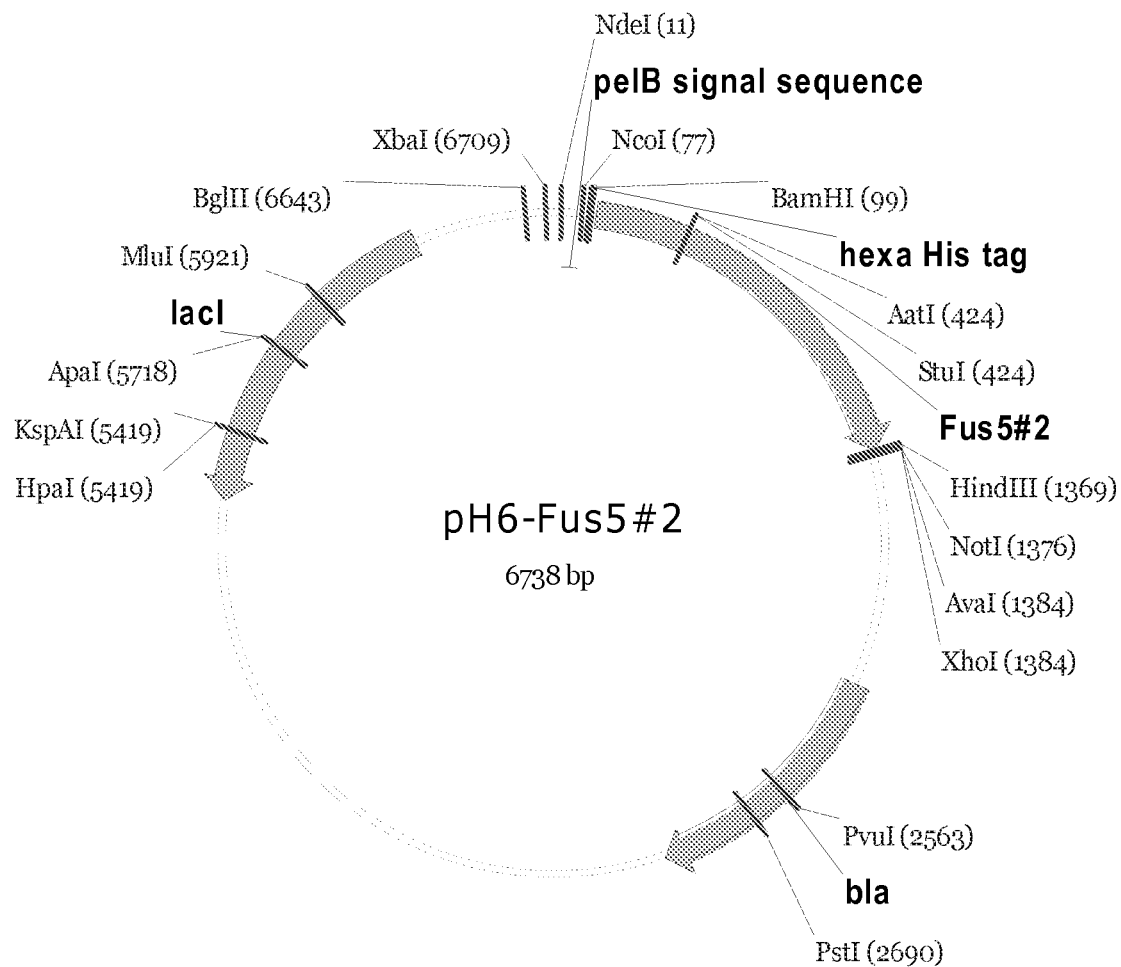
FIG. 4 shows the plasmid map of the expression plasmid pH6-Fus5#2.
Figure 5:
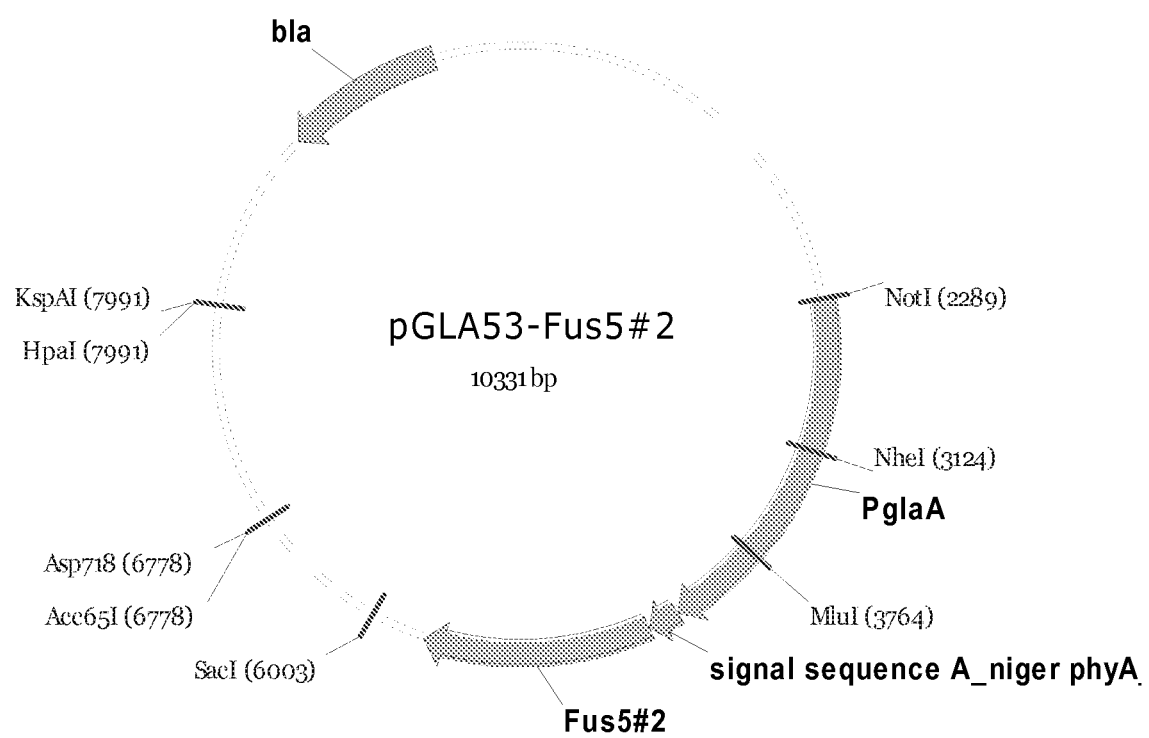
FIG. 5 shows the plasmid map of the expression plasmid pGLA53-Fus5#2.

TABLE 2 pH profiles of some phytase variants. The phytase is expressed in *A. niger* and measured directly from the culture supernatant. The phytase activity is shown in % as a relative value of the activity determined at pH 5.5 (see FIG. 2A).

| | pH | | | | | | | |
|---|---|---|---|---|---|---|---|---|
| | 1.5 | 2 | 3 | 4 | 5.0 | 5.5 | 6 | 7.0 |
| PhV-107 | 8 | 24 | 51 | 78 | 117 | 100 | 60 | 3 |
| PhV-108 | 8 | 30 | 57 | 81 | 123 | 100 | 68 | 4 |
| PhV-109 | 6 | 24 | 49 | 76 | 127 | 100 | 59 | 3 |
| PhV-110 | 6 | 27 | 48 | 85 | 134 | 100 | 70 | 4 |
| PhV-111 | 7 | 38 | 76 | 105 | 134 | 100 | 57 | 3 |
| PhV-124 | 7 | 41 | 61 | 76 | 125 | 100 | 67 | 4 |

TABLE 3 pH profiles of some phytase variants. The phytase is expressed in
E. coli and purified via Ni affinity chromatography. The phytase
activity is shown in % as a relative value of the activity
determined at pH 5.5 (see FIG. 2B).

| | pH | | | | | | | | | | |
|---|---|---|---|---|---|---|---|---|---|---|---|
| | 1.5 | 2 | 2.5 | 3 | 3.5 | 4 | 4.5 | 5 | 5.5 | 6 | 6.5 | 7 |
| PhV-007 | 7 | 23 | 43 | 80 | 126 | 155 | 160 | 142 | 100 | 45 | 13 | 4 |
| PhV-058 | 3 | 22 | 44 | 75 | 108 | 138 | 147 | 132 | 100 | 51 | 15 | 4 |
| PhV-067 | 6 | 32 | 70 | 123 | 171 | 201 | 182 | 158 | 100 | 52 | 17 | 5 |
| PhV-071 | 4 | 23 | 44 | 77 | 119 | 151 | 157 | 143 | 100 | 53 | 16 | 4 |
| PhV-081 | 4 | 23 | 55 | 79 | 110 | 125 | 131 | 130 | 100 | 53 | 16 | 1 |

Determination of the Stability at pH 2

To determine the stability at pH 2, the phytase sample is diluted in buffer (250 mM glycine, 3 mg/ml BSA, pH 2) to 30 U/ml. The sample is incubated for 30 min at 37° C. Thereafter, the sample is diluted directly with reaction buffer (250 mM Na acetate, 1 mM $CaCl_2$, 0.01% Tween 20, pH 5.5) to the optimum measuring range of the phytase activity determination (approx. 0.6 U/ml), and the phytase activity is measured.

By way of reference, the sample is incubated in parallel for 30 min at 37° C. in reaction buffer at a concentration of 30 U/ml, and the phytase activity is likewise analyzed. The activities of the pH-stressed samples are standardized to the reference value, which is set as 100% stability. Natuphos® (BASF) is likewise employed in the assay by way of comparison with a commercial phytase.

TABLE 4

Determination of the stability at pH 2 of some phytase variants, and of the
phytase Fus5#2 and the commercial phytase Natuphos ®. Samples with
a stability > 90% are marked as "stable". For a better gradual
differentiation between the unstable samples, the stabilities measured are indicated in %.

| Phytase | | Stability at pH2 |
|---|---|---|
| Natuphos ® | | 65% |
| Fus5#2 | SEQ ID 18 | stable |
| Mutant | Mutation with regard to SEQ ID 24 | |
| PhV-056 | D2E A4E A6S F8Y N33M K76N N78T D92N Q121T S164E A200N D258N S261H N270Q Q276N N346G H374N | stable |
| PhV-057 | S1- D2- T3Q A4G P5A A6D G7K F8M Q9K K12R N33M K76N N78T D92N Q109N Q121T T152G S164E A200N D258N S261H N270Q Q276N I300L N346G H374N | stable |
| PhV-058 | D2E A4E A6S F8Y N33M K76N N78T D92N Q121T T152G S164E A200N D258N S261H N270Q H374N | stable |
| PhV-059 | D2E A4E A6S F8Y N33M K76N N78T D92N Q121T T152G S164E A200N D258N S261H N270Q H374N D398E | stable |
| PhV-067 | S1- D2- T3Q A4G P5A A6D G7K F8M Q9K K12R K76N N78T D92A Q121T A123V S164E A200N D258N S261H N270Q H374N | stable |
| PhV-071 | ASRNADKMK9 K12R K76N N78T D92N Q121T S164E A200N D258N S261H N270Q H374N | stable |
| PhV-081 | D2E A4E A6S F8Y N33M K76N N78T D92N Q121T A123V T152G S164E A200N D258N S261H N270Q H374N D398E | stable |
| PhV-107 | N33D K76N N78T D92N Q121T S164E A200N D258N S261H N270Q H374N | stable |
| PhV-108 | N33D D92N Q121T A123V A144E T152G S164E A200N S217G D258N S261H N270Q H374N | stable |
| PhV-109 | N33D D92N Q121T A123V A144E T152G S164E Q159N S164E A200N D258N S261H N270Q H374N | stable |
| PhV-110 | N33D D92N Q121T T152G Q159N S164E A200N S217G D258N M260I S261H N270Q H374N | stable |
| PhV-111 | N33D D92A Q121T T152G Q159N S164E A200N S217G D258N M260I S261H N270Q H374N | stable |

Determination of the Stability to Pepsin

To determine the stability to pepsin, the phytase sample is diluted to 30 U/ml in pepsin-comprising buffer (250 mM glycine, 3 mg/ml BSA, pH 2, 10 mg/ml pepsin (Sigma P-7000, 445 U/mg). The sample is incubated for 30 min at 37° C. Thereafter, the sample is diluted directly with reaction buffer (250 mM Na acetate, 1 mM $CaCl_2$, 0.01% Tween 20, pH 5.5) to the optimum measuring range of the phytase activity determination (approx. 0.6 U/ml), and the phytase activity is determined. By way of reference, the sample is incubated in parallel for 30 min at 37° C. in reaction buffer pH 5.5 at a concentration of 30 U/ml, and the phytase activity is likewise analyzed. The activities of the pepsin-treated samples are standardized to the reference value, which is set as 100% stability. Natuphos® (Natuphos® 10000L, BASF) was likewise employed in the assay by way of comparison with a commercial phytase.

TABLE 5

Determination of the stability to pepsin of some phytase variants, and of the phytase Fus5#2 and the commercial phytase Natuphos ®. Samples with a stability > 80% are marked as "stable". For a better gradual differentiation between the unstable samples, the stabilities measured are indicated in %.

| Phytase | | Stability to pepsin |
|---|---|---|
| Natuphos ® | | 20% |
| Fus5#2 | SEQID18 | 1% |
| Mutant | Mutation with regard to SEQ ID 24 | |
| PhV-056 | D2E A4E A6S F8Y N33M K76N N78T D92N Q121T S164E A200N D258N S261H N270Q Q276N N346G H374N | stable |
| PhV-057 | S1- D2- T3Q A4G P5A A6D G7K F8M Q9K K12R N33M K76N N78T D92N Q109N Q121T T152G S164E A200N D258N S261H N270Q Q276N I300L N346G H374N | stable |
| PhV-058 | D2E A4E A6S F8Y N33M K76N N78T D92N Q121T T152G S164E A200N D258N S261H N270Q H374N | stable |
| PhV-059 | D2E A4E A6S F8Y N33M K76N N78T D92N Q121T T152G S164E A200N D258N S261H N270Q H374N D398E | stable |
| PhV-067 | S1- D2- T3Q A4G P5A A6D G7K F8M Q9K K12R K76N N78T D92A Q121T A123V S164E A200N D258N S261H N270Q H374N | stable |
| PhV-071 | ASRNADKMK9 K12R K76N N78T D92N Q121T S164E A200N D258N S261H N270Q H374N | stable |
| PhV-081 | D2E A4E A6S F8Y N33M K76N N78T D92N Q121T A123V T152G S164E A200N D258N S261H N270Q H374N D398E | stable |
| PhV-107 | N33D K76N N78T D92N Q121T S164E A200N D258N S261H N270Q H374N | stable |
| PhV-108 | N33D D92N Q121T A123V A144E T152G S164E A200N S217G D258N S261H N270Q H374N | stable |
| PhV-109 | N33D D92N Q121T A123V A144E T152G Q159N S164E A200N D258N S261H N270Q H374N | stable |
| PhV-110 | N33D D92N Q121T T152G Q159N S164E A200N S217G D258N M260I S261H N270Q H374N | stable |
| PhV-111 | N33D D92A Q121T T152G Q159N S164E A200N S217G D258N M260I S261H N270Q H374N | stable |

We claim:

1. A phytase comprising an amino acid sequence having at least 90% sequence identity to the amino acid sequence of SEQ ID NO: 24 and at least one modification selected from the group consisting of S1-; D2-,E; T3Q, A4G,E; P5A; A6S, D; G7K; F8Y,M; Q9K; K12R; L16V; N33D,M; H37Y; R67L; Q71E; P75N; K76N,I; D77T; N78T; D92A,E,N,T,V; Q109N, E; Q118S; N119A,T; I120L; Q121T; A123V; S136K; Q141K; A144E; T152G,A; E155N; T156G; Q159N; S164E; A166E,H; Q193L; A200N; S217G; D258N; M260I; S261H; K268N; N270Q; Q276N; I300L; T322Q; D345G; N346G; L371A; H374N; D398E and Q406K based on the amino acid position according to SEQ ID NO: 24.

2. The phytase according to claim 1, which has 5, 6, 7, 8, 9, or 10 of the amino acid modifications.

3. The phytase according to claim 1, which has at least one of the cumulative modifications selected from the group consisting of:
- (PhV-001) D2E A4E A6S F8Y N33M K76N N78T D92N Q121T A123V T152G S164E A200N D258N S261H N270Q H374N D398E
- (PhV-002) D2E A4E A6S F8Y N33M K76N N78T D92A Q121T A123V T152G S164E A200N D258N S261H N270Q H374N D398E
- (PhV-003) D2E A4E A6S F8Y N33M R67L K76N N78T D92A Q121T A123V T152G S164E A200N D258N M260I S261H N270Q H374N D398E
- (PhV-004) D2E A4E A6S F8Y N33M R67L K76N N78T D92N Q109N Q121T A123V A144E T152G Q159N S164E A200N S217G D258N M260I S261H N270Q H374N D398E
- (PhV-020) S1-D2-T3Q A4G P5A A6D G7K F8M Q9K K12R N33M K76N N78T D92N Q121T T152G S164E A200N D258N S261H N270Q H374N
- (PhV-031) D2E A4E A6S F8Y N33M K76N N78T D92N Q121T S164E A200N D258N S261H N270Q H374N
- (PhV-048) S1-D2-T3Q A4G P5A A6D G7K F8M Q9K K12R N33M K76I N78T D92N Q121T T152G S164E A200N D258N S261H N270Q H374N
- (PhV-053) S1-D2-T3Q A4G P5A A6D G7K F8M Q9K K12R N33M K76N N78T D92N Q121T A123V T152G S164E A200N D258N S261H N270Q I300L H374N
- (PhV-055) D2E A4E A6S F8Y N33M K76N N78T D92N Q121T T152G S164E A200N D258N S261H N270Q Q276N H374N
- (PhV-058) D2E A4E A6S F8Y N33M K76N N78T D92N Q121T T152G S164E A200N D258N S261H N270Q H374N
- (PhV-059) D2E A4E A6S F8Y N33M K76N N78T D92N Q121T T152G S164E A200N D258N S261H N270Q H374N D398E
- (PhV-060) S1-D2-T3Q A4G P5A A6D G7K F8M Q9K K12R N33M K76N N78T D92N Q109N Q121T T152G S164E A200N D258N S261H N270Q I300L N346G H374N
- (PhV-064) S1-D2-T3Q A4G P5A A6D G7K F8M Q9K K12R K76N N78T D92A Q121T S164E A200N D258N S261H N270Q H374N
- (PhV-065) S1-D2-T3Q A4G P5A A6D G7K F8M Q9K K12R K76N N78T D92T Q121T S164E A200N D258N S261H N270Q H374N
- (PhV-066) S1-D2-T3Q A4G P5A A6D G7K F8M Q9K K12R K76N N78T D92V Q121T S164E A200N D258N S261H N270Q H374N
- (PhV-067) S1-D2-T3Q A4G P5A A6D G7K F8M Q9K K12R K76N N78T D92A Q121T A123V S164E A200N D258N S261H N270Q H374N
- (PhV-068) S1-D2-T3Q A4G P5A A6D G7K F8M Q9K K12R K76N N78T D92E Q121T A123V S164E A200N D258N S261H N270Q H374N
- (PhV-069) S1; -D2-T3Q A4G P5A A6D G7K F8M Q9K K12R K76N N78T D92T Q121T A123V S164E A200N D258N S261H N270Q H374N
- (PhV-070) S1-D2-T3Q A4G P5A A6D G7K F8M Q9K K12R K76N N78T D92V Q121T A123V S164E A200N D258N S261H N270Q H374N
- (PhV-072) S1-D2-T3Q A4G P5A A6D G7K F8M Q9K K12R K76N N78T D92E Q121T S164E A200N D258N S261H N270Q H374N
- (PhV-073) S1-D2-T3Q A4G P5A A6D G7K F8M Q9K K12R K76I N78T D92N Q109N Q121T S164E A200N D258N S261H N270Q I300L H374N
- (PhV-074) S1-D2-T3Q A4G P5A A6D G7K F8M Q9K K12R K76I N78T D92N Q109N Q121T S164E A200N D258N S261H N270Q I300L H374N D398E
- (PhV-075) S1-D2-T3Q A4G P5A A6D G7K F8M Q9K K12R K76N N78T D92N Q109N Q121T A144E S164E A200N S217G D258N S261H N270Q I300L H374N
- (PhV-076) S1-D2-T3Q A4G P5A A6D G7K F8M Q9K K12R K76N N78T D92A Q121T A123V S164E A200N D258N S261H N270Q I300L H374N (PhV-077) S1-D2-T3Q A4G P5A A6D G7K F8M Q9K K12R K76N N78T D92E Q121T A123V S164E A200N D258N S261H N270Q I300L H374N (PhV-078) S1-D2-T3Q A4G P5A A6D G7K F8M Q9K K12R K76N N78T D92T Q121T A123V S164E A200N D258N S261H N270Q I300L H374N (PhV-079) S1-D2-T3Q A4G P5A A6D G7K F8M Q9K K12R K76N N78T D92V Q121T A123V S164E A200N D258N S261H N270Q I300L H374N (PhV-081) D2E A4E A6S F8Y N33M K76N N78T D92N Q121T A123V T152G S164E A200N D258N S261H N270Q H374N D398E (PhV-083) D2E A4E A6S F8Y N33M K76N N78T D92N Q121T T152G S164E A200N D258N S261H N270Q Q276N I300L H374N D398E (PhV-084) S1-D2-T3Q A4G P5A A6D G7K F8M Q9K K12R K76N N78T D92A Q121T S136K S164E A200N D258N S261H N270Q H374N (PhV-085) S1-D2-T3Q A4G P5A A6D G7K F8M Q9K K12R K76I N78T D92A Q109N Q121T S164E A200N D258N S261H N270Q I300L H374N (PhV-088) D2E A4E A6S F8Y N33M K76N N78T D92N Q121T T152G T156G S164E A200N D258N S261H N270Q H374N D398E (PhV-089) D2E A4E A6S F8Y N33M K76N N78T D92N Q121T T152G S164E A200N D258N S261H N270Q I300L H374N D398E (PhV-094) S1-D2-T3Q A4G P5A A6D G7K F8M Q9K K12R N33M K76N N78T D92N Q109N Q121T A123V T152G T156G S164E A200N D258N S261H N270Q Q276N I300L N346G H374N (PhV-095) S1-D2-T3Q A4G P5A A6D G7K F8M Q9K K12R N33M K761 N78T D92N Q121T A144E T152G S164E A200N S217G D258N S261H N270Q H374N D398E (PhV-096) S1-D2-T3Q A4G P5A A6D G7K F8M Q9K K12R K76I N78T D92A Q121T A123V S164E A200N D258N S261H N270Q H374N (PhV-097) S1-D2-T3Q A4G P5A A6D G7K F8M Q9K K12R K76N N78T D92A Q109N Q121T A123V Q159N S164E A200N D258N S261H N270Q H374N (PhV-098) S1-D2-T3Q A4G P5A A6D G7K F8M Q9K K12R K76N N78T D92A Q121T S136K S164E A200N D258N S261H N270Q H374N (PhV-099) D2E A4E A6S F8Y N33D K76N N78T D92N Q121T T152G S164E A200N D258N S261H N270Q H374N (PhV-101) N33D K76N N78T D92N Q121T T152G S164E A200N H374N (PhV-103) N33D D92N Q121T T152G S164E A200N D258N S261H N270Q H374N (PhV-104) N33M K76N N78T D92N Q121T T152G S164E A200N D258N S261H N270Q I-1374N (PhV-105) N33D D92N S164E A200N D258N S261H N270Q H374N (PhV-106) N33D K76N N78T D92N Q121T T152G S164E A200N D258N S261H H374N (PhV-107) N33D K76N N78T D92N Q121T S164E A200N D258N S261H N270Q H374N (PhV-108) N33D D92N Q121T A123V A144E T152G S164E A200N S217G D258N S261H N270Q H374N (PhV-109) N33D D92N Q121T A123V A144E T152G Q159N S164E A200N D258N S261H N270Q H374N (PhV-110) N33D D92N Q121T T152G Q159N S164E A200N S217G D258N M260I S261H N270Q H374N (PhV-111) N33D D92A Q121T T152G Q159N S164E A200N S217G D258N M260I S261H N270Q H374N (PhV-112) S1-D2-T3Q A4G P5A N33D D92N Q121T T152G S164E A200N D258N S261H N270Q H374N (PhV-113) S1-D2-T3Q A4G P5A N33D D92N Q121T T152G S164E A200N D258N S261H N270Q H374N (PhV-114) A6D G7K F8M Q9K N33D D92N Q121T T152G S164E A200N D258N S261H N270Q H374N (PhV-115) N33D D92A Q121T A123V A144E T152G Q159N S164E A200N S217G D258N M260I S261H N270Q H374N (PhV-116) N33D D92N Q121T A123V A144E T152G Q159N S164E A200N S217G D258N M260I S261H N270Q H374N (PhV-117) S1A D2S T3R A4N N33D D92N Q121T T152G S164E A200N D258N S261H N270Q H374N (PhV-118) N33D D92N Q121T A123V A144E T152G S164E A200N S217G D258N M260I S261H N270Q H374N (PhV-119) N33D D92N Q121T T152G S164E A200N D258N S261H N270Q H374N (PhV-120) D2E A4E A6S F8Y N33M K76N N78T D92N Q121T T152G S164E A200N D258N S261H N270Q H374N (PhV-121) S1-D2-T3Q A4G P5A A6D G7K F8M Q9K K12R N33M K76N N78T D92N Q121T T152G S164E A200N D258N S261H N270Q H374N (PhV-122) N33M K76N N78T D92N Q121T T152G S164E A200N D258N S261H N270Q H374N (PhV-123) D2E A4E A6S F8Y N33D D92N S164E A200N H374N (PhV-124) D2E A4E A6S F8Y N33D K76N N78T D92N Q121T T152G S164E A200N D258N S261H H374N (PhV-125) N33D D92A Q121T A123V T152G S164E A200N D258N S261H N270Q H374N (PhV-126) N33D D92A Q121T A123V T152G S164E A200N D258N M260I S261H N270Q H374N (PhV-127) N33D D92N Q121T A144E T152G Q159N S164E A200N S217G D258N M260I S261H N270Q H374N (PhV-128) A4E A6S N33D D92N Q121T T152G S164E A200N D258N S261H N270Q H374N (PhV-129) N33D R67L D92N Q121T A144E T152G Q159N S164E A200N S217G D258N M260I S261H N270Q H374N (PhV-130) L16V N33D D92N Q121T A144E T152G Q159N S164E A200N S217G D258N M260I S261H N270Q H374N (PhV-131) K12R N33D D92N Q121T A144E T152G Q159N S164E A200N S217G D258N M260I S261H N270Q H374N (PhV-132) K12R L16V N33D D92N Q121T T152G Q159N S164E A200N S217G D258N M260I S261H N270Q H374N (PhV-133) N33D R67L D92N Q121T A123V T152G Q159N S164E A200N S217G D258N M260I S261H N270Q H374N (PhV-134) N33D D92N Q121T A144E T152G Q159N S164E A166E A200N S217G D258N M260I S261H N270Q H374N (PhV-135) N33D R67L D92N Q121T A123V A144E T152G Q159N S164E A166E A200N S217G D258N M260I S261H N270Q H374N (PhV-136) N33D D92A Q121T A123V A144E T152G Q159N S164E A166E A200N S217G D258N M260I S261H N270Q H374N (PhV-137) N33D D92A Q121T T152G Q159N S164E A166E A200N S217G D258N M260I S261H N270Q H374N D398E (PhV-138) N33D D92N Q121T A123V A144E T152G Q159N S164E A166E A200N S217G D258N M260I S261H N270Q H374N D398E (PhV-139) N33D D92N Q121T A144E T152G Q159N S164E A200N S217G D258N S261H N270Q H374N (PhV-140) K12R N33D R67L D92N Q121T A123V A144E T152G S164E A200N S217G D258N S261H N270Q H374N (PhV-141) L16V N33D R67L D92N Q121T A123V A144E T152G S164E A200N S217G D258N S261H N270Q H374N (PhV-142) N33D R67L D92N Q121T A123V A144E T152G S164E A166E A200N S217G D258N S261H N270Q H374N (PhV-143) N33D D92N Q121T A123V A144E T152G S164E A166E A200N S217G D258N S261H N270Q I300L H374N (PhV-144) N33D D92N I120L Q121T A123V A144E T152G S164E A200N S217G D258N S261H N270Q I300L H374N (PhV-145) N33D D92N I120L Q121T A123V A144E T152G S164E A200N S217G D258N S261H N270Q L371A H374N (PhV-146) N33D R67L D92N I120L Q121T A123V A144E T152G S164E A166E A200N S217G D258N S261H N270Q L371A H374N and (PhV-147) N33D D92N I120L Q121T A123V A144E T152G S164E A200N S217G D258N S261H N270Q I300L L371A H374N.

4. The phytase according to claim 2, which further has at least one conservative amino acid exchange at at least one position of said phytase.

5. The phytase according to claim 1, which is an isolated phytase.

6. The phytase according to claim 1, which has an elevated pepsin stability, an elevated thermostability and/or an elevated specific activity compared with wild-type phytases from *Yersinia mollaretii* and *Hafnia* sp.

7. The phytase according to claim 1, wherein the amino acids are unmodified at positions R18, H19, G20, R22, P24, H306, and D307 over SEQ ID NO: 24.

8. An isolated nucleic acid comprising a nucleic acid sequence coding for a phytase, which codes for encoding the phytase according to claim 1.

9. A recombinant expression vector comprising the nucleic acid according to claim 8.

10. A recombinant host cell comprising the nucleic acid according to claim 8 or a vector comprising said nucleic acid.

11. A recombinant production organism comprising the nucleic acid according to claim 8 or a vector comprising said nucleic acid.

12. An animal feed additive comprising the phytase according to claim 1 and further feed additives.

13. An animal feed comprising the phytase according to claim 1.

14. A method for preparing an animal feed comprising adding the phytase of claim 1 or an animal feed additive comprising said phytase to feed components before or after pelleting the feed components.

15. A method for reducing the phosphate content in the slurry of livestock comprising feeding livestock animal feed comprising the phytase of claim 1.

16. The phytase according to claim 1, which has the following cumulative modifications: (PhV-099) D2E A4E A6S F8Y N33D K76N N78T D92N Q121T T152G S164E A200N D258N S261H N270Q H374N.

17. An animal feed comprising the phytase according to claim 16.

18. A method for reducing the phosphate content in the slurry of livestock, comprising feeding livestock the animal feed of claim 17.

* * * * *

SEQUENCE LISTING

<160> NUMBER OF SEQ ID NOS: 26

<210> SEQ ID NO 1
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 1
gayccnytnt tycaycc        17

<210> SEQ ID NO 2
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 2
ggngtrttrt cnggytg        17

<210> SEQ ID NO 3
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n is a, c, g, or t

<400> SEQUENCE: 3
gcdatrttng trtcrtg        17

<210> SEQ ID NO 4
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 4
wcagntgwtn gtnctg        16

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
cttcgagagc cactttatta ccgtcg        26

<210> SEQ ID NO 6
<211> LENGTH: 25
<212> TYPE: DNA
<213> ORGANISM: Artificial Sequence

```
<220> FEATURE:
<223> OTHER INFORMATION: Primer

<400> SEQUENCE: 6
ccaatgttgt gctgctgaca atagg                                             25

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
ccgaactcat cagcgctaaa gatgc                                             25

<210> SEQ ID NO 8
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (8)..(8)
<223> OTHER INFORMATION: n is a, c, g, or t

<400> SEQUENCE: 8
cawcgwcnga sasgaa                                                       16

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
cgcagtttga cttgatgtcg cgcacg                                            26

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
gtcgcgcacg ccctatatcg ccaagc                                            26

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
ctgcaaacca tcgcacacgc actgg                                             25

<210> SEQ ID NO 12
<211> LENGTH: 1341
<212> TYPE: DNA
<213> ORGANISM: Hafnia sp.
<220> FEATURE:
<221> NAME/KEY: sig_peptide
<222> LOCATION: (1)..(99)
```

```
<400> SEQUENCE: 12
atgacaatct ctctgtttaa ccgtaataaa cccgctattg cacagcgtat tttatgtcct      60
ctgatcgtgg ctttattctc aggtttaccg gcatacgcca gtgataccgc ccctgctggg     120
ttccagttgg aaaaggttgt tatcctaagc agacatggcg tacgcgcgcc aaccaaaatg     180
acacaaacga tgcgcaacgt cacacctcac cagtggcctg aatggccggt aaaactcggc     240
tatatcacgc cccgcggtga acatctgatt agcctgatgg gcggttttta tcgagagcgc     300
tttcagcaac aaggcttatt acctaaggat aactgtccta caccagatgc cgtgtatgtt     360
tgggcagacg tcgatcaacg cacacgtaaa accggcgagg ccttcttagc gggtcttgct     420
ccccagtgtg atttagcgat ccaccatcag caaaacattc agcaggccga tccgctgttc     480
catcctgtga agccggtat ctgttcgatg gataaatcac aggcacacgc cgccgttgaa      540
aagcaggcag gcacaccgat tgagacgctc aatcaacgct atcaagcatc tttagcgctg     600
atgagttcgg tactcgattt tccaaaatcc ccctattgtc agcagcacaa cattggcaaa     660
ctctgcgatt tttcacaggc gatgcctagc aggctggcga taaatgacga cggtaataaa     720
gtggctctcg aaggtgccgt gggactttca tcgacgttgg ctgaaatttt cctgctggaa     780
cacgctcagg gaatgcctaa agtggcttgg gggaatattc acactgagca gcaatgggac     840
tctctgttaa aattgcataa tgcgcagttt gacttgatgt cgcgcacgcc ctatatcgcc     900
aagcataacg gtactccact gctgcaaacc atcgcacacg cactgggttc caatatcgcg     960
agtcgcccac tgccggatat ttcgccagac aataagatcc tgtttattgc cggtcacgac    1020
accaatattg ccaatatttc tggcatgcta gggatgacat ggacacttcc gggacagcca    1080
gataacacgc ctccgggcgg ggctttagtg tttgaacgtt gggtagataa cgcggggaaa    1140
ccgtatgtta gcgtgaatat ggtgtatcaa acactggcac agttgcacga ccagacgccg    1200
ctaacgttgc agcatcctgc gggcagcgta cgactaaaca taccggggttg cagcgatcaa    1260
acgcccgatg gctattgccc gctctccacc ttcagccgtt tagtcaacca cagcgttgag    1320
cctgcgtgcc agcttcctta a                                             1341

<210> SEQ ID NO 13
<211> LENGTH: 446
<212> TYPE: PRT
<213> ORGANISM: Hafnia sp.
<220> FEATURE:
<221> NAME/KEY: SIGNAL
<222> LOCATION: (1)..(33)

<400> SEQUENCE: 13

Met Thr Ile Ser Leu Phe Asn Arg Asn Lys Pro Ala Ile Ala Gln Arg
1               5                   10                  15

Ile Leu Cys Pro Leu Ile Val Ala Leu Phe Ser Gly Leu Pro Ala Tyr
                20                  25                  30

Ala Ser Asp Thr Ala Pro Ala Gly Phe Gln Leu Glu Lys Val Val Ile
            35                  40                  45

Leu Ser Arg His Gly Val Arg Ala Pro Thr Lys Met Thr Gln Thr Met
        50                  55                  60

Arg Asn Val Thr Pro His Gln Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Glu Arg Phe Gln Gln Gln Gly Leu Leu Pro Lys Asp Asn Cys
```

```
            100                 105                 110
Pro Thr Pro Asp Ala Val Tyr Val Trp Ala Asp Val Asp Gln Arg Thr
                115                 120                 125

Arg Lys Thr Gly Glu Ala Phe Leu Ala Gly Leu Ala Pro Gln Cys Asp
        130                 135                 140

Leu Ala Ile His His Gln Gln Asn Ile Gln Gln Ala Asp Pro Leu Phe
145                 150                 155                 160

His Pro Val Lys Ala Gly Ile Cys Ser Met Asp Lys Ser Gln Ala His
                165                 170                 175

Ala Ala Val Glu Lys Gln Ala Gly Thr Pro Ile Glu Thr Leu Asn Gln
            180                 185                 190

Arg Tyr Gln Ala Ser Leu Ala Leu Met Ser Ser Val Leu Asp Phe Pro
        195                 200                 205

Lys Ser Pro Tyr Cys Gln Gln His Asn Ile Gly Lys Leu Cys Asp Phe
    210                 215                 220

Ser Gln Ala Met Pro Ser Arg Leu Ala Ile Asn Asp Asp Gly Asn Lys
225                 230                 235                 240

Val Ala Leu Glu Gly Ala Val Gly Leu Ser Ser Thr Leu Ala Glu Ile
                245                 250                 255

Phe Leu Leu Glu His Ala Gln Gly Met Pro Lys Val Ala Trp Gly Asn
            260                 265                 270

Ile His Thr Glu Gln Gln Trp Asp Ser Leu Leu Lys Leu His Asn Ala
        275                 280                 285

Gln Phe Asp Leu Met Ser Arg Thr Pro Tyr Ile Ala Lys His Asn Gly
    290                 295                 300

Thr Pro Leu Leu Gln Thr Ile Ala His Ala Leu Gly Ser Asn Ile Ala
305                 310                 315                 320

Ser Arg Pro Leu Pro Asp Ile Ser Pro Asp Asn Lys Ile Leu Phe Ile
                325                 330                 335

Ala Gly His Asp Thr Asn Ile Ala Asn Ile Ser Gly Met Leu Gly Met
            340                 345                 350

Thr Trp Thr Leu Pro Gly Gln Pro Asp Asn Thr Pro Pro Gly Gly Ala
        355                 360                 365

Leu Val Phe Glu Arg Trp Val Asp Asn Ala Gly Lys Pro Tyr Val Ser
    370                 375                 380

Val Asn Met Val Tyr Gln Thr Leu Ala Gln Leu His Asp Gln Thr Pro
385                 390                 395                 400

Leu Thr Leu Gln His Pro Ala Gly Ser Val Arg Leu Asn Ile Pro Gly
                405                 410                 415

Cys Ser Asp Gln Thr Pro Asp Gly Tyr Cys Pro Leu Ser Thr Phe Ser
            420                 425                 430

Arg Leu Val Asn His Ser Val Glu Pro Ala Cys Gln Leu Pro
        435                 440                 445

<210> SEQ ID NO 14
<211> LENGTH: 1074
<212> TYPE: DNA
<213> ORGANISM: Hafnia sp.

<400> SEQUENCE: 14
atgacaatct ctctgtttaa ccgtaataaa cccgctattg cacagcgtat tttatgtcct      60
ctgatcgtgg ctttattctc aggtttaccg gcatacgcca gtgataccgc ccctgctggg     120
ttccagttgg aaaaggttgt tatcctaagc agacatggcg tacgcgcgcc aaccaaaatg     180
```

```
acacaaacga tgcgcaacgt cacacctcac cagtggcctg aatggccggt aaaactcggc    240
tatatcacgc cccgcggtga acatctgatt agcctgatgg gcggttttta tcgagagcgc    300
tttcagcaac aaggcttatt acctaaggat aactgtccta caccagatgc cgtgtatgtt    360
tgggcagacg tcgatcaacg cacacgtaaa accggcgagg ccttcttagc gggtcttgct    420
ccccagtgtg atttagcgat ccaccatcag caaaacattc agcaggccga tccgctgttc    480
catcctgtga aagccggtat ctgttcgatg gataaatcac aggcacacgc cgccgttgaa    540
aagcaggcag gcacaccgat tgagacgctc aatcaacgct atcaagcatc tttagcgctg    600
atgagttcgg tactcgattt tccaaaatcc cctattgtc agcagcacaa cattggcaaa     660
ctctgcgatt tttcacaggc gatgcctagc aggctggcga taaatgacga cggtaataaa    720
gtggctctcg aaggtgccgt gggactttca tcgacgttgg ctgaaatttt cctgctggaa    780
cacgctcagg gaatgcctaa agtggcttgg gggaatattc acactgagca gcaatgggac    840
tctctgttaa aattgcataa tgcgcagttt gacttgatgt cgcgcacgcc ctatatcgcc    900
aagcataacg gtactccact gctgcaaacc atcgcacacg cactgggttc caatatcgcg    960
agtcgcccac tgccggatat ttcgccagac aataagatcc tgtttattgc cggtcacgac   1020
accaatattg ccaatatttc tggcatgcta gggatgacat ggacacttcc ggga         1074

<210> SEQ ID NO 15
<211> LENGTH: 270
<212> TYPE: DNA
<213> ORGANISM: Yersinia mollaretii

<400> SEQUENCE:

```
aagcaggcag gcacaccgat tgagacgctc aatcaacgct atcaagcatc tttagcgctg     600
atgagttcgg tactcgattt tccaaaatcc ccctattgtc agcagcacaa cattggcaaa     660
ctctgcgatt tttcacaggc gatgcctagc aggctggcga taaatgacga cggtaataaa     720
gtggctctcg aaggtgccgt gggactttca tcgacgttgg ctgaaatttt cctgctggaa     780
cacgctcagg gaatgcctaa agtggcttgg gggaatattc acactgagca gcaatgggac     840
tctctgttaa aattgcataa tgcgcagttt gacttgatgt cgcgcacgcc ctatatcgcc     900
aagcataacg gtactccact gctgcaaacc atcgcacacg cactgggttc caatatcgcg     960
agtcgcccac tgccggatat ttcgccagac aataagatcc tgtttattgc cggtcacgac    1020
accaatattg ccaatatttc tggcatgcta gggatgacat ggacacttcc gggacagccc    1080
gataacaccc cgccgggtgg ggggctggtg tttgaactat ggcagaatcc agataaccat    1140
cagcaatatg tcgcagttaa gatgttctat caaacaatgg atcagttacg aaatagtgaa    1200
aagttagacc tgaaaagtca tccagccggt attgttccca ttgagatcga aggttgtgag    1260
aacatcggta cagacaaact tgccagcttg gataccttcc aaaagagagt ggctcaggtg    1320
attgaacctg catgccatat ttaa                                          1344
```

<210> SEQ ID NO 17  
<211> LENGTH: 447  
<212> TYPE: PRT  
<213> ORGANISM: Artificial Sequence  
<220> FEATURE:  
<223> OTHER INFORMATION: synthetic construct  
<220> FEATURE:  
<221> NAME/KEY: SIGNAL  
<222> LOCATION: (1)..(33)

<400> SEQUENCE: 17

```
Met Thr Ile Ser Leu Phe Asn Arg Asn Lys Pro Ala Ile Ala Gln Arg
 1               5                  10                  15

Ile Leu Cys Pro Leu Ile Val Ala Leu Phe Ser Gly Leu Pro Ala Tyr
            20                  25                  30

Ala Ser Asp Thr Ala Pro Ala Gly Phe Gln Leu Glu Lys Val Val Ile
        35                  40                  45

Leu Ser Arg His Gly Val Arg Ala Pro Thr Lys Met Thr Gln Thr Met
    50                  55                  60

Arg Asn Val Thr Pro His Gln Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Glu Arg Phe Gln Gln Gln Gly Leu Leu Pro Lys Asp Asn Cys
            100                 105                 110

Pro Thr Pro Asp Ala Val Tyr Val Trp Ala Asp Val Asp Gln Arg Thr
        115                 120                 125

Arg Lys Thr Gly Glu Ala Phe Leu Ala Gly Leu Ala Pro Gln Cys Asp
    130                 135                 140

Leu Ala Ile His His Gln Gln Asn Ile Gln Gln Ala Asp Pro Leu Phe
145                 150                 155                 160

His Pro Val Lys Ala Gly Ile Cys Ser Met Asp Lys Ser Gln Ala His
                165                 170                 175

Ala Ala Val Glu Lys Gln Ala Gly Thr Pro Ile Glu Thr Leu Asn Gln
            180                 185                 190

Arg Tyr Gln Ala Ser Leu Ala Leu Met Ser Ser Val Leu Asp Phe Pro
        195                 200                 205
```

```
Lys Ser Pro Tyr Cys Gln Gln His Asn Ile Gly Lys Leu Cys Asp Phe
    210                 215                 220

Ser Gln Ala Met Pro Ser Arg Leu Ala Ile Asn Asp Asp Gly Asn Lys
225                 230                 235                 240

Val Ala Leu Glu Gly Ala Val Gly Leu Ser Ser Thr Leu Ala Glu Ile
                245                 250                 255

Phe Leu Leu Glu His Ala Gln Gly Met Pro Lys Val Ala Trp Gly Asn
            260                 265                 270

Ile His Thr Glu Gln Gln Trp Asp Ser Leu Leu Lys Leu His Asn Ala
        275                 280                 285

Gln Phe Asp Leu Met Ser Arg Thr Pro Tyr Ile Ala Lys His Asn Gly
    290                 295                 300

Thr Pro Leu Leu Gln Thr Ile Ala His Ala Leu Gly Ser Asn Ile Ala
305                 310                 315                 320

Ser Arg Pro Leu Pro Asp Ile Ser Pro Asp Asn Lys Ile Leu Phe Ile
                325                 330                 335

Ala Gly His Asp Thr Asn Ile Ala Asn Ile Ser Gly Met Leu Gly Met
            340                 345                 350

Thr Trp Thr Leu Pro Gly Gln Pro Asp Asn Thr Pro Pro Gly Gly Gly
        355                 360                 365

Leu Val Phe Glu Leu Trp Gln Asn Pro Asp Asn His Gln Gln Tyr Val
    370                 375                 380

Ala Val Lys Met Phe Tyr Gln Thr Met Asp Gln Leu Arg Asn Ser Glu
385                 390                 395                 400

Lys Leu Asp Leu Lys Ser His Pro Ala Gly Ile Val Pro Ile Glu Ile
                405                 410                 415

Glu Gly Cys Glu Asn Ile Gly Thr Asp Lys Leu Cys Gln Leu Asp Thr
            420                 425                 430

Phe Gln Lys Arg Val Ala Gln Val Ile Glu Pro Ala Cys His Ile
        435                 440                 445

<210> SEQ ID NO 18
<211> LENGTH: 414
<212> TYPE: PRT
<213> ORGANISM: Artificial Sequence
<220> FEATURE:
<223> OTHER INFORMATION: chimeric protein

<400> SEQUENCE: 18

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
                20                  25                  30

Asn Val Thr Pro His Gln Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Ala Asp Val Asp Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Gln Gln Ala Asp Pro Leu Phe His
        115                 120                 125
```

Pro Val Lys Ala Gly Ile Cys Ser Met Asp Lys Ser Gln Ala His Ala
         130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Ala Ile Asn Asp Asp Gly Asn Lys Val
        195                 200                 205

Ala Leu Glu Gly Ala Val Gly Leu Ser Ser Thr Leu Ala Glu Ile Phe
    210                 215                 220

Leu Leu Glu His Ala Gln Gly Met Pro Lys Val Ala Trp Gly Asn Ile
225                 230                 235                 240

His Thr Glu Gln Gln Trp Asp Ser Leu Leu Lys Leu His Asn Ala Gln
                245                 250                 255

Phe Asp Leu Met Ser Arg Thr Pro Tyr Ile Ala Lys His Asn Gly Thr
            260                 265                 270

Pro Leu Leu Gln Thr Ile Ala His Ala Leu Gly Ser Asn Ile Ala Ser
        275                 280                 285

Arg Pro Leu Pro Asp Ile Ser Pro Asn Lys Ile Leu Phe Ile Ala
    290                 295                 300

Gly His Asp Thr Asn Ile Ala Asn Ile Ser Gly Met Leu Gly Met Thr
305                 310                 315                 320

Trp Thr Leu Pro Gly Gln Pro Asp Asn Thr Pro Pro Gly Gly Gly Leu
                325                 330                 335

Val Phe Glu Leu Trp Gln Asn Pro Asp Asn His Gln Gln Tyr Val Ala
            340                 345                 350

Val Lys Met Phe Tyr Gln Thr Met Asp Gln Leu Arg Asn Ser Glu Lys
        355                 360                 365

Leu Asp Leu Lys Ser His Pro Ala Gly Ile Val Pro Ile Glu Ile Glu
    370                 375                 380

Gly Cys Glu Asn Ile Gly Thr Asp Lys Leu Cys Gln Leu Asp Thr Phe
385                 390                 395                 400

Gln Lys Arg Val Ala Gln Val Ile Glu Pro Ala Cys His Ile
                405                 410

<210> SEQ ID NO 19
<211> LENGTH: 1245
<212> TYPE: DNA
<213> ORGANISM: Artificial Sequence
<220> FEATURE:
<223> OTHER INFORMATION: synthetic construct

<400> SEQUENCE: 19
agtgataccg cccctgctgg gttccagttg gaaaaggttg ttatcctaag cagacatggc    60
gtacgcgcgc aaccaaaat gacacaaacg atgcgcaacg tcacacctca ccagtggcct   120
gaatggccgg taaaactcgg ctatatcacg ccccgcggtg aacatctgat tagcctgatg   180
ggcggttttt atcgagagcg ctttcagcaa caaggcttat tacctaagga taactgtcct   240
acaccagatg ccgtgtatgt ttgggcagac gtcgatcaac gcacacgtaa aaccggcgag   300
gccttcttag cgggtcttgc tccccagtgt gatttagcga tccaccatca gcaaaacatt   360
cagcaggccg atccgctgtt ccatcctgtg aaagccggta tctgttcgat ggataaatca   420

| | |
|---|---|
| caggcacacg ccgccgttga aaagcaggca ggcacaccga ttgagacgct caatcaacgc | 480 |
| tatcaagcat ctttagcgct gatgagttcg gtactcgatt ttccaaaatc cccctattgt | 540 |
| cagcagcaca acattggcaa actctgcgat ttttcacagg cgatgcctag caggctggcg | 600 |
| ataaatgacg acgtaataa agtggctctc gaaggtgccg tgggactttc atcgacgttg | 660 |
| gctgaaattt tcctgctgga acacgctcag ggaatgccta aagtggcttg ggggaatatt | 720 |
| cacactgagc agcaatggga ctctctgtta aaattgcata atgcgcagtt tgacttgatg | 780 |
| tcgcgcacgc cctatatcgc caagcataac ggtactccac tgctgcaaac catcgcacac | 840 |
| gcactgggtt ccaatatcgc gagtcgccca ctgccggata tttcgccaga caataagatc | 900 |
| ctgtttattg ccggtcacga caccaatatt gccaatattt ctggcatgct agggatgaca | 960 |
| tggacacttc cgggacagcc cgataacacc ccgccgggtg gggggctggt gtttgaacta | 1020 |
| tggcagaatc cagataacca tcagcaatat gtcgcagtta agatgttcta tcaaacaatg | 1080 |
| gatcagttac gaaatagtga aaagttagac ctgaaaagtc atccagccgg tattgttccc | 1140 |
| attgagatcg aaggttgtga gaacatcggt acagacaaac tttgccagct tgataccttc | 1200 |
| caaaagagag tggctcaggt gattgaacct gcatgccata tttaa | 1245 |

<210> SEQ ID NO 20
<211> LENGTH: 6729
<212> TYPE: DNA
<213> ORGANISM: Artificial Sequence
<220> FEATURE:
<223> OTHER INFORMATION: synthetic construct

<400> SEQUENCE: 20

| | |
|---|---|
| agcttgcggc cgcactcgag caccaccacc accaccactg agatccggct gctaacaaag | 60 |
| cccgaaagga agctgagttg gctgctgcca ccgctgagca ataactagca taaccccttg | 120 |
| gggcctctaa acgggtcttg aggggttttt tgctgaaagg aggaactata tccggattgg | 180 |
| cgaatgggac gcgccctgta gcggcgcatt aagcgcggcg ggtgtggtgg ttacgcgcag | 240 |
| cgtgaccgct acacttgcca gcgccctagc gcccgctcct ttcgctttct tcccttcctt | 300 |
| tctcgccacg ttcgccggct ttccccgtca agctctaaat cggggggctcc ctttagggtt | 360 |
| ccgatttagt gctttacggc acctcgaccc caaaaaactt gattagggtg atggttcacg | 420 |
| tagtgggcca tcgccctgat agacggtttt tcgccctttg acgttggagt ccacgttctt | 480 |
| taatagtgga ctcttgttcc aaactggaac aacactcaac cctatctcgg tctattcttt | 540 |
| tgatttataa gggattttgc cgatttcggc ctattggtta aaaaatgagc tgatttaaca | 600 |
| aaaatttaac gcgaatttta acaaaatatt aacgtttaca atttcaggtg gcacttttcg | 660 |
| gggaaatgtg cgcggaaccc ctatttgttt attttctaa atacattcaa atatgtatcc | 720 |
| gctcatgaga caataaccct gataaatgct tcaataatat tgaaaaagga agagtatgag | 780 |
| tattcaacat ttccgtgtcg cccttattcc cttttttgcg gcattttgcc ttcctgtttt | 840 |
| tgctcaccca gaaacgctgg tgaaagtaaa agatgctgaa gatcagttgg gtgcacgagt | 900 |
| gggttacatc gaactggatc tcaacagcgg taagatcctt gagagttttc gccccgaaga | 960 |
| acgttttcca atgatgagca cttttaaagt tctgctatgt ggcgcggtat tatcccgtat | 1020 |
| tgacgccggg caagagcaac tcggtcgccg catacactat tctcagaatg acttggttga | 1080 |
| gtactcacca gtcacagaaa agcatcttac ggatggcatg acagtaagag aattatgcag | 1140 |
| tgctgccata accatgagtg ataacactgc ggccaactta cttctgacaa cgatcggagg | 1200 |
| accgaaggag ctaaccgctt ttttgcacaa catgggggat catgtaactc gccttgatcg | 1260 |

```
ttgggaaccg gagctgaatg aagccatacc aaacgacgag cgtgacacca cgatgcctgc    1320
agcaatggca acaacgttgc gcaaactatt aactggcgaa ctacttactc tagcttcccg    1380
gcaacaatta atagactgga tggaggcgga taaagttgca ggaccacttc tgcgctcggc    1440
ccttccggct ggctggttta ttgctgataa atctggagcc ggtgagcgtg ggtctcgcgg    1500
tatcattgca gcactggggc cagatggtaa gccctcccgt atcgtagtta tctacacgac    1560
ggggagtcag gcaactatgg atgaacgaaa tagacagatc gctgagatag gtgcctcact    1620
gattaagcat tggtaactgt cagaccaagt ttactcatat atactttaga ttgatttaaa    1680
acttcatttt taatttaaaa ggatctaggt gaagatcctt tttgataatc tcatgaccaa    1740
aatcccttaa cgtgagtttt cgttccactg agcgtcagac cccgtagaaa agatcaaagg    1800
atcttcttga tccttttttt tctgcgcgt aatctgctgc ttgcaaacaa aaaaaccacc    1860
gctaccagcg gtggtttgtt tgccggatca agagctacca actctttttc cgaaggtaac    1920
tggcttcagc agagcgcaga taccaaatac tgtccttcta gtgtagccgt agttaggcca    1980
ccacttcaag aactctgtag caccgcctac atacctcgct ctgctaatcc tgttaccagt    2040
ggctgctgcc agtggcgata gtcgtgtct taccggggttg gactcaagac gatagttacc    2100
ggataaggcg cagcggtcgg gctgaacggg gggttcgtgc acacagccca gcttggagcg    2160
aacgacctac accgaactga gatacctaca gcgtgagcta tgagaaagcg ccacgcttcc    2220
cgaagggaga aaggcggaca ggtatccggt aagcggcagg gtcggaacag gagagcgcac    2280
gagggagctt ccaggggaa acgcctggta tctttatagt cctgtcgggt ttcgccacct    2340
ctgacttgag cgtcgatttt tgtgatgctc gtcaggggg cggagcctat ggaaaaacgc    2400
cagcaacgcg gcctttttac ggttcctggc cttttgctgg cctttttgctc acatgttctt    2460 tcctgcgtta tcccctgatt ctgtggataa ccgtattacc gcctttgagt gagctgatac    2520
cgctcgccgc agccgaacga ccgagcgcag cgagtcagtg agcgaggaag cggaagagcg    2580
cctgatgcgg tattttctcc ttacgcatct gtgcggtatt tcacaccgca tatatggtgc    2640
actctcagta caatctgctc tgatgccgca tagttaagcc agtatacact ccgctatcgc    2700
tacgtgactg ggtcatggct gcgccccgac acccgccaac acccgctgac gcgccctgac    2760
gggcttgtct gctcccggca tccgcttaca gacaagctgt gaccgtctcc gggagctgca    2820
tgtgtcagag gttttcaccg tcatcaccga acgcgcgag gcagctgcgg taaagctcat    2880
cagcgtggtc gtgaagcgat tcacagatgt ctgcctgttc atccgcgtcc agctcgttga    2940
gtttctccag aagcgttaat gtctggcttc tgataaagcg ggccatgtta agggcggttt    3000
tttcctgttt ggtcactgat gcctccgtgt aagggggatt tctgttcatg ggggtaatga    3060
taccgatgaa acgagagagg atgctcacga tacgggttac tgatgatgaa catgcccggt    3120
tactggaacg ttgtgagggt aaacaactgg cggtatggat gcggcgggac cagagaaaaa    3180
tcactcaggg tcaatgccag cgcttcgtta atacagatgg aggtgttcca cagggtagcc    3240
agcagcatcc tgcgatgcag atccggaaca taatggtgca gggcgctgac ttccgcgttt    3300
ccagacttta cgaaacacgg aaaccgaaga ccattcatgt tgttgctcag gtcgcagacg    3360
ttttgcagca gcagtcgctt cacgttcgct cgcgtatcgg tgattcattc tgctaaccag    3420
taaggcaacc ccgccagcct agccgggtcc tcaacgacag gagcacgatc atgcgcaccc    3480
gtggggccgc catgccggcg ataatggcct gcttctcgcc gaaacgtttg gtggcgggac    3540
cagtgacgaa ggcttgagcg agggcgtgca agattccgaa taccgcaagc gacaggccga    3600
```

```
tcatcgtcgc gctccagcga aagcggtcct cgccgaaaat gacccagagc gctgccggca    3660
cctgtcctac gagttgcatg ataaagaaga cagtcataag tgcggcgacg atagtcatgc    3720
cccgcgccca ccggaaggag ctgactgggt tgaaggctct caagggcatc ggtcgagatc    3780
ccggtgccta atgagtgagc taacttacat taattgcgtt gcgctcactg cccgctttcc    3840
agtcgggaaa cctgtcgtgc cagctgcatt aatgaatcgg ccaacgcgcg gggagaggcg    3900
gtttgcgtat tgggcgccag ggtggttttt cttttcacca gtgagacggg caacagctga    3960
ttgcccttca ccgcctggcc ctgagagagt tgcagcaagc ggtccacgct ggtttgcccc    4020
agcaggcgaa aatcctgttt gatggtggtt aacggcggga tataacatga gctgtcttcg    4080
gtatcgtcgt atcccactac cgagatatcc gcaccaacgc gcagcccgga ctcggtaatg    4140
gcgcgcattg cgcccagcgc catctgatcg ttggcaacca gcatcgcagt gggaacgatg    4200
ccctcattca gcatttgcat ggtttgttga aaccggaca tggcactcca gtcgccttcc     4260
cgttccgcta tcggctgaat ttgattgcga gtgagatatt tatgccagcc agccagacgc    4320
agacgcgccg agacagaact taatgggccc gctaacagcg cgatttgctg gtgacccaat    4380
gcgaccagat gctccacgcc cagtcgcgta ccgtcttcat gggagaaaat aatactgttg    4440
atgggtgtct ggtcagagac atcaagaaat aacgccggaa cattagtgca ggcagcttcc    4500
acagcaatgg catcctggtc atccagcgga tagttaatga tcagcccact gacgcgttgc    4560
gcgagaagat tgtgcaccgc cgctttacag gcttcgacgc cgcttcgttc taccatcgac    4620
accaccacgc tggcacccag ttgatcggcg cgagatttaa tcgccgcgac aatttgcgac    4680
ggcgcgtgca gggccagact ggaggtggca acgccaatca gcaacgactg tttgcccgcc    4740
agttgttgtg ccacgcggtt gggaatgtaa ttcagctccg ccatcgccgc ttccactttt    4800
tcccgcgttt tcgcagaaac gtggctggcc tggttcacca cgcgggaaac ggtctgataa    4860
gagacaccgg catactctgc gacatcgtat aacgttactg gtttcacatt caccaccctg    4920
aattgactct cttccgggcg ctatcatgcc ataccgcgaa aggttttgcg ccattcgatg    4980
gtgtccggga tctcgacgct ctcccttatg cgactcctgc attaggaagc agcccagtag    5040
taggttgagg ccgttgagca ccgccgccgc aaggaatggt gcatgcaagg agatggcgcc    5100
caacagtccc ccggccacgg ggcctgccac catacccacg ccgaaacaag cgctcatgag    5160
cccgaagtgg cgagcccgat cttccccatc ggtgatgtcg gcgatatagg cgccagcaac    5220
cgcacctgtg gcgccggtga tgccggccac gatgcgtccg gcgtagagga tcgagatctc    5280
gatcccgcga aattaatacg actcactata ggggaattgt gagcggataa caattcccct    5340
ctagaaataa ttttgtttaa ctttaagaag gagatataca tatgatgaca atctctctgt    5400
ttaaccgtaa taaacccgct attgcacagc gtattttatg tcctctgatc gtggctttat    5460
tctcaggttt accggcatac gccagtgata ccgcccctgc tgggttccag ttggaaaagg    5520
ttgttatcct aagcagacat ggcgtacgcg cgccaaccaa aatgacacaa acgatgcgca    5580
acgtcacacc tcaccagtgg cctgaatggc cggtaaaact cggctatatc acgcccgcg    5640
gtgaacatct gattagcctg atgggcggtt tttatcgaga gcgctttcag caacaaggct    5700
tattacctaa ggataactgt cctacaccag atgccgtgta tgtttgggca gacgtcgatc    5760
aacgcacacg taaaccggc gaggccttct tagcgggtct tgctccccag tgtgatttag    5820
cgatccacca tcagcaaaac attcagcagg ccgatccgct gttccatcct gtgaaagccg    5880
gtatctgttc gatggataaa tcacaggcac acgccgccgt tgaaaagcag gcaggcacac    5940
cgattgagac gctcaatcaa cgctatcaag catctttagc gctgatgagt tcggtactcg    6000
```

-continued

```
attttccaaa atcccctat tgtcagcagc acaacattgg caaactctgc gattttcac      6060 aggcgatgcc tagcaggctg gcgataaatg acgacggtaa taaagtggct ctcgaaggtg      6120
ccgtgggact ttcatcgacg ttggctgaaa ttttcctgct ggaacacgct cagggaatgc      6180
ctaaagtggc ttgggggaat attcacactg agcagcaatg ggactctctg ttaaaattgc      6240
ataatgcgca gtttgacttg atgtcgcgca cgccctatat cgccaagcat aacggtactc      6300
cactgctgca aaccatcgca cacgcactgg gttccaatat cgcgagtcgc ccactgccgg      6360
atatttcgcc agacaataag atcctgttta ttgccggtca cgacaccaat attgccaata      6420
tttctggcat gctagggatg acatggacac ttccgggaca gcccgataac accccgccgg      6480 gtgggggggct ggtgtttgaa ctatggcaga atccagataa ccatcagcaa tatgtcgcag      6540
ttaagatgtt ctatcaaaca atggatcagt tacgaaatag tgaaaagtta gacctgaaaa      6600
gtcatccagc cggtattgtt cccattgaga tcgaaggttg tgagaacatc ggtacagaca      6660
aactttgcca gcttgatacc ttccaaaaga gagtggctca ggtgattgaa cctgcatgcc      6720
atatttaaa                                                              6729
```

<210> SEQ ID NO 21
<211> LENGTH: 46
<212> TYPE: DNA
<213> ORGANISM: Artificial Sequence
<220> FEATURE:
<223> OTHER INFORMATION: primer

<400> SEQUENCE: 21

```
ctatggatcc gcatcatcat catcatcaca gtgataccgc ccctgc                      46
```

<210> SEQ ID NO 22
<211> LENGTH: 6738
<212> TYPE: DNA
<213> ORGANISM: Artificial Sequence
<220> FEATURE:
<223> OTHER INFORMATION: synthetic construct

<400> SEQUENCE: 22

```
gagatataca tatgaaatac ctgctgccga ccgctgctgc tggtctgctg ctcctcgctg       60
cccagccggc gatggccatg gatatcggaa ttaattcgga tccgcatcat catcatcatc      120
acagtgatac cgcccctgct gggttccagt tggaaaaggt tgttatccta agcagacatg      180
gcgtacgcgc gccaaccaaa atgacacaaa cgatgcgcaa cgtcacacct caccagtggc      240
ctgaatggcc ggtaaaactc ggctatatca cgccccgcgg tgaacatctg attagcctga      300
tgggcggttt ttatcgagag cgctttcagc aacaaggctt attacctaag gataactgtc      360
ctacaccaga tgccgtgtat gtttgggcag acgtcgatca acgcacacgt aaaaccggcg      420
aggccttctt agcgggtctt gctccccagt gtgatttagc gatccaccat cagcaaaaca      480
ttcagcaggc cgatccgctg ttccatcctg tgaaagccgg tatctgttcg atggataaat      540
cacaggcaca cgccgccgtt gaaaagcagg caggcacacc gattgagacg ctcaatcaac      600
gctatcaagc atctttagcg ctgatgagtt cggtactcga ttttccaaaa tcccctatt       660 gtcagcagca caacattggc aaactctgcg attttcaca ggcgatgcct agcaggctgg       720
cgataaatga cgacggtaat aaagtggctc tcgaaggtgc cgtgggactt tcatcgacgt      780
tggctgaaat tttcctgctg gaacacgctc agggaatgcc taaagtggct tgggggaata      840
ttcacactga gcagcaatgg gactctctgt taaaattgca taatgcgcag tttgacttga      900
```

```
tgtcgcgcac gccctatatc gccaagcata acggtactcc actgctgcaa accatcgcac    960
acgcactggg ttccaatatc gcgagtcgcc cactgccgga tatttcgcca gacaataaga   1020
tcctgtttat tgccggtcac gacaccaata ttgccaatat ttctggcatg ctagggatga   1080
catggacact tccgggacag cccgataaca ccccgccggg tgggggggctg gtgtttgaac  1140
tatggcagaa tccagataac catcagcaat atgtcgcagt taagatgttc tatcaaacaa   1200
tggatcagtt acgaaatagt gaaaagttag acctgaaaag tcatccagcc ggtattgttc   1260
ccattgagat cgaaggttgt gagaacatcg gtacagacaa actttgccag cttgatacct   1320
tccaaaagag agtggctcag gtgattgaac ctgcatgcca tatttaaaag cttgcggccg   1380
cactcgagca ccaccaccac caccactgag atccggctgc taacaaagcc cgaaaggaag   1440
ctgagttggc tgctgccacc gctgagcaat aactagcata acccttgggg cctctaaac    1500
gggtcttgag gggttttttg ctgaaaggag gaactatatc cggattggcg aatgggacgc   1560
gccctgtagc ggcgcattaa gcgcggcggg tgtggtggtt acgcgcagcg tgaccgctac   1620
acttgccagc gccctagcgc ccgctccttt cgctttcttc ccttcctttc tcgccacgtt   1680
cgccggcttt ccccgtcaag ctctaaatcg ggggctccct ttagggttcc gatttagtgc   1740
tttacggcac ctcgacccca aaaaacttga ttagggtgat ggttcacgta gtgggccatc   1800
gccctgatag acggttttc gcccttgac gttggagtcc acgttcttta atagtggact   1860
cttgttccaa actggaacaa cactcaaccc tatctcggtc tattcttttg atttataagg   1920
gattttgccg atttcggcct attggttaaa aaatgagctg atttaacaaa aatttaacgc   1980
gaattttaac aaaatattaa cgtttacaat ttcaggtggc acttttcggg gaaatgtgcg   2040
cggaacccct atttgtttat ttttctaaat acattcaaat atgtatccgc tcatgagaca   2100
ataaccctga taaatgcttc aataatattg aaaaaggaag agtatgagta ttcaacattt   2160
ccgtgtcgcc cttattccct ttttttgcggc attttgcctt cctgttttg ctcacccaga   2220
aacgctggtg aaagtaaaag atgctgaaga tcagttgggt gcacgagtgg gttacatcga   2280
actggatctc aacagcggta agatccttga gagttttcgc cccgaagaac gttttccaat   2340
gatgagcact tttaaagttc tgctatgtgg cgcggtatta tcccgtattg acgccgggca   2400
agagcaactc ggtcgccgca tacactattc tcagaatgac ttggttgagt actcaccagt   2460
cacagaaaag catcttacgg atggcatgac agtaagagaa ttatgcagtg ctgccataac   2520
catgagtgat aacactgcgg ccaacttact tctgacaacg atcggaggac cgaaggagct   2580
aaccgctttt ttgcacaaca tgggggatca tgtaactcgc cttgatcgtt gggaaccgga   2640
gctgaatgaa gccataccaa acgacgagcg tgacaccacg atgcctgcag caatggcaac   2700
aacgttgcgc aaactattaa ctggcgaact acttactcta gcttcccggc aacaattaat   2760
agactggatg gaggcggata agttgcagg accacttctg cgctcggccc ttccggctgg   2820
ctggtttatt gctgataaat ctggagccgg tgagcgtggg tctcgcggta tcattgcagc   2880
actggggcca gatggtaagc cctcccgtat cgtagttatc tacacgacgg ggagtcaggc   2940
aactatggat gaacgaaata gacagatcgc tgagataggt gcctcactga ttaagcattg   3000
gtaactgtca gaccaagttt actcatatat actttagatt gatttaaaac ttcattttta   3060
atttaaaagg atctaggtga agatcctttt tgataatctc atgaccaaaa tcccttaacg   3120
tgagttttcg ttccactgag cgtcagaccc cgtagaaaag atcaaaggat cttcttgaga   3180
tccttttttt ctgcgcgtaa tctgctgctt gcaaacaaaa aaaccaccgc taccagcggt   3240
ggtttgtttg ccggatcaag agctaccaac tcttttttccg aaggtaactg gcttcagcag   3300
```

```
agcgcagata ccaaatactg tccttctagt gtagccgtag ttaggccacc acttcaagaa   3360
ctctgtagca ccgcctacat acctcgctct gctaatcctg ttaccagtgg ctgctgccag   3420
tggcgataag tcgtgtctta ccgggttgga ctcaagacga tagttaccgg ataaggcgca   3480
gcggtcgggc tgaacggggg gttcgtgcac acagcccagc ttggagcgaa cgacctacac   3540
cgaactgaga tacctacagc gtgagctatg agaaagcgcc acgcttcccg aagggagaaa   3600
ggcggacagg tatccggtaa gcggcagggt cggaacagga gagcgcacga gggagcttcc   3660 aggggggaaac gcctggtatc tttatagtcc tgtcgggttt cgccacctct gacttgagcg   3720 tcgattttg tgatgctcgt caggggggcg gagcctatgg aaaaacgcca gcaacgcggc   3780 cttttacgg ttcctggcct tttgctggcc ttttgctcac atgttctttc ctgcgttatc   3840
ccctgattct gtggataacc gtattaccgc ctttgagtga gctgataccg ctcgccgcag   3900
ccgaacgacc gagcgcagcg agtcagtgag cgaggaagcg gaagagcgcc tgatgcggta   3960
ttttctcctt acgcatctgt gcggtatttc acaccgcata tatggtgcac tctcagtaca   4020
atctgctctg atgccgcata gttaagccag tatacactcc gctatcgcta cgtgactggg   4080
tcatggctgc gccccgacac ccgccaacac ccgctgacgc gccctgacgg gcttgtctgc   4140
tcccggcatc cgcttacaga caagctgtga ccgtctccgg gagctgcatg tgtcagaggt   4200
tttcaccgtc atcaccgaaa cgcgcgaggc agctgcggta aagctcatca gcgtggtcgt   4260
gaagcgattc acagatgtct gcctgttcat ccgcgtccag ctcgttgagt ttctccagaa   4320
gcgttaatgt ctggcttctg ataaagcggg ccatgttaag gcggttttt tcctgtttgg   4380 tcactgatgc ctccgtgtaa gggggatttc tgttcatggg ggtaatgata ccgatgaaac   4440
gagagaggat gctcacgata cgggttactg atgatgaaca tgcccggtta ctggaacgtt   4500
gtgagggtaa acaactggcg gtatggatgc ggcgggacca gagaaaaatc actcagggtc   4560
aatgccagcg cttcgttaat acagatgtag gtgttccaca gggtagccag cagcatcctg   4620
cgatgcagat ccggaacata atggtgcagg gcgctgactt ccgcgtttcc agactttacg   4680
aaacacggaa accgaagacc attcatgttg ttgctcaggt cgcagacgtt ttgcagcagc   4740
agtcgcttca cgttcgctcg cgtatcggtg attcattctg ctaaccagta aggcaacccc   4800
gccagcctag ccgggtcctc aacgacagga gcacgatcat gcgcacccgt ggggccgcca   4860
tgccggcgat aatggcctgc ttctcgccga acgtttggt ggcgggacca gtgacgaagg   4920
cttgagcgag ggcgtgcaag attccgaata ccgcaagcga caggccgatc atcgtcgcgc   4980
tccagcgaaa gcggtcctcg ccgaaaatga cccagagcgc tgccggcacc tgtcctacga   5040
gttgcatgat aaagaagaca gtcataagtg cggcgacgat agtcatgccc cgcgcccacc   5100
ggaaggagct gactgggttg aaggctctca agggcatcgg tcgagatccc ggtgcctaat   5160
gagtgagcta acttacatta attgcgttgc gctcactgcc cgctttccag tcgggaaacc   5220
tgtcgtgcca gctgcattaa tgaatcggcc aacgcgcggg gagaggcggt ttgcgtattg   5280
ggcgccaggg tggttttct tttcaccagt gagacgggca acagctgatt gcccttcacc   5340
gcctggccct gagagagttg cagcaagcgg tccacgctgg tttgccccag caggcgaaaa   5400
tcctgtttga tggtggttaa cggcgggata taacatgagc tgtcttcggt atcgtcgtat   5460
cccactaccg agatatccgc accaacgcgc agcccggact cggtaatggc gcgcattgcg   5520
cccagcgcca tctgatcgtt ggcaaccagc atcgcagtgg gaacgatgcc ctcattcagc   5580
atttgcatgg tttgttgaaa accggacatg gcactccagt cgccttcccg ttccgctatc   5640
```

-continued

```
ggctgaattt gattgcgagt gagatattta tgccagccag ccagacgcag acgcgccgag        5700
acagaactta atgggcccgc taacagcgcg atttgctggt gacccaatgc gaccagatgc        5760
tccacgccca gtcgcgtacc gtcttcatgg gagaaaataa tactgttgat gggtgtctgg        5820
tcagagacat caagaaataa cgccggaaca ttagtgcagg cagcttccac agcaatggca        5880
tcctggtcat ccagcggata gttaatgatc agcccactga cgcgttgcgc gagaagattg        5940
tgcaccgccg ctttacaggc ttcgacgccg cttcgttcta ccatcgacac caccacgctg        6000
gcacccagtt gatcggcgcg agatttaatc gccgcgacaa tttgcgacgg cgcgtgcagg        6060
gccagactgg aggtggcaac gccaatcagc aacgactgtt tgcccgccag ttgttgtgcc        6120
acgcggttgg gaatgtaatt cagctccgcc atcgccgctt ccactttttc ccgcgttttc        6180
gcagaaacgt ggctggcctg gttcaccacg cgggaaacgg tctgataaga gacaccggca        6240
tactctgcga catcgtataa cgttactggt ttcacattca ccaccctgaa ttgactctct        6300
tccgggcgct atcatgccat accgcgaaag gttttgcgcc attcgatggt gtccgggatc        6360
tcgacgctct cccttatgcg actcctgcat taggaagcag cccagtagta ggttgaggcc        6420
gttgagcacc gccgccgcaa ggaatggtgc atgcaaggag atggcgccca acagtccccc        6480
ggccacgggg cctgccacca tacccacgcc gaaacaagcg ctcatgagcc cgaagtggcg        6540
agcccgatct ccccatcgg tgatgtcggc gatataggcg ccagcaaccg cacctgtggc         6600
gccggtgatg ccgccacga tgcgtccggc gtagaggatc gagatctcga tcccgcgaaa         6660
ttaatacgac tcactatagg ggaattgtga gcggataaca attcccctct agaaataatt        6720
ttgtttaact ttaagaag                                                      6738
```

<210> SEQ ID NO 23
<211> LENGTH: 10331
<212> TYPE: DNA
<213> ORGANISM: Artificial Sequence
<220> FEATURE:
<223> OTHER INFORMATION: synthetic construct

<400> SEQUENCE: 23

```
aagcttgcat gagcatgtca cagtcgaatt ctggggtcac gcggtgcttg agggcgaata         60
cggctccatc ggtgagtaac ctctctctta ctaccacgga acatcactg acgtaaccag         120 gacccggcgg cttatccatc atgggaaaca acacctacaa atccgccaga attctctcgg        180
aagaatataa cctctactac tccgtctggt gcgacggtga ccacgagctg tacgatctct        240
cagtaagtgc caaccggttc ccgccactat cgtaaaaaca aaaatctaa caacaccaga         300 cggaccccta ccaaatgaac aacatctaca cccaacaaga caacatccac ctcctaagca        360
gacctctatc cagcgtgatt gatcgtatcg acgctctcct tctggttctg aaatcctgca        420
agggtaacac atgcatccag ccgtggcggg tcctccaccc cgacgggtcc gtagagagcc        480
tcaaagatgc actgcaggtg aaatacgatt ccttttacac caaccagccc aaggtgtcgt        540
attcagtatg tgaacccggg tacatcattg aggctgaggg gccccaggtc ggattgcagt        600
atagagatgg gctgagttgg gaggcgtgga cttgacgatt ccgtcaagta tgagtatggg        660
tacgaataat gagcgttatt gctatgtatt tttatagata gtttatttat atatcatgac        720
taaacttgag agccatggaa tcaatgaaat gacatggcga gtgtagatca cgatagtcat        780
agtagccgaa gtgggcggat agccaagaat aacaccagaa tcagataaca ggaacatcac        840
aaccgatcac accatagata atatccaaag aagtttaaat agccgagaca agagaaatag        900
agacaagata catggaacaa gaaaggtaca cccggtagat aaaccctggg acgggcccga        960
```

```
gtccttaccc atagatcaat cccacgggaa caaaaccaaa gtcaacaacc accaccacca    1020
ttaccacaac cgcatcaata gaaccggtga aaaatgacac catcgaatcc ttcaccctaa    1080
gtaaagccct gtacgttgca tatcgcttaa gcacaaaagt agtagaatag atatgagccc    1140
gcacgcgcgg ccaacgatcc aaactagccc tgacatcaaa gccagcggcg attgcgccat    1200
caagcccccg tctcacttca tagtggaatt gcgggtcacc tcactgattg actgtctgtc    1260
tagacacact cacccacgca tgctgtctgt gcccagaacg tggactttgg ctctgccgag    1320
ctagaggatc aaatataagt agattggatg taggcccgta ttttttttat ttcgtgtgac    1380
tcggagattt tatgcgttgt gttgttgggc ggaaaaagaa atatactttc tttttgttct    1440 tttcttttc tctctattgc ttgccttgga tatcccttgc atacggtcgg ttgctgattg    1500
actaagggtg ctgtcttgtg tcactgaact gctgctcaac ctctgtctgg tattcctgtt    1560
gtcgtgatgg tggggaaaca gttcgagttc gaggaccaga gggatggcat cgtgcctccc    1620
ttggaggaaa agaaggtcgt cgatgaggtc tataccgata atgatgttgc gtcggaggag    1680
attgtcaagg actgggatga taaggaggag ggcaagctgc ggaggaagtg agtcgtcact    1740
gttttcattc actgccatat aggttcaagc atatactgac tggtatatag gatcgatatc    1800
atcctcatcc ccattctcgc tctcgctttc ttcggcctcc agattgatcg cggcaatatc    1860
agcgcagctc ttacctccac tatcaccgaa gacctaggtg tcaccacgaa ccaaatcaat    1920
attggaaccc agttgctttc ggctggtatt gtcatcaccg agatcccgtc aaatattata    1980
cttcagcgca tcggtcccca ggtctggttg tcggcacagc tgatcgcttg ggtctggtt    2040 ggcacattcc aggcttttgt acagtcgtac ccggcgtatc tggccacgag gttgttgctg    2100
gggctgttgg agggaggggtt tattcctggt ttgtctggtc gtgcgccttg gtctatggtg    2160
gtagcgctaa caatgggttt ggtacaggtg ccctgtacta tctctcgaca tggtataaac    2220
gtcctgagac gagtttccgg accactctgt tcttctatgg gcagatgttt gccggtgcga    2280
cctcgagcgg ccgcttcgag gattgcctga acattgacat tcggcgtccg gccgggacca    2340
ccgcggactc gaagctgcct gtgctggtct ggatctttgg cggaggcttt gaacttggtt    2400
caaaggcgat gtatgatggt acaacgatgg tatcatcgtc gatagacaag aacatgccta    2460
tcgtgtttgt agcaatgaat tatcgcgtgg gaggtttcgg gttcttgccc ggaaaggaga    2520
tcctggagga cgggtccgcg aacctagggc tcctggacca acgccttgcc ctgcagtggg    2580
ttgccgacaa catcgaggcc tttggtggag acccggacaa ggtgacgatt tggggagaat    2640
cagcaggagc catttccgtt tttgatcaga tgatcttgta cgacggaaac atcacttaca    2700
aggataagcc cttgttccgg ggggccatca tggactccgg tagtgttgtt cccgcagacc    2760
ccgtcgatgg ggtcaaggga cagcaagtat atgatgcggt agtggaatct gcaggctgtt    2820
cctcttctaa cgacacccta gcttgtctgc gtgaactaga ctacaccgac ttcctcaatg    2880
cggcaaactc cgtgccaggc attttaagct accattctgt ggcgttatca tatgtgcctc    2940
gaccggacgg gacggcgttg tcggcatcac cggacgtttt gggcaaagca gggaaatatg    3000
ctcgggtccc gttcatcgtg ggcgaccaag aggatgaggg gaccttattc gccttgtttc    3060
agtccaacat tacgacgatc gacgaggtgg tcgactacct ggcctcatac ttcttctatg    3120
acgctagccg agagcagctt gaagaactag tggccctgta cccagacacc accacgtacg    3180
ggtctccgtt caggacaggc gcggccaaca actggtatcc gcaatttaag cgattggccg    3240
ccattctcgg cgacttggtc ttcaccatta cccggcgggc attcctctcg tatgcagagg    3300
```

```
aaatctcccc tgatcttccg aactggtcgt acctggcgac ctatgactat ggcaccccag   3360
ttctggggac cttccacgga agtgacctgc tgcaggtgtt ctatgggatc aagccaaact   3420
atgcagctag ttctagccac acgtactatc tgagctttgt gtatacgctg atccgaact    3480 ccaaccgggg ggagtacatt gagtggccgc agtggaagga atcgcggcag ttgatgaatt   3540
tcggagcgaa cgacgccagt ctccttacgg atgatttccg caacgggaca tatgagttca   3600
tcctgcagaa taccgcggcg ttccacatct gatgccattg gcggaggggt ccggacggtc   3660
aggaacttag ccttatgaga tgaatgatgg acgtgtctgg cctcggaaaa ggatatatgg   3720
ggatcatgat agtactagcc atattaatga agggcatata ccacgcgttg gacctgcgtt   3780
atagcttccc gttagttata gtaccatcgt tataccagcc aatcaagtca ccacgcacga   3840
ccggggacgg cgaatcccg ggaattgaaa gaaattgcat cccaggccag tgaggccagc    3900
gattggccac ctctccaagg cacagggcca ttctgcagcg ctggtggatt catcgcaatt   3960
tcccccggcc cggcccgaca ccgctatagg ctggttctcc cacaccatcg gagattcgtc   4020
gcctaatgtc tcgtccgttc acaagctgaa gagcttgaag tggcgagatg tctctgcagg   4080
aattcaagct agatgctaag cgatattgca tggcaatatg tgttgatgca tgtgcttctt   4140
ccttcagctt cccctcgtgc agatgaggtt tggctataaa ttgaagtggt tggtcggggt   4200
tccgtgaggg gctgaagtgc ttcctcccct ttagacgcaa ctgagagcct gagcttcatc   4260
cccagcatca ttacacctca gcaatgggcg tctctgctgt tctacttcct ttgtatctcc   4320
tgtctgggta tgctaagcac cacaatcaaa gtctaataag gaccctccct tccgagggcc   4380
cctgaagctc ggactgtgtg ggactactga tcgctgacta tctgtgcaga gtcacctccg   4440
gactggcagt ccccagtgat accgccctg ctgggttcca gttggaaaag gttgttatcc    4500
taagcagaca tggcgtacgc gcgccaacca aaatgacaca aacgatgcgc aacgtcacac   4560
ctcaccagtg gcctgaatgg ccggtaaaac tcggctatat cacgccccgc ggtgaacatc   4620
tgattagcct gatgggcggt ttttatcgag agcgctttca gcaacaaggc ttattaccta   4680
aggataactg tcctacacca gatgccgtgt atgtttgggc agacgtcgat caacgcacac   4740
gtaaaaccgg cgaggccttc ttagcgggtc ttgctcccca gtgtgattta gcgatccacc   4800
atcagcaaaa cattcagcag gccgatccgc tgttccatcc tgtgaaagcc ggtatctgtt   4860
cgatggataa atcacaggca cacgccgccg ttgaaaagca ggcaggcaca ccgattgaga   4920
cgctcaatca acgctatcaa gcatctttag cgctgatgag ttcggtactc gattttccaa   4980 aatccccta ttgtcagcag cacaacattg gcaaactctg cgattttca caggcgatgc     5040 ctagcaggct ggcgataaat gacgacggta ataaagtggc tctcgaaggt gccgtgggac   5100
tttcatcgac gttggctgaa attttcctgc tggaacacgc tcagggaatg cctaaagtgg   5160
cttgggggaa tattcacact gagcagcaat gggactctct gttaaaattg cataatgcgc   5220
agtttgactt gatgtcgcgc acgccctata tcgccaagca taacggtact ccactgctgc   5280
aaaccatcgc acacgcactg ggttccaata tcgcgagtcg cccactgccg atatttcgc    5340 cagacaataa gatcctgttt attgccggtc acgacaccaa tattgccaat atttctggca   5400
tgctagggat gacatggaca cttccgggac agcccgataa caccccgccg ggtgggggc    5460 tggtgtttga actatggcag aatccagata accatcagca atatgtcgca gttaagatgt   5520
tctatcaaac aatggatcag ttacgaaata gtgaaaagtt agacctgaaa agtcatccag   5580
ccggtattgt tcccattgag atcgaaggtt gtgagaacat cggtacagac aaactttgcc   5640
agcttgatac cttccaaaag agagtggctc aggtgattga acctgcatgc catatttaga   5700
```

```
caatcaatcc atttcgctat agttaaagga tggggatgag ggcaattggt tatatgatca    5760
tgtatgtagt gggtgtgcat aatagtagtg aaatggaagc caagtcatgt gattgtaatc    5820
gaccgacgga attgaggata tccggaaata cagacaccgt gaaagccatg gtctttcctt    5880
cgtgtagaag accagacaga cagtccctga tttaccctgc acaaagcact agaaaattag    5940
cattccatcc ttctctgctt gctctgctga tatcactgtc attcaatgca tagccatgag    6000
ctcatcttag atccaagcac gtaattccat agccgaggtc cacagtggag cagcaacatt    6060
ccccatcatt gctttcccca ggggcctccc aacgactaaa tcaagagtat atctctaccg    6120
tccaatagat cgtcttcgct tcaaaatctt tgacaattcc aagagggtcc catccatca     6180 aacccagttc aataatagcc gagatgcatg gtggagtcaa ttaggcagta ttgctggaat    6240
gtcggggcca gttccgggtg gtcattggcc gcctgtgatg ccatctgcca ctaaatccga    6300
tcattgatcc accgcccacg agggcgtctt tgcttttttgc gcggcgtcca ggttcaactc    6360
tctctgcagc tccagtccaa cgctgactga ctagtttacc tactggtctg atcggctcca    6420
tcagagctat ggcgttatcc cgtgccgttg ctgcgcaatc gctatcttga tcgcaacctt    6480
gaactcactc ttgttttaat agtgatcttg gtgacggagt gtcggtgagt gacaaccaac    6540
atcgtgcaag ggagattgat acggaattgt cgctcccatc atgatgttct gccggctttt    6600
gttggcccta ttcgtgggat cgatgccctc tgtgcagca gcaggtactg ctggatgagg     6660
agccatcggt ctctgcacgc aaacccaact tcctcttcat tctcacggat gatcaggatc    6720
tccggatgaa ttctccggcg tatatgccgt atacgcaggc gagaatcaag gaaaagggta    6780
ccgagttctt gaaccatttc gtcactaccg cgctttgctg tccgtcgcgc gtgagtcttt    6840
ggacgggaag acaggctcat aatactaatg tgacggatgt gaacccgcct tatggtatgg    6900
acactgcttc gatcggtctt gattcttcag cgtggttaca attgctaatg cggcataggc    6960 ggataccccca aattcgtcgc tcaaggcttc aacgaaaact tcctcccgt ttggctgcag    7020 tccgccggtt acaataccta ctacacgggg aagctgttca actcgcacag tgtcgctacc    7080
tataacgcgc cctttgtgaa cggtttcaat ggctccgact tcctcctcga cccccacaca    7140
tattcctact ggaatgcgac ataccagcga aaccatgagc ctccgcggag ttacgaggga    7200
caatatacta cggatgtgat gaaggagaag gcatcgggat tgttggcaga tgcgctggac    7260
agtgacgcgc cattcttcct gacggtcgcg ccgatcgcac cgcacacgaa catcgatgtg    7320
gaggggctga gcggtgcggg tggaccgaag atgacagagc cgctgcctgc accgagacat    7380
gcgcatttgt ttgctgatgc aaaggtgccg cggacgccta atttcaatcc ggacaaggtg    7440
tgtgatatcc tgacacagtg gtggggacgg gcactgacaa gagtaggatt ctggtgcggg    7500
gtggatccaa accatggaac tacagaacca gaccgtcatc gactacgaag accatcttta    7560
tcgccagcgt ctgcgcactt tgcaagccgt cgatgagatg gtggatgcgc tgatcacgca    7620
gctggaagaa agtgggcaga tcgacaatac ctacatcatt tacagtgctg ataacggcta    7680
ccacattggc catcaccgtc tacccccggg caagacaact ggctatgaag aggacattcg    7740
cgtaccattc tacattcgcg gacctggcat tcctgaggga aagagcgttg accgtgtaac    7800
cacgcacatt gacattgcac ctacactgtt cgagttggct ggggttccct tgcgagagga    7860
ctttgacggg actccgatgc ccgtgtcgac tagcaagaag acccagtcaa gcttgcatgc    7920
ctgcaggtcg actctagagg atctgccggt ctccctatag tgagtcgtat taatttcgat    7980
aagccaggtt aacctgcatt aatgaatcgg ccaacgcgcg gggagaggcg gtttgcgtat    8040
```

```
tgggcgctct tccgcttcct cgctcactga ctcgctgcgc tcggtcgttc ggctgcggcg    8100
agcggtatca gctcactcaa aggcggtaat acggttatcc acagaatcag gggataacgc    8160
aggaaagaac atgtgagcaa aaggccagca aaaggccagg aaccgtaaaa aggccgcgtt    8220
gctggcgttt ttccataggc tccgcccccc tgacgagcat cacaaaaatc gacgctcaag    8280
tcagaggtgg cgaaacccga caggactata aagataccag gcgtttcccc ctggaagctc    8340
cctcgtgcgc tctcctgttc cgaccctgcc gcttaccgga tacctgtccg cctttctccc    8400
ttcgggaagc gtggcgcttt ctcatagctc acgctgtagg tatctcagtt cggtgtaggt    8460
cgttcgctcc aagctgggct gtgtgcacga accccccgtt cagcccgacc gctgcgcctt    8520
atccggtaac tatcgtcttg agtccaaccc ggtaagacac gacttatcgc cactggcagc    8580
agccactggt aacaggatta gcagagcgag gtatgtaggc ggtgctacag agttcttgaa    8640
gtggtggcct aactacggct acactagaag gacagtattt ggtatctgcg ctctgctgaa    8700
gccagttacc ttcggaaaaa gagttggtag ctcttgatcc ggcaaacaaa ccaccgctgg    8760
tagcggtggt ttttttgttt gcaagcagca gattacgcgc agaaaaaaag gatctcaaga    8820
agatcctttg atcttttcta cggggtctga cgctcagtgg aacgaaaact cacgttaagg    8880
gattttggtc atgagattat caaaaaggat cttcacctag atccttttaa attaaaaatg    8940
aagttttaaa tcaatctaaa gtatatatga gtaaacttgg tctgacagtt accaatgctt    9000
aatcagtgag gcacctatct cagcgatctg tctatttcgt tcatccatag ttgcctgact    9060
ccccgtcgtg tagataacta cgatacggga gggcttacca tctggcccca gtgctgcaat    9120
gataccgcga gacccacgct caccggctcc agatttatca gcaataaacc agccagccgg    9180
aagggccgag cgcagaagtg gtcctgcaac tttatccgcc tccatccagt ctattaattg    9240
ttgccgggaa gctagagtaa gtagttcgcc agttaatagt ttgcgcaacg ttgttgccat    9300
tgctacaggc atcgtggtgt cacgctcgtc gtttggtatg gcttcattca gctccggttc    9360
ccaacgatca aggcgagtta catgatcccc catgttgtgc aaaaaagcgg ttagctcctt    9420
cggtcctccg atcgttgtca gaagtaagtt ggccgcagtg ttatcactca tggttatggc    9480
agcactgcat aattctctta ctgtcatgcc atccgtaaga tgcttttctg tgactggtga    9540
gtactcaacc aagtcattct gagaatagtg tatgcggcga ccgagttgct cttgcccggc    9600
gtcaatacgg gataataccg cgccacatag cagaacttta aaagtgctca tcattggaaa    9660
acgttcttcg gggcgaaaac tctcaaggat cttaccgctg ttgagatcca gttcgatgta    9720
acccactcgt gcacccaact gatcttcagc atcttttact ttcaccagcg tttctgggtg    9780
agcaaaaaca ggaaggcaaa atgccgcaaa aaagggaata agggcgacac ggaaatgttg    9840
aatactcata ctcttccttt ttcaatatta ttgaagcatt tatcagggtt attgtctcat    9900
gagcggatac atatttgaat gtatttagaa aaataaacaa ataggggttc cgcgcacatt    9960
tccccgaaaa gtgccacctg acgtctaaga aaccattatt atcatgacat aacctataa   10020
aaataggcgt atcacgaggc cctttcgtct cgcgcgtttc ggtgatgacg gtgaaaacct   10080
ctgacacatg cagctcccgg agacggtcac agcttgtctg taagcggatg ccgggagcag   10140
acaagcccgt cagggcgcgt cagcgggtgt tggcgggtgt cggggctggc ttaactatgc   10200
ggcatcagag cagattgtac tgagagtgca ccatatggac atattgtcgt tagaacgcgg   10260
ctacaattaa tacataaccT tatgtatcat acacatacga tttaggtgac actatagaac   10320
tcgagcagct g                                                        10331
```

<210> SEQ ID NO 24
<211> LENGTH: 414
<212> TYPE: PRT
<213> ORGANISM: Artificial Sequence
<220> FEATURE:
<223> OTHER INFORMATION: synthetic construct

<400> SEQUENCE: 24

```
Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro His Gln Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Thr Asp Val Asn Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Thr Gln Val Asp Pro Leu Phe His
        115                 120                 125

Pro Val Lys Ala Gly Ile Cys Ser Met Asn Lys Ser Gln Thr Tyr Glu
    130                 135                 140

Ala Val Glu Lys Gln Ala Gly Gly Pro Ile Glu Thr Leu Asn Gln Arg
145                 150                 155                 160

Tyr Gln Ala Glu Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Asn Ile Ser Asp Asp Gly Asn Glu Val
        195                 200                 205

Gln Leu Glu Gly Ala Val Gly Leu Gly Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Asn Glu Ser Gln Trp Lys Ser Leu Leu Asn Leu His Asn Ala His
                245                 250                 255

Phe Asn Leu Met His Arg Thr Pro Tyr Ile Ala Lys His Gln Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Gly Gly Met Leu Gly Met Asn
305                 310                 315                 320

Trp Thr Leu Pro Gly Gln Pro Asp Asn Thr Pro Gly Gly Leu
                325                 330                 335

Val Phe Glu Leu Trp Gln Asn Pro Asp Asn His Gln Tyr Val Ala
            340                 345                 350

Val Lys Met Ile Tyr Gln Thr Met Asp Gln Leu Arg Asn Ser Glu Lys
        355                 360                 365

Leu Asp Leu Lys Ser Asn Pro Ala Gly Ile Val Pro Ile Glu Ile Glu
```

```
        370                 375                 380
Gly Cys Glu Asn Ile Gly Thr Asp Lys Leu Cys Gln Leu Asp Thr Phe
385                 390                 395                 400

Gln Lys Arg Val Ala Gln Val Ile Glu Pro Ala Cys Gln Ile
                405                 410

<210> SEQ ID NO 25
<211> LENGTH: 1245
<212> TYPE: DNA
<213> ORGANISM: Artificial Sequence
<220> FEATURE:
<223> OTHER INFORMATION: synthetic gene adapted to Aspergillus niger
      codon usage

<400> SEQUENCE: 25
agcgataccg cccccgcggg cttccagctg gagaaggtgg tcattctctc gcgtcacggt    60
gtccgagccc ccaccaagat gacacagacg atgcgcgatg tcactccaca tcagtggcct   120
gagtggcccg tgaagctcgg ctacatcact cctcgtggag aacacctcat cagcctgatg   180
ggcggtttct atagggaacg gttccagcag cagggattgc ttcccaagga caactgtccg   240
acccccgacg ccgtctacgt gtggaccgac gttaaccagc gtacccgcaa gactggagag   300
gctttcctcg ccggtcttgc gcctcagtgt gatctggcca tccaccacca gcagaacatc   360
acgcaggtcg acccgctgtt tcacccggtc aaggccggta tctgttcgat gaacaagtct   420
cagacctatg aggctgtcga gaagcaggct ggcggcccta ttgagacgct aaaccagcgc   480
taccaggccg aactggcatt gatgtcctct gtgttggatt ccccaagtc cccatattgc   540 cagcagcata acatcggcaa actgtgcgac ttttcacagg ctatgcctag ccgcctcaac   600
atctccgatg acgggaatga ggtgcaactc gaaggcgccg tcggtcttgg ttccacgctc   660
gccgagatct tcctactgga atacgctcag ggtatgcctg tggtcgcctg gggcaacatt   720
cacaacgaga gccagtggaa gagcctcctt aacttgcaca cgcccatttt caacctgatg   780
cacagaacgc cctacattgc caagcaccag ggaaccccctt tacttcaggc tatcagcaac   840
gctctcaacc caaatgcaac tgagtcgaag ctccccgata tctctcccga caacaagatc   900
cttttcattg ccggccacga caccaacatc gcaaacatcg gaggcatgtt gggtatgaac   960
tggactctcc cgggccagcc agacaatact ccgcccggcg gtggactggt tttcgaactc  1020
tggcagaacc cggataacca tcagcagtac gttgcggtga agatgatcta ccagaccatg  1080
gaccagctgc gcaattccga gaagctggac ttgaagagca ccctgctgg gatcgtcccc  1140 attgagatca aaggttgcga gaacatcggt accgacaagc tgtgccagct ggatactttt  1200
cagaagcgtg ttgcccaggt cattgagccc gcgtgccaaa tctaa              1245

<210> SEQ ID NO 26
<211> LENGTH: 10331
<212> TYPE: DNA
<213> ORGANISM: Artificial Sequence
<220> FEATURE:
<223> OTHER INFORMATION: synthetic construct

<400> SEQUENCE: 26
aagcttgcat gagcatgtca cagtcgaatt ctggggtcac gcggtgcttg agggcgaata    60
cggctccatc ggtgagtaac ctctctctta ctaccacgga acatcactg acgtaaccag    120 gacccggcgg cttatccatc atgggaaaca acacctacaa atccgccaga attctctcgg   180
aagaatataa cctctactac tccgtctggt gcgacggtga ccacgagctg tacgatctct   240
```

```
cagtaagtgc caaccggttc ccgccactat cgtaaaaaca aaaaatctaa caacaccaga    300 cggacccta ccaaatgaac aacatctaca cccaacaaga caacatccac ctcctaagca    360
gacctctatc cagcgtgatt gatcgtatcg acgctctcct tctggttctg aaatcctgca    420
agggtaacac atgcatccag ccgtggcggg tcctccaccc cgacgggtcc gtagagagcc    480
tcaaagatgc actgcaggtg aaatacgatt cctttacac caaccagccc aaggtgtcgt    540
attcagtatg tgaacccggg tacatcattg aggctgaggg gccccaggtc ggattgcagt    600
atagagatgg gctgagttgg gaggcgtgga cttgacgatt ccgtcaagta tgagtatggg    660
tacgaataat gagcgttatt gctatgtatt tttatagata gtttatttat atatcatgac    720
taaacttgag agccatggaa tcaatgaaat gacatggcga gtgtagatca cgatagtcat    780
agtagccgaa gtgggcggat agccaagaat aacaccagaa tcagataaca ggaacatcac    840
aaccgatcac accatagata atatccaaag aagtttaaat agccgagaca aagagaatag    900
agacaagata catggaacaa gaaaggtaca cccggtagta aaaccctggg acgggcccga    960
gtccttaccc atagatcaat cccacgggaa caaaaccaaa gtcaacaacc accaccacca   1020
ttaccacaac cgcatcaata gaaccggtga aaaatgacac catcgaatcc ttcaccctaa   1080
gtaaagccct gtacgttgca tatcgcttaa gcacaaaagt agtagaatag atatgagccc   1140
gcacgcgcgg ccaacgatcc aaactagccc tgacatcaaa gccagcggcg attgcgccat   1200
caagcccccg tctcacttca tagtggaatt gcgggtcacc tcactgattg actgtctgtc   1260
tagacacact caccacgca tgctgtctgt gcccagaacg tggactttgg ctctgccgag   1320
ctagaggatc aaatataagt agattggatg taggcccgta tttttttat ttcgtgtgac    1380 tcggagattt tatgcgttgt gttgttgggc ggaaaaagaa atatactttc ttttgttct   1440 tttcttttc tctctattgc ttgccttgga tatcccttgc atacggtcgg ttgctgattg   1500
actaagggtg ctgtcttgtg tcactgaact gctgctcaac ctctgtctgg tattcctgtt   1560
gtcgtgatgg tggggaaaca gttcgagttc gaggaccaga gggatggcat cgtgcctccc   1620
ttggaggaaa agaaggtcgt cgatgaggtc tataccgata tgatgttgc gtcggaggag   1680 attgtcaagg actgggatga taaggaggag ggcaagctgc ggaggaagtg agtcgtcact   1740
gttttcattc actgccatat aggttcaagc atatactgac tggtatatag gatcgatatc   1800
atcctcatcc ccattctcgc tctcgctttc ttcggcctcc agattgatcg cggcaatatc   1860
agcgcagctc ttacctccac tatcaccgaa gacctaggtg tcaccacgaa ccaaatcaat   1920
attggaaccc agttgctttc ggctggtatt gtcatcaccg agatcccgtc aaatattata   1980
cttcagcgca tcggtcccca ggtctggttg tcggcacagc tgatcgcttg ggtctggtt   2040 ggcacattcc aggcttttgt acagtcgtac ccggcgtatc tggccacgag gttgttgctg   2100
gggctgttgg agggagggtt tattcctggt ttgtctggtc gtgcgccttg gtctatggtg   2160
gtagcgctaa caatgggttt ggtacaggtg ccctgtacta tctctcgaca tggtataaac   2220
gtcctgagac gagtttccgg accactctgt tcttctatgg gcagatgttt gccggtgcga   2280
cctcgagcgg ccgcttcgag gattgcctga acattgacat tcggcgtccg gccgggacca   2340
ccgcggactc gaagctgcct gtgctggtct ggatctttgg cggaggcttt gaacttggtt   2400
caaaggcgat gtatgatggt acaacgatgg tatcatcgtc gatagacaag aacatgccta   2460 tcgtgttgt agcaatgaat tatcgcgtgg gaggtttcgg gttcttgccc ggaaaggaga   2520
tcctggagga cgggtccgcg aacctagggc tcctggacca acgccttgcc ctgcagtggg   2580
ttgccgacaa catcgaggcc tttggtggag acccggacaa ggtgacgatt tggggagaat   2640
```

```
cagcaggagc catttccgtt tttgatcaga tgatcttgta cgacggaaac atcacttaca    2700
aggataagcc cttgttccgg ggggccatca tggactccgg tagtgttgtt cccgcagacc    2760
ccgtcgatgg ggtcaaggga cagcaagtat atgatgcggt agtggaatct gcaggctgtt    2820
cctcttctaa cgacacccta gcttgtctgc gtgaactaga ctacaccgac ttcctcaatg    2880
cggcaaactc cgtgccaggc attttaagct accattctgt ggcgttatca tatgtgcctc    2940
gaccggacgg gacggcgttg tcggcatcac cggacgtttt gggcaaagca gggaaatatg    3000
ctcgggtccc gttcatcgtg ggcgaccaag aggatgaggg gaccttattc gccttgtttc    3060
agtccaacat tacgacgatc gacgaggtgg tcgactacct ggcctcatac ttcttctatg    3120
acgctagccg agagcagctt gaagaactag tggccctgta cccagacacc accacgtacg    3180
ggtctccgtt caggacaggc gcggccaaca actggtatcc gcaatttaag cgattggccg    3240
ccattctcgg cgacttggtc ttcaccatta cccggcgggc attcctctcg tatgcagagg    3300
aaatctcccc tgatcttccg aactggtcgt acctggcgac ctatgactat ggcaccccag    3360
ttctggggac cttccacgga agtgacctgc tgcaggtgtt ctatgggatc aagccaaact    3420
atgcagctag ttctagccac acgtactatc tgagctttgt gtatacgctg atccgaact     3480 ccaaccgggg ggagtacatt gagtggccgc agtggaagga atcgcggcag ttgatgaatt    3540
tcggagcgaa cgacgccagt ctccttacgg atgatttccg caacgggaca tatgagttca    3600
tcctgcagaa taccgcggcg ttccacatct gatgccattg gcggaggggt ccggacggtc    3660
aggaacttag ccttatgaga tgaatgatgg acgtgtctgg cctcggaaaa ggatatatgg    3720
ggatcatgat agtactagcc atattaatga agggcatata ccacgcgttg gacctgcgtt    3780
atagcttccc gttagttata gtaccatcgt tataccagcc aatcaagtca ccacgcacga    3840
ccggggacgg cgaatccccg ggaattgaaa gaaattgcat cccaggccag tgaggccagc    3900
gattggccac ctctccaagg cacagggcca ttctgcagcg ctggtggatt catcgcaatt    3960
tcccccggcc cggcccgaca ccgctatagg ctggttctcc cacaccatcg gagattcgtc    4020
gcctaatgtc tcgtccgttc acaagctgaa gagcttgaag tggcgagatg tctctgcagg    4080
aattcaagct agatgctaag cgatattgca tggcaatatg tgttgatgca tgtgcttctt    4140
ccttcagctt cccctcgtgc agatgaggtt tggctataaa ttgaagtggt tggtcggggt    4200
tccgtgaggg gctgaagtgc ttcctcccct ttagacgcaa ctgagagcct gagcttcatc    4260
cccagcatca ttacacctca gcaatgggcg tctctgctgt tctacttcct ttgtatctcc    4320
tgtctgggta tgctaagcac cacaatcaaa gtctaataag gaccctccct tccgagggcc    4380
cctgaagctc ggactgtgtg ggactactga tcgctgacta tctgtgcaga gtcacctccg    4440
gactggcagt ccccagcgat accgcccccg cgggcttcca gctggagaag gtggtcattc    4500
tctcgcgtca cggtgtccga gcccccacca agatgacaca gacgatgcgc gatgtcactc    4560
cacatcagtg gcctgagtgg cccgtgaagc tcggctacat cactcctcgt ggagaacacc    4620
tcatcagcct gatgggcggt ttctataggg aacggttcca gcagcaggga ttgcttccca    4680
aggacaactg tccgaccccc gacgccgtct acgtgtggac cgacgttaac cagcgtaccc    4740
gcaagactgg agaggctttc ctcgccggtc ttgcgcctca gtgtgatctg gccatccacc    4800
accagcagaa catcacgcag gtcgacccgc tgtttcaccc ggtcaaggcc ggtatctgtt    4860
cgatgaacaa gtctcagacc tatgaggctg tcgagaagca ggctggcggc cctattgaga    4920
cgctaaacca gcgctaccag gccgaactgg cattgatgtc ctctgtgttg gatttcccca    4980
```

```
agtccccata ttgccagcag cataacatcg gcaaactgtg cgacttttca caggctatgc    5040
ctagccgcct caacatctcc gatgacggga atgaggtgca actcgaaggc gccgtcggtc    5100
ttggttccac gctcgccgag atcttcctac tggaatacgc tcagggtatg cctgtggtcg    5160
cctggggcaa cattcacaac gagagccagt ggaagagcct ccttaacttg cacaacgccc    5220
atttcaacct gatgcacaga acgccctaca ttgccaagca ccagggaacc cctttacttc    5280
aggctatcag caacgctctc aacccaaatg caactgagtc gaagctcccc gatatctctc    5340
ccgacaacaa gatcctttc attgccggcc acgacaccaa catcgcaaac atcggaggca    5400
tgttgggtat gaactggact ctcccgggcc agccagacaa tactccgccc ggcggtggac    5460
tggttttcga actctggcag aacccggata accatcagca gtacgttgcg gtgaagatga    5520
tctaccagac catggaccag ctgcgcaatt ccgagaagct ggacttgaag agcaaccctg    5580
ctgggatcgt ccccattgag atcgaaggtt gcgagaacat cggtaccgac aagctgtgcc    5640
agctggatac ttttcagaag cgtgttgccc aggtcattga gcccgcgtgc caaatctaaa    5700
caatcaatcc atttcgctat agttaaagga tggggatgag ggcaattggt tatatgatca    5760
tgtatgtagt gggtgtgcat aatagtagtg aaatggaagc caagtcatgt gattgtaatc    5820
gaccgacgga attgaggata tccggaaata cagacaccgt gaaagccatg gtctttcctt    5880
cgtgtagaag accagacaga cagtccctga tttaccctgc acaaagcact agaaaattag    5940
cattccatcc ttctctgctt gctctgctga tatcactgtc attcaatgca tagccatgag    6000
ctcatcttag atccaagcac gtaattccat agccgaggtc cacagtggag cagcaacatt    6060
ccccatcatt gctttcccca ggggcctccc aacgactaaa tcaagagtat atctctaccg    6120
tccaatagat cgtcttcgct tcaaaatctt tgacaattcc aagagggtcc ccatccatca    6180
aacccagttc aataatagcc gagatgcatg gtggagtcaa ttaggcagta ttgctggaat    6240
gtcggggcca gttccgggtg gtcattggcc gcctgtgatg ccatctgcca ctaaatccga    6300
tcattgatcc accgcccacg agggcgtctt tgcttttgc gcggcgtcca ggttcaactc    6360
tctctgcagc tccagtccaa cgctgactga ctagtttacc tactggtctg atcggctcca    6420
tcagagctat ggcgttatcc cgtgccgttg ctgcgcaatc gctatcttga tgcaacctt    6480 gaactcactc ttgttttaat agtgatcttg gtgacggagt gtcggtgagt gacaaccaac    6540
atcgtgcaag ggagattgat acggaattgt cgctcccatc atgatgttct tgccggcttt    6600
gttggcccta ttcgtgggat cgatgccctc ctgtgcagca gcaggtactg ctggatgagg    6660
agccatcggt ctctgcacgc aaacccaact tcctcttcat tctcacggat gatcaggatc    6720
tccggatgaa ttctccggcg tatatgccgt atacgcaggc gagaatcaag gaaagggta    6780 ccgagttctt gaaccatttc gtcactaccg cgctttgctg tccgtcgcgc gtgagtcttt    6840
ggacgggaag acaggctcat aatactaatg tgacggatgt gaacccgcct tatggtatgg    6900
acactgcttc gatcggtctt gattcttcag cgtggttaca attgctaatg cggcataggc    6960 ggataccca aattcgtcgc tcaaggcttc aacgaaaact tcctccccgt ttggctgcag    7020
tccgccggtt acaataccta ctacacgggg aagctgttca actcgcacag tgtcgctacc    7080
tataacgcgc cctttgtgaa cggtttcaat ggctccgact tcctcctcga cccccacaca    7140
tattcctact ggaatgcgac ataccagcga aaccatgagc ctccgcggag ttacgaggga    7200
caatatacta cggatgtgat gaaggagaag gcatcgggat tgttggcaga tgcgctggac    7260
agtgacgcgc cattcttcct gacggtcgcg ccgatcgcac cgcacacgaa catcgatgtg    7320
gaggggctga gcggtgcggg tggaccgaag atgacagagc cgctgcctgc accgagacat    7380
```

```
gcgcatttgt tgctgatgc aaaggtgccg cggacgccta atttcaatcc ggacaaggtg    7440
tgtgatatcc tgacacagtg gtggggacgg gcactgacaa gagtaggatt ctggtgcggg    7500
gtggatccaa accatggaac tacagaacca gaccgtcatc gactacgaag accatcttta    7560
tcgccagcgt ctgcgcactt tgcaagccgt cgatgagatg gtggatgcgc tgatcacgca    7620
gctggaagaa agtgggcaga tcgacaatac ctacatcatt tacagtgctg ataacggcta    7680
ccacattggc catcaccgtc tacccccegg caagacaact ggctatgaag aggacattcg    7740
cgtaccattc tacattcgcg gacctggcat tcctgaggga agagcgttg accgtgtaac     7800 cacgcacatt gacattgcac ctacactgtt cgagttggct ggggttccct tgcgagagga    7860
ctttgacggg actccgatgc ccgtgtcgac tagcaagaag acccagtcaa gcttgcatgc    7920
ctgcaggtcg actctagagg atctgccggt ctccctatag tgagtcgtat taatttcgat    7980
aagccaggtt aacctgcatt aatgaatcgg ccaacgcgcg gggagaggcg gtttgcgtat    8040
tgggcgctct tccgcttcct cgctcactga ctcgctgcgc tcggtcgttc ggctgcggcg    8100
agcggtatca gctcactcaa aggcggtaat acggttatcc acagaatcag gggataacgc    8160
aggaaagaac atgtgagcaa aaggccagca aaaggccagg aaccgtaaaa aggccgcgtt    8220
gctggcgttt ttccataggc tccgcccccc tgacgagcat cacaaaaatc gacgctcaag    8280
tcagaggtgg cgaaacccga caggactata aagataccag gcgtttcccc ctggaagctc    8340
cctcgtgcgc tctcctgttc cgaccctgcc gcttaccgga tacctgtccg cctttctccc    8400
ttcgggaagc gtggcgcttt ctcatagctc acgctgtagg tatctcagtt cggtgtaggt    8460
cgttcgctcc aagctgggct gtgtgcacga acccccgtt cagcccgacc gctgcgcctt     8520
atccggtaac tatcgtcttg agtccaaccc ggtaagacac gacttatcgc cactggcagc    8580
agccactggt aacaggatta gcagagcgag gtatgtaggc ggtgctacag agttcttgaa    8640
gtggtggcct aactacggct acactagaag gacagtattt ggtatctgcg ctctgctgaa    8700
gccagttacc ttcggaaaaa gagttggtag ctcttgatcc ggcaaacaaa ccaccgctgg    8760
tagcggtggt ttttttgttt gcaagcagca gattacgcgc agaaaaaaag gatctcaaga    8820
agatcctttg atcttttcta cggggtctga cgctcagtgg aacgaaaact cacgttaagg    8880
gattttggtc atgagattat caaaaaggat cttcacctag atccttttaa attaaaaatg    8940
aagttttaaa tcaatctaaa gtatatatga gtaaacttgg tctgacagtt accaatgctt    9000
aatcagtgag gcacctatct cagcgatctg tctatttcgt tcatccatag ttgcctgact    9060
ccccgtcgtg tagataacta cgatacggga gggcttacca tctggcccca gtgctgcaat    9120
gataccgcga gacccacgct caccggctcc agatttatca gcaataaacc agccagccgg    9180
aagggccgag cgcagaagtg gtcctgcaac tttatccgcc tccatccagt ctattaattg    9240
ttgccgggaa gctagagtaa gtagttcgcc agttaatagt ttgcgcaacg ttgttgccat    9300
tgctacaggc atcgtggtgt cacgctcgtc gtttggtatg gcttcattca gctccggttc    9360
ccaacgatca aggcgagtta catgatcccc catgttgtgc aaaaaagcgg ttagctcctt    9420
cggtcctccg atcgttgtca gaagtaagtt ggccgcagtg ttatcactca tggttatggc    9480
agcactgcat aattctctta ctgtcatgcc atccgtaaga tgcttttctg tgactggtga    9540
gtactcaacc aagtcattct gagaatagtg tatgcggcga ccgagttgct cttgcccggc    9600
gtcaatacgg gataataccg cgccacatag cagaacttta aaagtgctca tcattggaaa    9660
acgttcttcg gggcgaaaac tctcaaggat cttaccgctg ttgagatcca gttcgatgta    9720
```

```
acccactcgt gcacccaact gatcttcagc atctttact ttcaccagcg tttctgggtg    9780
agcaaaaaca ggaaggcaaa atgccgcaaa aaagggaata agggcgacac ggaaatgttg    9840
aatactcata ctcttccttt ttcaatatta ttgaagcatt tatcagggtt attgtctcat    9900
gagcggatac atatttgaat gtatttagaa aaataaacaa ataggggttc cgcgcacatt    9960
tccccgaaaa gtgccacctg acgtctaaga aaccattatt atcatgacat taacctataa   10020
aaataggcgt atcacgaggc cctttcgtct cgcgcgtttc ggtgatgacg gtgaaaacct   10080
ctgacacatg cagctcccgg agacggtcac agcttgtctg taagcggatg ccgggagcag   10140
acaagcccgt cagggcgcgt cagcgggtgt tggcgggtgt cggggctggc ttaactatgc   10200
ggcatcagag cagattgtac tgagagtgca ccatatggaa atattgtcgt tagaacgcgg   10260
ctacaattaa tacataacct tatgtatcat acacatacga tttaggtgac actatagaac   10320
tcgagcagct g                                                        10331
```